US012629088B2

(12) United States Patent
Waterhouse

(10) Patent No.: US 12,629,088 B2
(45) Date of Patent: May 19, 2026

(54) DEVICE FOR CORRELATING A BIOMETRIC VARIATION WITH AN EXTERNAL STIMULUS AND RELATED METHODS AND SYSTEMS

(71) Applicant: ALLERGY, INFLAMMATION AND THE MICROBIOME RESEARCH INSTITUTE INC., Middletown, DE (US)

(72) Inventor: Joyce Crescence Waterhouse, Pasadena, CA (US)

(73) Assignee: ALLERGY, INFLAMMATION AND THE MICROBIOME RESEARCH INSTITUTE INC., Middletown, DE (US)

( * ) Notice: Subject to any disclaimer, the term of this patent is extended or adjusted under 35 U.S.C. 154(b) by 611 days.

(21) Appl. No.: 17/818,973

(22) Filed: Aug. 10, 2022

(65) Prior Publication Data

US 2023/0210443 A1 Jul. 6, 2023

Related U.S. Application Data

(60) Provisional application No. 63/268,914, filed on Mar. 4, 2022, provisional application No. 63/232,087, filed on Aug. 11, 2021.

(51) Int. Cl.
*A61B 5/00* (2006.01)
*A61B 5/024* (2006.01)
(Continued)

(52) U.S. Cl.
CPC .............. *A61B 5/411* (2013.01); *A61B 5/024* (2013.01); *A61B 7/00* (2013.01); *G05B 13/0265* (2013.01);
(Continued)

(58) Field of Classification Search
USPC ........................................................... 700/47
See application file for complete search history.

(56) References Cited

U.S. PATENT DOCUMENTS 5,398,688 A * 3/1995 Laniado ............. A61B 5/02438
600/458
6,458,080 B1 * 10/2002 Brown ................... G16H 40/67
600/300
(Continued)

FOREIGN PATENT DOCUMENTS

EP 2541449 A1 1/2013
EP 3354193 B1 2/2021
(Continued)

OTHER PUBLICATIONS

Gutiérrez-Rivas, "Real-time early detection of allergic reactions based on heart rate variability" Doctoral Thesis, University College Cork, 2016, 217 pgs (Year: 2016).*

(Continued)

*Primary Examiner* — Emilio J Saavedra
(74) *Attorney, Agent, or Firm* — Steinfl + Bruno LLP

(57) ABSTRACT

Systems and methods for correlating inputs found external to a user to inputs measured from the user are disclosed, using wearables, various types of non-wearable sensors, and other external data sources and mobile device technology. Pattern matching and rules can be used to provide useful suggestions or control external machines based on the correlated inputs.

21 Claims, 25 Drawing Sheets

(51) Int. Cl.

| | |
|---|---|
| *A61B 7/00* | (2006.01) |
| *G05B 13/02* | (2006.01) |
| *G16H 50/30* | (2018.01) |
| *G16H 20/60* | (2018.01) |

(52) U.S. Cl.
CPC ............ *G16H 50/30* (2018.01); *A61B 5/7264*
(2013.01); *A61B 2562/0204* (2013.01); *G16H 20/60* (2018.01)

(56) References Cited

U.S. PATENT DOCUMENTS

| | | | |
|---|---|---|---|
| 8,696,616 B2 | 4/2014 | Baynham et al. | |
| 9,198,605 B2 | 12/2015 | Contant | |
| 9,198,621 B2 | 12/2015 | Fernstrom et al. | |
| 9,524,654 B2 | 12/2016 | Simons-Nikolova et al. | |
| 9,536,449 B2 | 1/2017 | Connor | |
| 9,839,377 B2 | 12/2017 | Hotta et al. | |
| 9,968,288 B2 | 5/2018 | Fuerst | |
| 10,431,340 B2 | 10/2019 | Fuerst | |
| 10,458,845 B2 | 10/2019 | Connor | |
| 10,548,469 B2 | 2/2020 | Weiss et al. | |
| 10,702,210 B2 | 7/2020 | Mori et al. | |
| 10,772,559 B2 | 9/2020 | Connor | |
| 10,791,988 B2 | 10/2020 | Dunki-Jacobs et al. | |
| 10,832,590 B2 | 11/2020 | Gopalan et al. | |
| 10,835,171 B2 | 11/2020 | Findlay et al. | |
| 10,888,272 B2 | 1/2021 | Hayter et al. | |
| 10,900,943 B2 | 1/2021 | Fernstrom et al. | |
| 10,952,670 B2 | 3/2021 | Mori et al. | |
| 10,980,477 B2 | 4/2021 | Chung et al. | |
| 11,191,466 B1 | 12/2021 | Heneghan et al. | |
| 2002/0176809 A1* | 11/2002 | Siess ..................... B03C 3/0175 | |
| | | | 422/123 |
| 2004/0220483 A1* | 11/2004 | Yeo ..................... A61B 5/1455 | |
| | | | 128/920 |
| 2006/0142968 A1* | 6/2006 | Han ..................... A61B 5/4809 | |
| | | | 702/120 |
| 2007/0004969 A1 | 1/2007 | Kong et al. | |
| 2008/0214903 A1 | 9/2008 | Orbach | |
| 2008/0294019 A1* | 11/2008 | Tran ..................... G16H 15/00 | |
| | | | 600/301 |
| 2013/0006063 A1 | 1/2013 | Wang | |
| 2014/0344282 A1 | 11/2014 | Stivoric et al. | |
| 2015/0132722 A1 | 5/2015 | Menczel et al. | |
| 2015/0302160 A1 | 10/2015 | Muthukumar et al. | |
| 2016/0080909 A1 | 3/2016 | Grossman et al. | |
| 2016/0324487 A1 | 11/2016 | Guo et al. | |
| 2017/0316164 A1 | 11/2017 | Casale et al. | |
| 2017/0374414 A1 | 12/2017 | Knox | |
| 2018/0114081 A1* | 4/2018 | Dejewski ............... G06V 40/70 | |
| 2018/0116543 A1 | 5/2018 | Miller et al. | |
| 2018/0169331 A1* | 6/2018 | Balachandran ..... A61M 5/1723 | |
| 2018/0184960 A1 | 7/2018 | Flax et al. | |
| 2018/0242909 A1* | 8/2018 | Mori ..................... A61B 5/7278 | |
| 2018/0285649 A1* | 10/2018 | Shi .................. G08B 13/19613 | |
| 2018/0322253 A1 | 11/2018 | Goyal et al. | |
| 2019/0015041 A1* | 1/2019 | Chung ................... A61B 5/742 | |
| 2019/0019581 A1 | 1/2019 | Vaughan et al. | |
| 2019/0125264 A1 | 5/2019 | Abreu Oramas | |
| 2019/0130076 A1 | 5/2019 | Chang et al. | |
| 2019/0156925 A1* | 5/2019 | Martinez-Arocho ........................ | |
| | | | G16H 15/00 |
| 2019/0290172 A1 | 9/2019 | Hadad et al. | |
| 2019/0295440 A1 | 9/2019 | Hadad | |
| 2019/0328316 A1 | 10/2019 | Fontanel et al. | |
| 2019/0387998 A1 | 12/2019 | Garten et al. | |
| 2020/0000395 A1* | 1/2020 | Ganesan ................ A61B 5/681 | |
| 2020/0077961 A1* | 3/2020 | Choi ..................... A61B 5/486 | |
| 2020/0152312 A1 | 5/2020 | Connor | |
| 2020/0214886 A1 | 7/2020 | Gutierrez | |
| 2020/0275848 A1 | 9/2020 | Goldberg et al. | |
| 2020/0294670 A1 | 9/2020 | Kotikela et al. | |
| 2021/0045696 A1 | 2/2021 | Poulin | |
| 2021/0085233 A1 | 3/2021 | Kotikela et al. | |

| | | | |
|---|---|---|---|
| 2021/0098110 A1 | 4/2021 | Periyasamy et al. | |
| 2021/0104173 A1 | 4/2021 | Pauley et al. | |
| 2021/0113095 A1* | 4/2021 | Knapp ................... A61B 5/742 | |
| 2021/0118546 A1 | 4/2021 | Ramakrishnan | |
| 2021/0118547 A1 | 4/2021 | Morris et al. | |
| 2021/0128062 A1 | 5/2021 | Karimli et al. | |
| 2021/0145338 A1 | 5/2021 | Borthakur | |
| 2021/0166804 A1 | 6/2021 | Metruck et al. | |
| 2021/0169389 A1 | 6/2021 | Moskowitz | |
| 2021/0174920 A1 | 6/2021 | Fan | |
| 2021/0193276 A1 | 6/2021 | Goyal et al. | |
| 2021/0212606 A1 | 7/2021 | Tran | |
| 2021/0267515 A1 | 9/2021 | Scanlin | |
| 2021/0287776 A1 | 9/2021 | Garcia Molina et al. | |
| 2021/0327591 A1 | 10/2021 | Harrison et al. | |
| 2021/0330253 A1 | 10/2021 | Wright et al. | |
| 2022/0076834 A1 | 3/2022 | Hanlon, Jr. et al. | |
| 2022/0084672 A1 | 3/2022 | Hall | |
| 2022/0130518 A1 | 4/2022 | Ozen Irmak et al. | |
| 2022/0148723 A1 | 5/2022 | Ramachandran et al. | |
| 2022/0165393 A1 | 5/2022 | Inz et al. | |
| 2022/0167916 A1 | 6/2022 | Mohanty et al. | |
| 2022/0199224 A1 | 6/2022 | Orellana Gonzalez et al. | |
| 2022/0208385 A1 | 6/2022 | Voschina et al. | |
| 2022/0261999 A1 | 8/2022 | Yildiz et al. | |
| 2022/0270731 A1 | 8/2022 | Abdullah et al. | |
| 2022/0296847 A1 | 9/2022 | Freckleton et al. | |
| 2022/0304602 A1 | 9/2022 | Zhou et al. | |
| 2022/0346704 A1 | 11/2022 | Milbert et al. | |
| 2022/0354395 A1 | 11/2022 | Frank et al. | |
| 2022/0369986 A1 | 11/2022 | Intrator | |
| 2022/0395222 A1 | 12/2022 | Yocca et al. | |
| 2022/0408147 A1 | 12/2022 | Howard | |
| 2023/0000423 A1 | 1/2023 | Sarkar et al. | |
| 2023/0000677 A1 | 1/2023 | Gutierrez | |
| 2023/0001932 A1 | 1/2023 | Sanchez | |
| 2023/0053198 A1 | 2/2023 | Skaltsounis et al. | |
| 2023/0083418 A1 | 3/2023 | McDuff et al. | |
| 2023/0106138 A1 | 4/2023 | Sethuraman et al. | |
| 2023/0114876 A1 | 4/2023 | Brincat et al. | |
| 2023/0115575 A1 | 4/2023 | Tily | |
| 2023/0128090 A1 | 4/2023 | Kaftarian | |
| 2023/0144761 A1 | 5/2023 | Singleton et al. | |
| 2023/0148863 A1 | 5/2023 | Sharareh | |
| 2023/0162835 A1 | 5/2023 | Ward | |
| 2023/0210443 A1 | 7/2023 | Waterhouse | |
| 2023/0346299 A1 | 11/2023 | Crescence | |

FOREIGN PATENT DOCUMENTS

| | | | |
|---|---|---|---|
| EP | 4385040 A1 | 6/2024 | |
| ES | 1225431 U * | 2/2019 | |
| JP | 2017505207 A | 2/2017 | |
| WO | 2020/074577 A1 | 4/2020 | |
| WO | 2021/040292 A1 | 3/2021 | |
| WO | 2023/018843 A1 | 2/2023 | |

OTHER PUBLICATIONS

Towney et al.,, "Automated Detection of Perturbed Cardiac Physiology During Oral Food Allergen Challenge in Children" IEEE Journal of Biomedical and Health Informatics, vol. 18, No. 3, May 2014, pp. 1051-1057 (Year: 2014).*

Restriction Requirement for U.S. Appl. No. 18/333,332, filed Jun. 12, 2023 on behalf of Allergy, Inflammation and the Microbiome Institute Inc. Mail Date: Sep. 8, 2023 8 pages.

Combs S. "A Simple At-Home Method for Testing Food Sensitivities" *Mt. Capra*, Retrieval Date: Feb. 1, 2023, 9 pages https://web.archive.org/web/20230201200916/https://mtcapra.com/a-simple-at-home-method-for-testing-food-sensitivities/.

Ettelson L.N. et al., "The value of the Coca pulse-acceleration method in food allergy" *Journal of Allergy*, vol. 32 No. 6, Dec. 1961, pp. 514-524.

Sherry L. "How to Test for Food Sensitivities at Home for Free" Real Healing Nutrition, Retrieval Date: Aug. 27, 2015 4 pages https://web.archive.org/web/20150827060720/https://realhealingnutrition.com/how-to-test-for-food-sensitivities-at-home-for-free/.

(56) References Cited

OTHER PUBLICATIONS

St. Cloud Chiropractic—"Coca Pulse Test" Retrieval Date: May 25, 2023 4 pages https://web.archive.org/web/20230525012149/https://www.saintcloudchiropractor.com/pulse-test.

Cordeiro F. et al., "Rethinking the Mobile Food Journal: Exploring Opportunities for Lightweight Photo-Based Capture" *Understanding healthy through Online Behavior*, 2015, pp. 3207-3216.

Final Office Action for U.S. Appl. No. 18/333,332, filed Jun. 12, 2023 on behalf of Allergy, Inflammation and the Microbiome Institute Inc. Mail Date: Mar. 21, 2024 16 pages.

International Preliminary Report on Patentability for International Application No. PCT/US2022/040011 filed on Aug. 10, 2022 on behalf of Allergy, Inflammation and the Microbiome Research Institute Inc. Mail Date: Feb. 22, 2024 10 pages.

Twomey N. et al., "Automated Detection of Perturbed Cardiac Physiology During Oral Food Allergen Challenge in Children" *IEEE Journal of Biomedical and Health Informatics*, vol. 18 No. 3, May 2014, pp. 1051-1057.

AppAdvice—Bulletproof Food Detective, *The Bulletproof Executive* Accessed Date: Jul. 18, 2023 5 pages https://appadvice.com/app/bulletproof-food-detective/899335465.

Asprey D. "Announcing: The Free Bulletproof Food Detective iPhone App!", daveasprey.com, Archive Date: Nov. 29, 2020 5 pages https://web.archive.org/web/20201129110414/https://daveasprey.com/find-your-kryptonite-with-the-free-bulletproof-food-sense-iphone-app/.

Non-Final Office Action for U.S. Appl. No. 18/333,332, filed Jun. 12, 2023 on behalf of Allergy, Inflammation and the Microbiome Institute Inc. Mail Date: Nov. 22, 2023 19 pages.

Gutierrez-Rivas R., "Real-Time Early Detection of Allergic Reactions based on Heart Rate Variability" *University College Cork, Ireland*, Publication Date: 2016, 217 pages.

Agrawal J. et al., "Efficient Pattern Matching over Event Streams" *SIGMOD* '08, Jun. 2008, pp. 147-160.

Black J. "Ways to measure pH" Carolina Knowledge Center, Accessed: Jul. 12, 2022, 5 pages.

Coca A.F. "Familial Nonreaginic Food-Allergy" *Lederle Laboratories*, 1943, 11 pages.

Coca A.F. "The Pulse Test" *Lyle Stuart New York*, Sep. 1956, 110 pages.

Cook V. R. "4 Ways to Measure Galvanic Skin Response (GSR)" ZYTO, Accessed: Jul. 12, 2022, 6 pages.

Electrodermal activity—Wikipedia, Accessed: Jul. 12, 2022, 8 pages https://en.wikipedia.org/wiki/Electrodermal_activity.

IMartCity—"There are four different ways to measure body temperature" *iMC*, Jul. 14, 2021, 4 pages.

International Search Report and Written Opinion for International Application No. PCT/US2022/040011 filed on Aug. 10, 2022 on behalf of Allergy, Inflammation and the Microbiome Research Institute Inc. Mail Date: Dec. 15, 2022 15 pages.

Maunelli A. "11 Types of Thermometers and Their Functions" YaleTools, Accessed: Jul. 12, 2022, 4 pages.

Extended European Search Report for European Patent Application No. 22856586.7 filed Mar. 8, 2024 on behalf of Allergy, Inflammation and the Microbiome Institute Inc. Mail Date: Jun. 5, 2025. 10 pages.

* cited by examiner

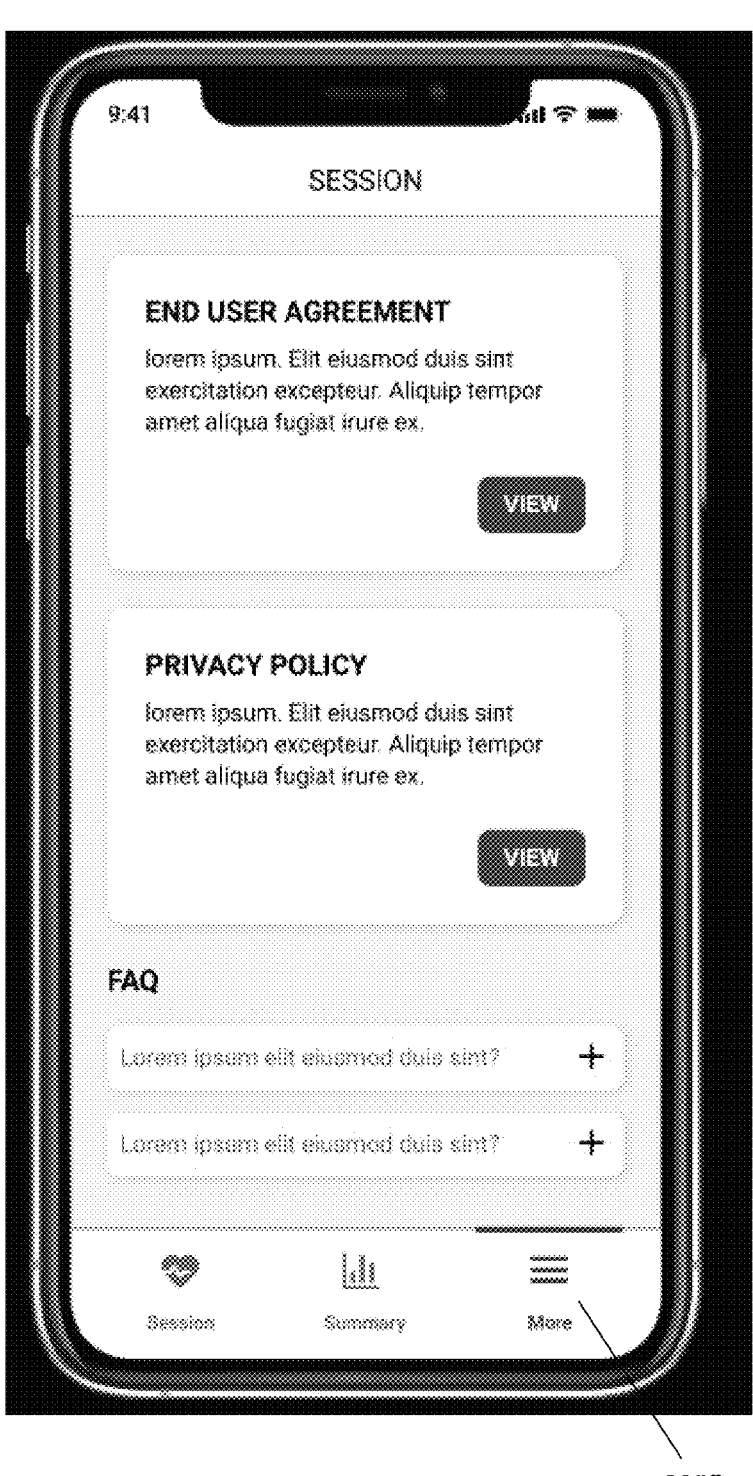
FIG. 6F                                605B

617

619

DEVICE FOR CORRELATING A BIOMETRIC VARIATION WITH AN EXTERNAL STIMULUS AND RELATED METHODS AND SYSTEMS

CROSS REFERENCE TO RELATED APPLICATIONS

The present application claims priority to U.S. Provisional Application No. 63/268,914 filed on Mar. 4, 2022, and U.S. Provisional Application No. 63/232,087 filed on Aug. 11, 2021, the contents of all of which are being incorporated herein by reference in their entirety.

FIELD

The present disclosure relates to detection of biometrics of an individual and in particular to an electronic device for correlating a biometric variation with presence and/or variation of an external stimulus, and related methods and systems.

BACKGROUND

Detection of biometrics of individuals is a growing area of interest, in particular, when directed to provide information on the health of individuals.

Despite developments in production of devices, challenges remain in detection of biometrics that can provide comprehensive information concerning the health of the individual and/or guidance for the related improvement.

SUMMARY

Provided herein are methods and systems to determine a correlation between biometrics of an individual with presence and/or absence of one or more external stimuli and related devices, which in several embodiments can be used to provide information on the status of the health of the individual in connection with the external stimuli. In one embodiment, stress reactions shown by heart rate and/or other condition parameter changes that can be caused by allergies, hypersensitivities, sensitivities, intolerances and other type of reactions can be detected by the system.

According to a first aspect, a method for correlating biometrics of an individual with a stimulus external to the individual, the method comprising using a computing device to detect a pattern between one or more external stimuli detected by a first sensor communicating with the computing device, entered into the computing device, and/or downloaded from the internet to the computing device, and one or more biological signals of the individual detected by a second sensor communicating with the computing device, entered into the computing device, and/or downloaded from the internet to the computing device, the detecting performed to provide a detected pattern; and the computing device providing an information to a user concerning the detected pattern.

In some embodiments, the information concerning the detected pattern comprises instructions for the individual to maintain, modify, or eliminate the detected pattern.

Examples of instructions include changes to diet; changes to exercise; directions to seek professional medical advice; avoidance of an object, location, substance, or class of such; suggested shopping list; and additional instructions identifiable by a skilled person.

According to a second aspect, a method for correlating biometrics of an individual with a stimulus external to the individual, the method comprising: a computing device comparing a predetermined pattern between external stimuli and biological signals, with one or more external stimuli detected by a first sensor communicating with the computing device, entered into the computing device, and/or downloaded from the internet to the computing device, and one or more biological signals of the individual detected by a second sensor communicating with the computing device, entered into the computing device, and/or downloaded from the internet to the computing device, the comparing performed to provide information about a presence or absence of the predetermined pattern.

The method further comprises providing an information concerning the presence or absence of the predetermined pattern in the individual.

In some embodiments, the information concerning the presence or absence of the predetermined pattern in the individual comprises instructions for the individual to maintain, modify, or eliminate the detected pattern.

According to a third aspect, a system is described for correlating a variation in biometrics of an individual with a stimulus external to the individual, the system comprises: an application running on a mobile device, the application configured to cause the mobile device to gather one or more biometric inputs and one or more external stimuli inputs and the display of correlations between the biological signal inputs and external stimuli inputs, and a server configured for interfacing with mobile devices over a network, the server configured to provide the application with pattern matching on the biometric inputs and the external stimuli inputs.

According to a fourth aspect, a device is described and configured to correlate one or more external stimuli detected, entered and/or downloaded from the internet, and a variation of one or more biological signals of the individual detected, entered and/or downloaded from the internet. Accordingly, the device of the disclosure is configured to obtain biological signal information from user input, direct detection and/or downloading of information from the internet, obtain external stimuli information from user input, direct detection and/or downloading of information from the internet, and perform correlation of the information derived. The device herein described can be wearable and can optionally comprise of a biometric sensor and/or an external stimuli sensor.

The devices methods and systems herein described, in several embodiments, can be used to provide information on the status of the health of the individual in connection with one or more external stimuli.

In particular, the devices methods and systems herein described can be used to determine correlations between changes in external stimulus with changes in the user's biometrics. These correlations can be analyzed with pattern matching and matched to known rules to modify the individual biometrics and/or diagnose the user's health.

The devices methods and systems herein described, in several embodiments, can be used to provide guidance on courses of action to improve the health of the individual in connection with one or more external stimuli.

The devices methods and systems herein described, in several embodiments, can be used in connection with treatment and/or prevention of a number of conditions involving an elevated heart rate (e.g., postural orthostatic tachycardia syndrome (POTS), inappropriate sinus tachycardia or IST, congestive heart failure and additional heart conditions identifiable by a skilled person).

The devices methods and systems herein described, in several embodiments, can be used in connection with improvement of well-being and/or quality of life of children, adolescents or aging individuals, including treatment and/or prevention of various conditions (e.g., heart conditions) that develop or worsen as people age.

The devices methods and systems herein described, in several embodiments, can be used in connection with improvement of performance of an individual in one or more physical exercises, such as improvement in physical strength, speed and/or endurance of an individual through detection, monitoring, modification and/or elimination of pattern between stimuli and biological signals associated thereto.

The devices methods and systems herein described can be used in connection with applications wherein information and/or guidance concerning health, wellbeing, quality of life, optimal functioning, or optimization of a health-related biomarker of an individual are desired. For example, the devices methods and systems herein described can be used to reduce stress responses to external stimuli by the individual, diagnose conditions and/or suggest therapeutic approaches and tools to treat and/or prevent a condition. Additional exemplary applications include uses of the devices methods and systems herein described in several fields including fitness, basic biology research, applied biology, biological analysis, aetiology, medical research, medical therapeutics, veterinary medicine and animal husbandry, with particular reference to diagnostic and therapeutic applications, applications to improve fitness, sleep, weight control and physical, cognitive and psychological wellbeing or performance and in additional fields identifiable by a skilled person upon reading of the present disclosure.

The details of one or more embodiments of the disclosure are set forth in the accompanying drawings and the description below. Other features, objects, and advantages will be apparent from the description and drawings, and from the claims.

BRIEF DESCRIPTION OF DRAWINGS

The accompanying drawings, which are incorporated into and constitute a part of this specification, illustrate one or more embodiments of the present disclosure and, together with the detailed description and examples sections, serve to explain the principles and implementations of the disclosure.

DETAILED DESCRIPTION

Figure 1:
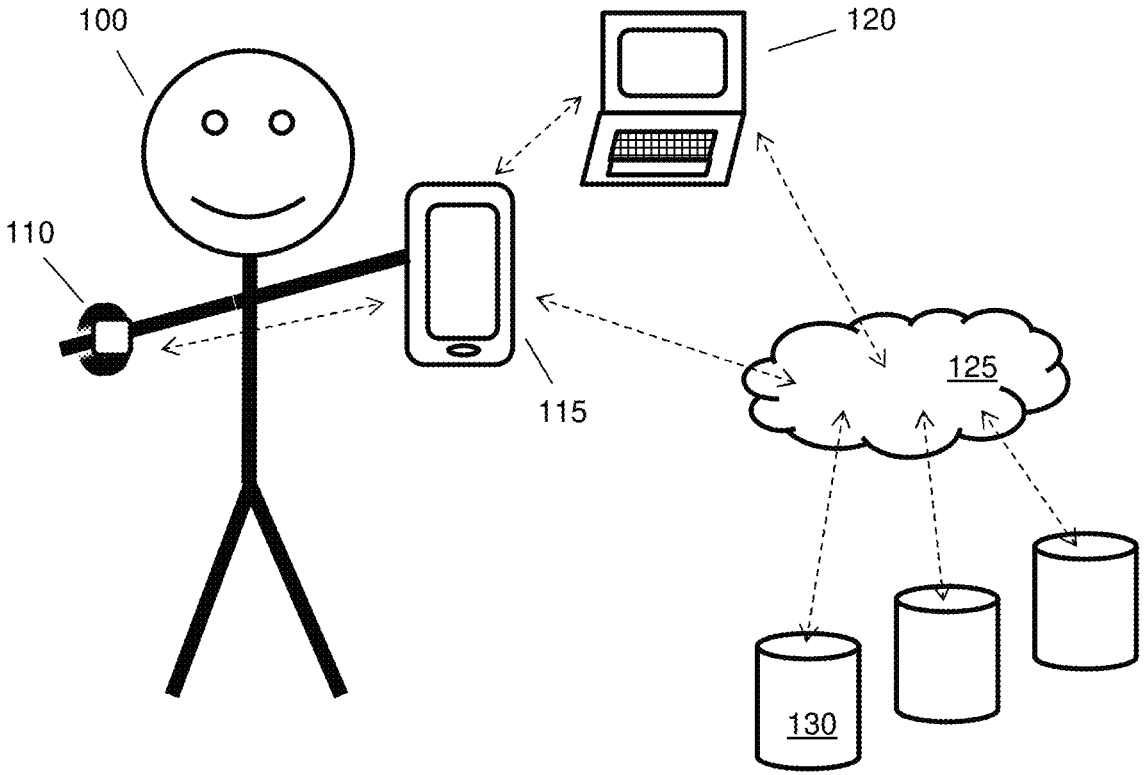
FIG. 1 shows an example system in use.

Provided herein are methods to determine a correlation between variation in biometrics of an individual with presence and/or variation of one or more external stimuli and related systems and devices.

The term "biometrics" as used herein indicate measurements of an individual's characteristics, possibly inclusive of related calculations. In particular, biometrics in the sense of the disclosure relate to distinctive, measurable biological characteristics used to label and describe individuals, herein also indicated as "biological signals" which encompass any biological feature of the individual capable of detection.

The terms "detect" or "detection" as used herein indicates the determination of the existence, presence or fact of a target item in a limited portion of space. Accordingly, detection can be performed on the individual or part thereof or on a sample, a reaction mixture. The "detect" or "detection" as used herein can comprise a determination of chemical and/or biological properties of the target item, such as ability to interact, and in a particular bind, other compounds, ability to activate another compound and additional properties identifiable by a skilled person upon reading of the present disclosure. The detection can be quantitative or qualitative. A detection is "quantitative" when it refers, relates to, or involves the measurement of quantity or amount of the target or signal (also referred as quantitation), which comprises any analysis designed to determine the amounts or proportions of the target or signal. A detection is "qualitative" when it refers, relates to, or involves identification of a quality or kind of the target or signal in terms of relative abundance to another target or signal, which is not quantified. In some embodiments, biological signals forming biometrics according to the instant disclosure can be "biomarkers" which are a detectable indicator of a biological state or condition of the individual. Biomarkers comprise molecules detectable in tissues such as blood or soft tissues or biological secretion and excretions such as urine or saliva. Biomarkers further comprise biological or chemical features of organ and/or or tissues such as pH, protein content, composition of extracellular matrix and additional features identifiable by a skilled person.

Biomarkers in the sense of the disclosure further comprises detectable physiological features associated with physiological processes of the individual, such as, temperature heart rate, skin conductance, respiratory rate and content, muscle current, brain electrical activity, electrocardiogram, pH (e.g., from urine, saliva, blood etc.), blood glucose, analysis of exhaled breath for ketones and related compounds, carbon dioxide, hydrogen and other substances, inflammatory markers in the blood, such as C-reactive protein and additional features of an individual identifiable by a skilled person.

The term "individual" as used herein in the context of the methods, systems and/or devices herein describe includes a single biological organism, such as animals, and in particular higher animals, and in particular vertebrates such as mammals, and in particular a human being. Other examples include dogs, cats, cattle, sheep, goats, pigs, chickens, geese, ducks, deer, bison, horses, mules, donkeys, mink, camels, lamas and alpacas and additional animals identifiable by a skilled person.

Accordingly, biological signals in the sense of the disclosure comprises biomarker measured and evaluated using blood, urine, breath and other secretions or various tissues, as well as physiological features such as heart rate, blood pressure and temperature, characterizing the state of the individual and in particular, characterizing the individual's health. The state of the individual's microbiome and its products might be assessed. Sequencing or culturing of the microbiome of various tissues of the individual using any methods could also be relevant in biological signals.

Features of characterizing the biological signal such as form (e.g., precursor form of a biomarker molecule), amount (e.g., quantity of a biomarker or heart rate) and/or relationship with other biological signals of the individual (e.g., co-occurrence or modifications due to co-occurrence) or impact on the health of the individual, are herein identified as features of the biological signal. The word "health" as used herein indicates a state of physical, mental and/or social well-being of the individual associated with a normal biological functioning of the individual and their parts.

Accordingly, the term "health" encompasses the absence of a medical condition and is also generally associated to a state of the individual associated with the normal biological chemical and/or physical functions of the individual or any of the individual's parts which is affected by the individual's activities as well as by stimuli external to the individual.

The term "stimulus" as used herein indicates a detectable change in the physical or chemical structure of an individual's external environment. Features of characterizing the change such as form (e.g., precursor form of an environmental compound), amount (e.g., quantity of a compound or emission) and/or relationship with other changes or with the individual (e.g., distances between two environmental compounds, or distance between an environmental compound and an individual), are herein identified as features of the stimulus. In particular, stimuli in the sense of the disclosure or stimuli external to an individual, and which can be detected, consciously or subconsciously by an individual who can then develop an appropriate reaction are what are being referred to. The reaction may be a change in biomarkers or other physiological changes, like an increase in heart rate that the person is unaware of.

In particular, the wording external stimulus as used herein encompasses external stimuli which are stimuli from the surroundings or conditions in which a person, animal, or plant lives or operates.

Exemplary external stimuli comprise any substances that enter in or become in contact with the body of the individual as well as environmental emissions as well as natural phenomenon as will be understood by a skilled person.

External stimuli in the sense of the disclosure can thus comprises edibles, intended to encompass any item configured for intake by an individual through the digestive tract, such as food, beverages, and additional items for the individual consumption identifiable by a skilled person. Exemplary edibles comprise foods, beverages, food additives, gum, drugs, snacks, mints, candies, health supplements (e.g., herbs, vitamins, minerals, and others), prescription or non-prescription medications, fruits, vegetables, meats, dairy, bread, salt, spices, and other such items.

External stimuli in the sense of the disclosure can also comprise compounds present in the environment such as allergens (a substance that can cause an allergic reaction and related IgE production or result in non-IgE-mediated immune hypersensitivity reactions), such as dust mites, pollen, cat dander, bee venom, mold, and additional substances identifiable by a skilled person, environmental chemicals such as pesticides and herbicides, heavy metals such as lead, mercury, and arsenic; air contaminants such as carbon monoxide, ozone, particulate matter (PM), volatile organics (VOCs) such as benzene, toluene; and chloroform, and second hand smoke; and persistent organic pollutants, such as the dioxins, PCBs, and DDT, and additional chemicals identifiable by a skilled person. In some contexts when describing the system described herein, the word "allergen" is used for simplicity, but any type of stimuli from a substance or exposure that can cause an adverse reaction is included, whether or not it causes an allergic reaction.

External stimuli in the sense of the disclosure can further comprise solar emissions which include visible light, infrared (IR) light, and ultraviolet (UV) light.

External stimuli in the sense of the disclosure can also comprise natural phenomena that occurs or manifests without human input, such as, changes in a body of water, biological processes in organism external to the individual, rain, snow and additional phenomenon identifiable by a skilled person.

Other external stimuli comprised substances or objects that contact the vagina such as semen, tampons, anti-yeast infection or other medications, condoms and lubricants.

Other external stimuli include products in contact with the skin such as ointments, lotions, water from swimming pools containing chemicals, fabrics used in clothing and sheets, such as polyester, cotton and silk and residue from detergents that they are washed.

Additional external stimuli include substances or objects that contact the eyes and ears, such as prescription and non-prescription medications, like ear wax removal substances, eye drops, contact lenses, eyeglasses, hearing aids, nasal cannulas for delivering oxygen.

Other external stimuli include substances or objects that touch the scalp like shampoos, conditioners, hair dyes, solutions for doing hair permanents, hats, bicycle and motorcycle helmets.

Other external stimuli include substances or objects that touch the feet or hands, including ointments, nail polish, gloves, soap, shoes, socks and slippers.

Other external stimuli include substances or objects used in the mouth such as dental appliances, toothbrushes, toothpastes, mouthwash, substances applied by the dentist or hygienist, dental floss, fillings, crowns, and bridges.

In methods, systems, and devices of the instant disclosure, one or more biological signals and one or more external stimuli are detected and then inputted and processed in the system to detect and/or recognize a pattern also in connection with applications of rules.

Accordingly, in an exemplary given embodiment a system of the disclosure will have a predetermined number of biological signal inputs and a predetermined number of external stimuli inputs, depending on the intended use and configuration limitations of the embodiment.

Examples of inputs include locations, nearby objects, pollen counts, humidity, symptoms, laboratory measurements, biometric data from subcutaneous wearable devices like continuous glucose monitors and newer monitors being developed to detect other biomarkers (e.g., biosensor necklace detecting chemicals in sweat), body weight, body composition, respiratory rate, information or measurements obtained from galvanic (resistance/conductance) detectors (e.g., galvanic skin response), thermometers (types of thermometers include mercury, alcohol, mechanical bimetal, digital, infrared, probe, resistance, resistor, humidity, thermistor, bimetallic coil, thermocouple, etc.), piezoelectric motion sensors, gyroscopes, pH sensors (that could be connected to a urinary catheter), cameras (video or still), air particle counters, photodetectors, ozone detectors, pulse (heart rate) monitor, muscle tension detectors, electroencephalogram, electrocardiogram, blood pressure monitor, others discussed in other sections of this disclosure and additional sensors identifiable by a skilled person.

As used herein, "inputs" without further qualification refers to both the external stimuli inputs and biological signal inputs.

As used herein, a "baseline" is a biological signal input measurement that is taken prior to a given stimulus or event. A baseline can also be measured after a stimulus or event. A baseline can also be taken as the lowest value before the stimulus or event (to be compared to, for example, the highest value during the stimulus or event).

As used herein, a "stress" measurement is a biological signal input measurement taken during or sometime after (for example, within 30 seconds) of a given stimulus. A stress measurement for one stimulus can be a baseline for another stimulus. The external stimulus that correlates with a stress is a "stressor".

In embodiments of the present disclosure, method and systems are described for correlating a variation in biometrics of an individual with a stimulus external to the individual who in some embodiments can be a user.

The word "correlation" as used herein indicates a mutual relationship or connection between two or more referenced items. In particular, a correlation in the sense of the disclosure refer to any statistical relationship, whether causal or not, between the two sets of referenced items, which in the present disclosure are a variation in one or more biological signals of an individual (first set of items) and one or more external stimuli (second set of items).

Correlations are useful because they can indicate a predictive relationship that can be exploited in practice. For example, an electrical utility may produce less power on a mild day based on the correlation between electricity demand and weather. In this example, there is a causal relationship, because extreme weather causes people to use more electricity for heating or cooling. However, in general, the presence of a correlation is not sufficient to infer the presence of a causal relationship (i.e., correlation does not imply causation).

In particular, a correlation in the sense of the present disclosure when used in connection with one or more biological signals and one or more external stimuli, refers to a dependency correlation which occurs if they do not satisfy a mathematical property of probabilistic independence. Accordingly, correlation in the sense of the disclosure can indicate a predictive relationship that in some instances, can be, but does not have to have a causal relationship.

As used herein, the term "user" refers to the individual controlling and reading the output of the system. A user of the methods and systems according to the instant disclosure can be the individual having the condition data taken from but in some embodiments/cases this can be a separate person (see e.g., Examples 16 (aided) and 25 (animal husbandry)).

In the embodiments herein described methods and systems of the disclosure are configured to detect a pattern correlation between one or more external stimuli and one or more biological signals of the individual and the detecting performed to provide a detected pattern.

The word "pattern" as used herein indicates a repeated or regular way in which something happens or is done. Accordingly, a pattern in the sense of the disclosure indicates a regularity in the correlation so that the elements of the pattern repeat in a predictable manner.

In particular, in embodiments, herein described in view of the correlation between detected patterns are predictive of occurrence of the one or more biological signals in the individual when the individual is exposed to the one or more external stimuli.

As used herein, the term "event" refers to an exposure of external stimuli over a period of time. For example, if the external stimuli are food, then the event would be the eating of the food (a meal). Examples of events include meals, exercise, being in a location, exposure to a substance, playing with a pet, performing an activity, taking medicine, etc.

In particular, in several embodiments the detected pattern can be predictive of the individual sensitivity to the external stimuli, which is the individual ability to react to external stimuli. In particular, sensory receptors of the individual receive the external stimuli from outside the body, as in touch receptors found in the skin or light receptors in the eye, as well as from inside the body, as in chemoreceptors and mechanoreceptors. When a stimulus is detected by a sensory receptor, it can elicit a reaction through a series of biochemical reactions which can affect one or more biological signals of the individual quantitatively or qualitatively, as will be understood by a skilled person.

Typically, a reaction by the individual resulting in a detected pattern between one or more biological signal and one or more stimuli is triggered only when the one or more external stimuli are capable of producing systemic or local biological and/or chemical responses beyond an absolute threshold.

Accordingly, in embodiments of the methods and systems of the disclosure the detected pattern is obtained correlating the one or more stimuli with the one or more biological signal detected within a detection time frame/window. As examples, the detection time frame/window could be 10 seconds, 20 seconds, 30 second, a minute or several minutes. Taking the measurement close in time to the external stimuli minimizes the problem of confounding—where the association between the external stimuli is difficult to correlate to the condition change (stress) because of intervening external stimuli.

In some embodiments, the system detects changes in biological signal inputs a long time after the external stimuli (for example, the next day) and the correlation is determined statistically after several instances show the correlation (anti-confounding by statistical analysis). Regression analysis can be used by the system to combat any confounding inputs.

In some embodiments, the detected pattern can be provided by qualitative and or quantitative detection of presence or absence of an external stimuli, and a biological signal, and/or of a variation thereof.

In some embodiments, the pattern predictive of a correlation between the one or more stimuli and the one or more biological signal can be detected by converting the data to a string of data presented in sequence and using a pattern matching algorithm such as naïve string-search algorithms, Rabin-Karp algorithm, bitap algorithm, FM-index, or others known in the art. The pattern can also be found by converting the data into signals (or keeping them signals), normalizing them together, and finding the cross-correlation (e.g., sliding dot product) between them. The pattern can also be found by storing relationships between external stimuli and stress values and counting which relationships occur the most frequently (or above a threshold frequency). Pattern matching can also be done by matching event streams (see e.g., Efficient Pattern Matching over Event Streams by Jagrati Agrawal et al. SIGMOD '08: June 2008 Pages 147-160, incorporated herein by reference in their entirety).

In some embodiments, the pattern detection can be done by machine learning, where a model is learned from known correlated inputs. The system can include a feedback system where user input can improve the model for all users. In some embodiments, the system can include feedback where it improves a model in a manner that is individual to that particular user.

In some embodiments, the detected pattern can be selected from predetermined patterns known to be occurring when a causative or other correlation exists between the one or more external stimuli and one or more biological signals.

In some of those embodiments, a predetermined pattern can be detected in the inputs by comparing a predetermined pattern between external stimuli and biological signals, with one or more external stimuli, and one or more biological signals of the individual, wherein the comparing performed to provide presence or absence of the predetermined pattern.

In all embodiments herein described, the one or more external stimuli and the one or more biological signals of the individual detected are entered manually through a UI and/or downloaded from a network or computer and/or provided to the system by one or more sensors.

In some embodiments, the external stimuli can be entered into the system manually by the user. Examples of manual entry include using the UI (user interface) of the wearable device, using the UI of the mobile device, or using the UI of the computer. This includes typing, pressing preset buttons, using a touchscreen, using a scrollbar selection, using a checkbox selection, or other UI means of data entry.

In some embodiments, the external stimuli can be entered into the system by internet download. Examples include downloading location data, weather data (temperature, humidity, pollen count, air quality, etc.), or other environmental data from a website or network server.

In some embodiments, the external stimuli can be entered into the system by direct detection. Direct detection can include sensor data taken from a sensor on the wearable device, a sensor on the mobile device, or an external sensor in communication with the system.

In some embodiments, the reaction by the individual resulting in a detected pattern can be a stress reaction, which, in the sense of the disclosure, is a response by the body perceived to be a challenge, demand and/or threat to the individual's safety. In those embodiments, the one or more external stimuli are identified as stressors, intended as a chemical or biological agent, environmental condition, or an event perceived as causing stress to the individual.

In some embodiments herein described, a stress reaction in the individual can result in the releasing of biochemical molecules, such as stress hormones, including adrenaline and cortisol, which impact various biological signals such as heart rate, muscle tone, blood pressure rises, respiratory rate, and additional signals identifiable by a skilled person.

In some embodiments, the described stress reaction resulting in a detected pattern between stimuli and biological signals can comprises inflammation.

Other events or exposures that might affect the human being or animal that may be considered as causing stress reactions are various drugs and other substances/materials delivered orally or in the following ways: nasally, inhalers and newer pulmonary delivery methods, nasogastric tube, intravenous, intrathecal, subcutaneous, intramuscular, colonic infusion or implantation, organ or tissue transplantation, surgical implantation, eye drops, ear drops, vaginal or rectal suppositories, skin patches or skin gels/ointments/lotions, more novel methods of delivery via the skin, such as iontophoresis, ultrasound, microneedles, rectal drug delivery systems including hollow-type suppositories, thermoresponsive and muco-adhesive liquid suppositories, and nanoparticulate systems incorporated into an appropriate vehicle and additional methods of delivery into the vagina including bioadhesive liposomal gel, bioadhesive mini-tablet, bioadhesive polymers or hydrophilic polymers, intravascular drug delivery to the bladder, including newer methods that enhance absorption. Other exposures include various types of radiation treatment, as used in cancer and other disorders and various types of energy sources causing effects on the body, such as ultraviolet light and ultrasound, as well as other methods known in the art such as, but not limited to, three-dimensional conformal radiation therapy, intensity-modulated radiation therapy, stereotactic radiotherapy, brachytherapy, radioimmunotherapy, proton therapy, and pulsed ultraviolet light/ultrasound. These are examples and are not meant to exclude any other possible means of introducing substances into the body.

The term "inflammation" in the sense of the disclosure indicates part of the complex biological response of body tissues to harmful stimuli, such as pathogens, damaged cells, or irritants, Inflammation in the sense of the disclosure encompasses a protective type of immune activation response involving immune cells, blood vessels, and molecular mediators. Biological signals which are impacted by inflammatory reaction can include body temperature, pain, swelling, vasodilation, fatigue, neurocognitive dysfunction, vasodilation and/or loss of function. The type and level of immune activation that occurs is not limited to the type and level of inflammation present in autoimmune diseases, such as inflammatory cell infiltrates, but includes low-grade inflammation, metabolic inflammation, and other harder-to-detect forms of inflammation or immune activation.

In some embodiments, methods and systems herein described further comprise providing information concerning the presence or absence of a detected pattern and/or a predetermined pattern detected in the individual.

In some embodiments, the information concerning the detected pattern comprises instructions for the individual to maintain, modify or eliminate the detected pattern in the individual.

In particular, in those same embodiments, a rule is applied to detected patterns to establish whether the detected pattern should be maintained modified or eliminated.

In some embodiments, detected patterns can also be used for diagnosis, treatment and/or prevention of a condition of the individual and the instructions provided to the user are associated with at least one of diagnosis, treatment and/or prevention of the condition.

The term "condition" as used herein indicates the physical status of the body of an individual, as a whole or of one or more of its parts, that does not conform to a physical status of the individual, as a whole or of one or more of its parts, that is associated with a state of physical, mental and possibly the social well-being according to medical standards. Conditions herein described include but are not limited to disorders and diseases wherein the term "disorder" indicates a condition of the living individual that is associated to a functional abnormality of the body or of any of its parts, and the term "disease" indicates a condition of the living individual that impairs normal functioning of the body or of any of its parts and is typically manifested by distinguishing signs and symptoms. Exemplary conditions include but are not limited to injuries, disabilities, disorders (including mental and physical disorders), syndromes, infections, deviant behaviors of the individual and atypical variations of structure and functions of the body of an individual or parts thereof.

The wording "associated to" as used herein with reference to two items indicates a relation between the two items such that the occurrence of a first item is accompanied by the occurrence of the second item, which includes but is not limited to a cause-effect relation and sign/symptoms-disease relation.

In the exemplary embodiments, where the reactions are indicative of inflammation conditions associated with an inflammation that can be diagnosed, treated, ameliorated or prevented comprises inflammatory bowel disease, Crohn's disease, ulcerative colitis, asthma, myasthenia gravis, Grave's disease, psoriasis, Post-Acute Sequelae of SARS CoV-2 infection, allergic diseases, asthma, hay fever, atopic dermatitis, allergic rhinitis, sinusitis, myalgic encephalomyelitis/chronic fatigue syndrome, irritable bowel syndrome, mast cell activation syndrome, inappropriate sinus tachycardia, postural orthostatic tachycardia, orthostatic intolerance, postprandial hypotension, interstitial cystitis, recurrent bladder infections, pelvic floor pain, osteoarthritis, Irritable bowel syndrome, migraines, Alzheimer's disease, cancers, chronic obstructive pulmonary disease, cardiovascular disease, stroke, acute coronary syndrome, heart failure, Kounis syndrome, bipolar disorder, depression, dysthymia, obsessive compulsive disorder, general anxiety disorder, autism spectrum disorder, attention deficit hyperactivity disorder. Attention deficit disorder, posttraumatic stress disorder, addictions, glaucoma, age-related macular degeneration, Sarcoidosis, Castleman's disease, diabetes mellitus type 2, chronic spontaneous urticaria, Systemic lupus erythematosus, multiple sclerosis, rheumatoid arthritis, Erythema nodosum, Epidermolysis bullosa acquisita, Discoid lupus erythematosus, Dermatitis herpetiformis, Dermatitis herpetiformis, Cicatricial pemphigoid, Bullous pemphigoid, Autoimmune urticaria, Autoimmune progesterone dermatitis, Autoimmune Angioedema, Alopecia Areata, Antisynthetase syndrome, Primary sclerosing cholangitis, Primary biliary cholangitis, Autoimmune hepatitis, Anti-Glomerular Basement, Postpericardiotomy syndrome, Postmyocardial infarction syndrome, Myocarditis, Diabetes mellitus type 1, Autoimmune pancreatitis, Autoimmune polyendocrine syndrome (APS) type 1, Autoimmune polyendocrine syndrome (APS) type 2[, Autoimmune polyendocrine syndrome (APS) type 3, Addison's disease, Vitiligo[,Systemic scleroderma, Psoriasis, Mucha—Habermann disease, *Pityriasis lichenoides* et *varioliformis acuta*, Pemphigus vulgaris, Morphea, Linear IgA disease, Lichen sclerosus, Lichen planus, Hidradenitis suppurativa, Gestational pemphigoid, Kawasaki disease, Behcet's disease, Raynaud's phenomenon, Eosinophilic esophagitis, Amyotrophic lateral sclerosis, Eczema, Polymyositis, Fibromyalgia, Hashimoto's encephalopathy, Guillain-Barré syndrome, Diabetes mellitus type 1, IgG4-related diseases, chronic spontaneous urticaria, COVID-19, colds, Dengue fever, malaria, chikungunya, tuberculosis, influenza, HIV/AIDS, pneumonia, cholera, infectious diarrhea, ebola, meningitis, leprosy, Zika virus infection, and/or viral hepatitis.

The term "ameliorate" as used herein indicates a modification that result in an improvement of the well-being of an otherwise healthy individual according to medical standards and/or improve the quality of life (the standard of health, comfort, and happiness experienced) of individuals with a disease and not necessarily improve the underlying disease process according to medical standards. Accordingly, in healthy or individuals with a medical condition, "ameliorate" also could mean improve the quality of life of the person or animal or it could mean there is improvement in biological signals associated with health and/or longevity or it could mean there is enhanced performance in some aspect of life or improved physical, social or psychological well-being.

The term "treatment" as used herein indicates any activity that is part of a medical care for or deals with a condition medically and/or surgically.

The term "cross-reaction" as used herein indicates an occurrence of two or more substances that are similar enough so that the body reacts to them as though they are essentially the same. In the area of immunology, the term is used when the aforementioned substances are antigens (epitopes are the specific parts of antigens structurally configured to bind to a same immunological molecule e.g., a same B cell receptor or a same antibody). In this disclosure, it is generally used in the immunological sense, however, a broader interpretation of cross-reaction is also included.

The term "prevention" as used herein indicates any activity, which reduces the burden of mortality, morbidity, or declining function from a condition in an individual. This takes place at primary, secondary and tertiary prevention levels, wherein: a) primary prevention avoids the development of a disease; b) secondary prevention activities are aimed at early disease treatment, thereby increasing opportunities for interventions to prevent progression of the disease and emergence of symptoms; and c) tertiary prevention reduces the negative impact of an already established disease by restoring function and reducing disease-related complications.

In some embodiments, the method and systems of the disclosure can be used to monitor development of the reactions optionally after corrective actions are taken according to the instructions to provide to maintain, modify and/or eliminate the detected pattern.

In those embodiments, the method can further comprise detecting further patterns between one or more external stimuli further detected, entered and/or downloaded from the internet, and one or more biological signals of the individual further detected, entered and/or downloaded from the internet; comparing further detected pattern with the rule and providing information concerning outcome of the comparison. In some embodiments, the information concerning outcome of the comparison can further comprises further instructions directed to maintain, modify or eliminate the further detected pattern.

The methods according to embodiments herein described can be performed by corresponding systems as will be understood by a skilled person.

In various embodiments of the present disclosure, at least two types of inputs are received by the system. Examples of types of inputs are external stimuli inputs and biological signals inputs.

One or more external stimuli inputs (inputs related to external stimuli such as the environmental or other external stimuli having possible effect on the user) are provided to the system. Examples of external stimuli inputs include air temperature, humidity, pollen count, geographic location, ingested food (solid or liquid) identification, inhaled medium identification (e.g., dust, vapor, etc.), sunlight exposure, drug ingestion, animal exposure (e.g., dogs, cats, etc.), items or substances in contact with the skin, eyes, or mucosal tissues, or items or substances introduced into one or more orifices of the body.

One or more biological signal inputs (inputs related to the user's physical condition) are also provided to the system. Examples of biological signal inputs include body temperature, skin galvanic response, urine pH, heart rate, blood sugar (glucose) level.

Inputs can be provided to the system by means of API input, sensor output, manual input, or downloaded from the Internet. Biological signal inputs can include downloaded lab/doctor/health report data.

In some embodiments the system also keeps track of the time and date of the inputs. The time and dates, including days of the week, can also be considered external stimuli inputs.

The inputs (external stimuli input and biological signal input) are stored on the system for processing.

In some embodiments, the system comprises a wearable device (such as a smartwatch) and a mobile device (such as a smartphone or tablet). In some embodiments, the system includes a computer (such as a laptop or desktop). In some embodiments, the system includes a server on the Internet. In some embodiments, the system comprises a software application that resides on one or more of the wearable device, the mobile device, the computer, and/or the server. The server can be a stand-alone server, a bank of servers, or a server cloud.

In some embodiments, the system takes the external stimuli inputs and uses a pattern matching algorithm to find correlations between changes or incidents (occurrences) in the input with changes in the biological signal inputs. The system can then display the correlation to the user through the wearable device and/or mobile device. In some embodiments, the algorithm includes the use of machine learning to do the pattern matching. The algorithm can be run locally on the mobile device or remotely on a server.

FIG. 1 shows an example of the system in use. A user (100) wears a wearable device (110) that takes sensor readings from the user (100). The wearable device (110) communicates with the user's mobile device (115) by a local communication like (e.g., Bluetooth) which has an app (software application) gathering and storing the external stimuli inputs and biological signal inputs. The mobile device (115) can communicate with local computers (120) and/or servers (130) on the internet (125). The communication can be done by wirelessly by WiFi or a telephone network (e.g., 5G) or it can be done by a wired network connection (e.g., ethernet cable, USB, etc.). The external stimuli inputs can come from, for examples, GPS from the mobile device (115), sensors on the wearable device (110) or mobile device (115).

Figure 2:
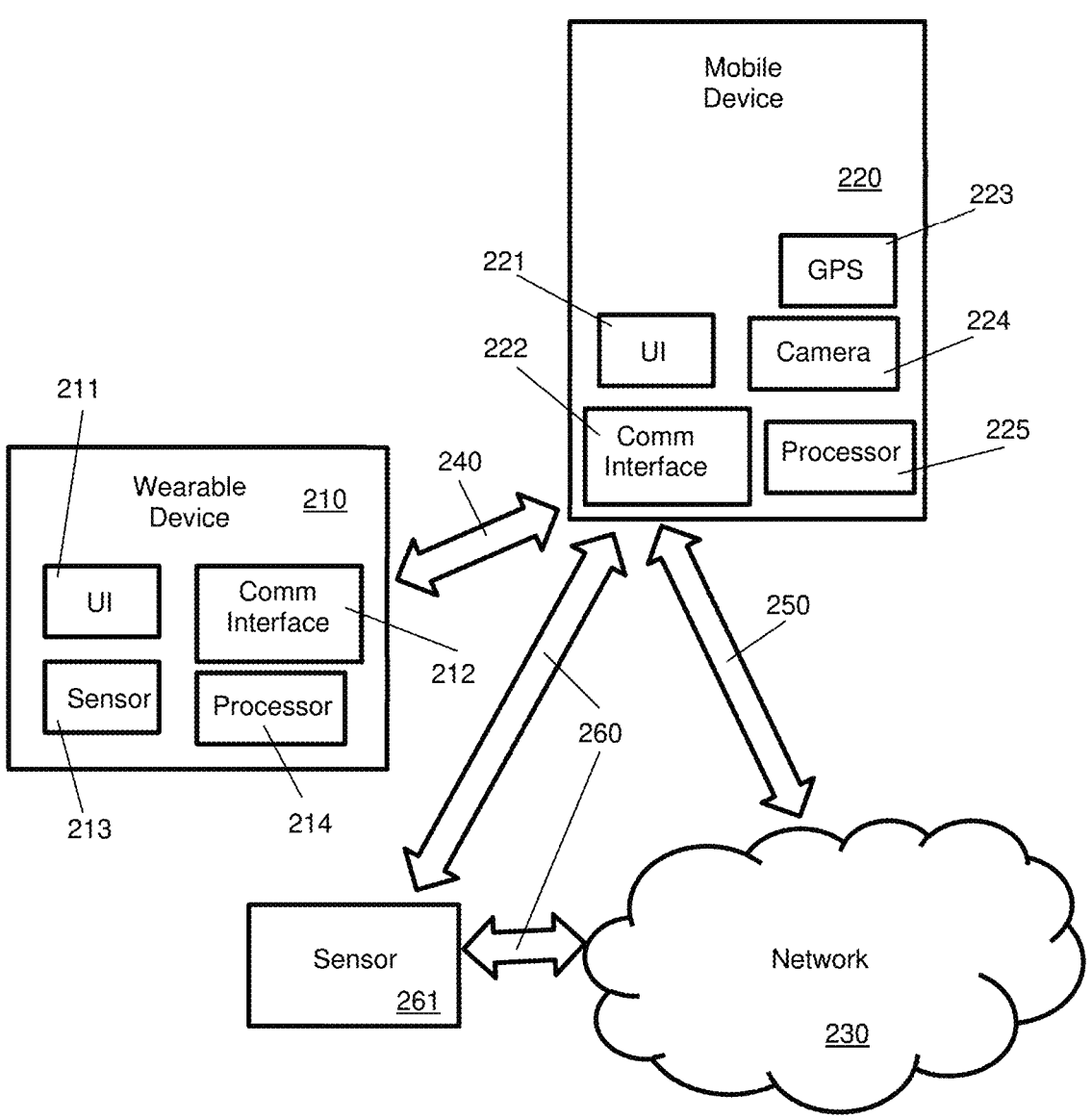
FIG. 2 shows an example of the hardware involved with the system.

FIG. 2 shows an example of structures of elements of an example of the system. A wearable device (210) can include a user interface, or "UI" (211), that allows the user to control the application, enter either external stimuli or biological signal inputs, and display results of the pattern matching. It (210) can also include one or more sensors (213) that can gather external stimuli or biological signal inputs, a processor (214) (with memory) to run the other modules, and a communication, or "comm", interface (212) to connect wirelessly (240) to the mobile device (220).

The mobile device (220) can include its own UI (221) to control the application, enter either external stimuli or biological signal inputs, and display results of the pattern matching. It (220) can also include a global positioning system, or "GPS" (223), to provide location information to the application, a camera (224) to provide certain external stimuli inputs to the application, and a processor (225) (with memory) to run the other modules. It (220) also has a comm interface (222) to enable wireless connection (250) to the wearable device (210) and external networks (230), such as WiFi and 5G data, to connect to other computers and/or servers (such as on a local network or on the Internet). The mobile device (220) or network (230) can also be connected to external sensors (251) for further external stimuli and/or biological signal inputs.

Wearable devices can also include a main circuitry housing, a means for attachment to the user (such as a strap, adhesive pad, or band), battery housing, and/or a display screen.

Mobile devices can also include a main circuitry housing, battery housing, and/or a display screen.

Wearable devices can include, as examples, electronically augmented wristbands, armbands, leg bands, watches, rings, necklaces, glasses, goggles, headgear, headbands, belts, belt accessories, belt buckles, vests, jackets, pants, adhesive pads, subdermal implants, tattoos, gloves, pouches, pockets, shoes, or other articles of clothing. They also include worn medical devices. Additional exemplary wearable devices comprise any other items wearable by a user, such as a device or sensor integrated in the fabric (e.g., using silver-coated thread, nanostructured textile electrodes, and/or various inbuilt sensors) of an item of clothing, wound dressing, bedding, a piece of furniture, or a vehicle seat, as well as additional items which can be implanted or mounted in the body of an individual.

Mobile devices can include, as examples, smartphones, tablet computers, notebook computers, personal digital assistants, portable multimedia (audio/video) devices, cameras, portable game consoles, pulse oximeters, and other hand-held electronic devices, including medical devices.

Computers can include, as examples, laptop computers, desktop computers, smart home appliances (e.g., air conditioning units, air purifiers, lights, windows, refrigeration units, washing machines, clocks, alarms, etc.), servers, routers, medical devices, smart televisions, game consoles, or other computerized machines.

In some example embodiments, the pattern matching includes matching patterns from multiple external stimuli inputs to a condition. For example, the pattern might show that a particular combination of external stimuli inputs, eating cheese (first input—ingested food type) at a specific location (second input—GPS location), is correlated to an increase in blood pressure (input condition), whereas eating cheese at other times is not.

Examples of sensors include galvanic (resistance/conductance) detectors (e.g., galvanic skin response devices such as finger electrodes, wearable GSR sensors, electrodermal screening devices, ZYTO Hand Cradle™), thermometers (Mercury, Alcohol, Mechanical Bimetal, Digital, Infrared, Probe, Resistance, Resistor, Humidity. Thermistor, bimetallic coil, thermocouple etc.), piezoelectric motion sensors, gyroscopes, pH meters (handheld or bench), pH strips or paper (litmus paper or more precise types of test strips), cameras, positioning/location devices, air particle counters, photodetectors, ozone detectors, pulse (heart rate) monitor, muscle tension detectors, electroencephalogram, electrocardiogram, blood pressure monitor, and additional sensors identifiable by a skilled person.

Rules

In some example embodiments, the system includes "rules". The rules take known information about the inputs and their correlations and provides further data to the user based on those rules. For example, if a certain condition (increased heart rate) caused by a certain external stimuli input (eating a certain food) is known to be related to an allergy to that food, the rule can notify the user of that risk.

Scoring

An overall score (e.g., a value from 1-10, a rating of "low", "average", "high", etc.) could be given whenever desired during the day that assesses the overall level of stress based on only heart rate related to meals or a combination of biological signals, and the system can present suggestions to the user about what foods or locations might be better to reduce contact with and suggest that the user employ more of whatever activities or actions the users finds to be relaxing. The system can suggest, as examples, breathing techniques, mindfulness, taking a relaxing stroll, having a lighter and perhaps earlier dinner than usual, and avoiding over stimulating activities (such as stressful encounters or high stress types of entertainment). A score can be based on an accumulation of stress levels, an average of stress levels, and/or a combination of different stress levels.

Confidence Levels

The system can use "confidence levels" in determining if a stress level is reached. This can be implemented as considering different quantitative levels of a biological signal input (such as different bpm or beats per minute difference rates giving different levels of confidence that the difference indicates stress) or by considering multiple biological signal inputs and giving a confidence level based on the number of inputs that indicate stress. The confidence level can be displayed to the user. The confidence level can also be used by the rules to determine a course of action to suggest to the user. The confidence level can also be used by the system with a setting (e.g., sensitivity level) to determine if stress is reached by comparing the confidence level with a threshold set by the setting. The confidence level can also be used with statistical analysis to differentiate false positives from true positives or giving a probability that the results are not due to chance.

Cross-Reaction Suggestions

Given an association with an external stimulus to a stress condition, the system can use rules to suggest to the user other external stimuli that have cross-reaction associations. For example, if a stress difference with almonds and pecans is determined to be high, the system can warn about other nuts and other factors that could cause similar reactions, based on data the system has on those external stimuli.

Ways to Measure

As used herein, measurements that are taken over an interval of time (such as a baseline heart rate measurement) can be calculated several different ways. For example, an average or arithmetic mean can be taken from several values measured over the interval. In some embodiments, extreme values (outliers) differing from the average by some threshold delta (difference from other values) threshold value can be excluded from the calculations. Other similar ways to calculate a mean value over the interval would be understood by one skilled in the art. A simple calculation can be taking the sum of all measured values and dividing by the number of values measured (simple average), but other algorithms known in the art can also be utilized. For example: area under the curve of a plot of the measurements, slope of increase at the start of the data or slope of decrease at the end of data, maximum slope of increase or decrease of the data, differential computation, maximum value, machine learning modelling, or some combination of algorithms.

A trend analysis can also be used to determine if the measurement is valid. For example, a calculation of an average rate taken at a beginning window of the total measurement (e.g., the first 15 seconds of a two-minute measurement) can be compared to an average rate taken at a later window. If the averages differ by more than some preset threshold value, the measurement can be flagged as possibly compromised. In some embodiments, baselines from different meals can be compared to each-other.

One alternative means to mitigate the effects of random fluctuations or other factors affecting the prior baseline would be to average the pre-event baseline measurement and the post-event baseline and use that as the baseline for calculating the increase. In some embodiments, this adjustment would only be employed if the post-event value was lower than the pre-event value. In some embodiments, the post-event value would be calculated to include the values obtained while the user was recording notes on how they felt during and after the consumption/exposure event.

In some embodiments, a known influence (such as exercise before a meal) of the baseline can be automatically compensated for, by the system. This can be either by the user entering the existence of the influence, or by the system detecting the influence by recognizing a previously measured difference in the measurements. In some embodiments, the system adjusts the measurements using statistical analysis and/or multivariate regression to "erase" the known influence.

In some embodiments, the system has an adjustable length of time for baseline measurements based on the individual (e.g., an athletic user might have a quick stabilization time while an overweight user might require a longer period for stabilization). This can be set by the user, determined automatically by the system by statistical analysis of how previous baselines stabilized, or some combination of both.

In some embodiments, the system can be adjusted for baseline measurement duration to balance between speed vs. accuracy. A "quick and rough" estimate of the measurement can be presented as an option to the user which reduces the pre- and post-meal measurement times.

A measurement that is determined to be compromised can be handled by the system in different ways. For example, in some embodiments, the system just warns the user that the measurement may be compromised and suggests to the user to restart the test. In some embodiments, the system automatically rejects the measurement and forces the user to restart the measurement.

If the user moved a food closer to their nose just before or during the baseline reading, there might be an inhalant reaction to that food. Most situations should have things on a plate far from the user's face, and so, would not be a concern to any user except those with very sensitive senses of smell (or other sensing receptors) who might start reacting to the food while getting the baseline just from inhaling it. In these cases, the user can be instructed to have the food covered when doing the baseline and then uncover it when they start eating it. In general, another reaction, like to an inhalant, may bias the baseline or the heart rate value during eating for a single test, however, it should average out over multiple tests.

An external source of heart rate change (receiving a telephone call, hot flash, loud noise, etc.) could also bias the baseline measurement or the measurements during eating. In these cases, the user can restart the test after the event no longer affects them. In some embodiments, the system can detect an unusual baseline (e.g., a threshold value over previous baselines, a "spike" in measurement data over a threshold delta value, etc.) and warn the user that the measurement might be compromised. For example, a 15% elevation in bpm that lasts between 10-15 seconds out of a two-minute baseline reading could be considered a potentially corrupted measurement (the exact values can be set by the system).

In some embodiments, the system can include an alarm (audio, visual, and/or tactile/vibration) if a measurement goes over a threshold value and/or over a threshold % increase over a baseline measurement. In some embodiments, the system can have multiple alarm levels with different responses. For example, just vibrate the device if the bpm is 20% elevated but emit a beep if 30% elevated.

The systems and methods presented here can be used to provide information to allow an alteration of the diet and other exposures (e.g., odors) to the user to reduce heart rate and other stress responses and improve autonomic nervous system balance. The knowledge of responses gained by the devices and systems presented here could lead to an increase in quality of life and in some cases, might affect the course of one or more diseases, such as cancer, dysautonomia, ADHD, autism, OCD, bipolar disorder postural orthostatic tachycardia syndrome, inappropriate sinus tachycardia, or post-traumatic stress disorder. An abnormal biological signal (e.g., heart rate elevation at rest) may be reflective of autonomic nervous system (ANS) imbalance involving abnormal sympathetic or parasympathetic nervous system activity. Food, environmental factors, and other external stimuli that induce a frequent or chronic stress response could contribute to ANS imbalance or subclinical or clinical dysautonomia. The methods and devices described herein could be applied to any condition that involves these types of imbalances or disorders or any conditions that are known to be increased by stress. These conditions include, but are not limited to psychiatric disorders, eating disorders, insomnia, hypertension, traumatic brain injury, schizophrenia, personality disorders, oppositional disorder, cancer, metabolic syndrome, and congestive heart failure.

The same type of variations and adjustments on the measurements can apply to other types of data collection and analysis besides for heart rate data. For example, if a galvanic skin response was used to assess reactions to a food or inhalant and in order to determine an average during the time the person was eating one could use the arithmetic mean or the mode or area under the curve or other methods, as was mentioned above for the heart rate data. Similarly, there can be an adjustment for prior activity or for an interruption, or methods could be applied for dealing with outliers. All these variations and others understood by persons skilled in the art are to be understood to be included in the systems and methods described herein.

In embodiments herein described, the components of the system can be provided, with suitable instructions, in order to perform the methods here disclosed. Instructions, for example, written or audio instructions on paper or electronic support such as tapes, CD-ROMs, flash drives, or by indication of a Uniform Resource Locator (URL), which contains a pdf copy of the instructions for carrying out the methods, will usually be included in the system. The system can also contain, depending on the particular method used, other packaged materials useful to perform the methods of the present disclosure.

Further details concerning the methods systems and devices, can be identified by the person skilled in the art upon reading of the present disclosure.

EXAMPLES

The methods of the disclosure and related systems and devices herein described are further illustrated in the following examples, which are provided by way of illustration and are not intended to be limiting.

In particular, the following examples illustrate exemplary methods and protocols for performing methods herein described that combine exemplary stimuli and exemplary signals. A person skilled in the art will appreciate the applicability and the necessary modifications to adapt the features described in detail in the present section to additional methods and related systems and devices according to embodiments of the present disclosure.

Example 1: Relating Heart Rate Stress with Food Intake

Heart rate often goes up with food reactions. Detecting and eliminating foods that raise heart rate typically leads to a lower resting heart rate. A lower resting heart rate is associated with reduced all-cause mortality. An embodiment of the system can be configured to find this correlation. This can involve two primary modes.

Figure 3:
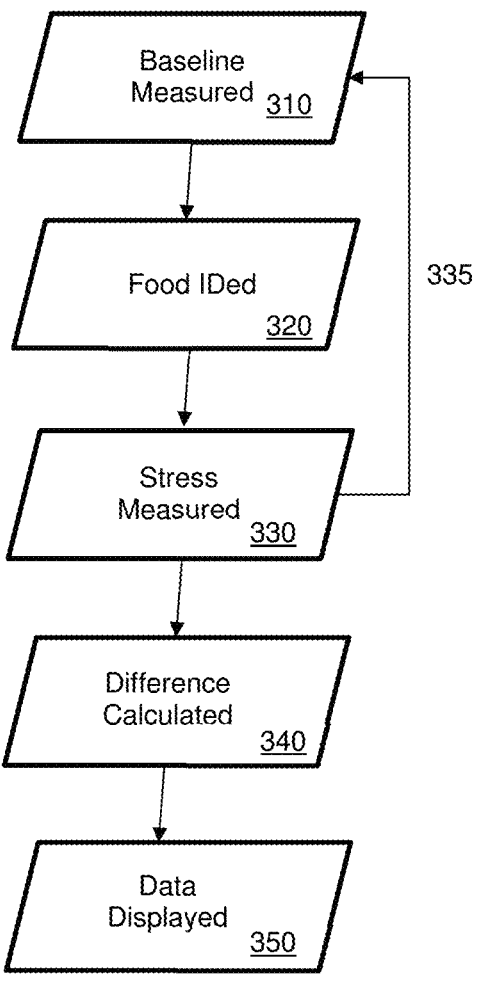
FIG. 3 shows an example of the system used to correlate heart rate with food being eaten.

In a first mode of the example, a more detailed analysis is presented on every item eaten during a meal (or as a snack). This is shown in FIG. 3.

In the first mode, the application takes snapshots (310) of the user's heart rate (e.g., pulse readings from a sensor in the wearable device) to establish a baseline rate. For example, readings of 68, 68, 70, 70, 72, and 72, for a baseline pulse of 70 bpm. The readings can be taken at regular intervals, for example every second or few seconds (as examples, every 3, 5, or 10 seconds).

Then the user inputs (320) the identification (e.g., name) of the food they are ingesting. For example, "strawberry". This input can be done on the mobile device or on the wearable device UI. For easy entry, the entry can be a selection from a common list of eaten foods (e.g., a scroll menu). A list of foods and beverages could also be provided by system for the user to choose from.

The sensor then measures the heart rate (330) as the user eats the food and for a set time after. The application then calculates a stress heart rate (aka heart rate during and/or just after eating) based on a window of time during/after the eating (for example, starting after the first 10 seconds of eating and ending about 10 seconds after finishing chewing the food). The application could also use heart rate data from the 0.5 to 20 seconds after the user finishes chewing as the stress heart rate. Start and stop times for eating the food can be manually entered by the user. Alternatively, the device can detect when the heart rate has gone up due to eating and use the heart rate during this period of elevation to determine the stress heart rate level. A stress heart rate is then calculated from these readings. For example, 90, 90, 90, 92, 92, and 92, producing a stress heart rate of 91 bpm.

The stress difference (stress heart rate minus baseline) is calculated (340) (here 21) and displayed (350) to the user. The inputs ("strawberry" and "21") are stored by the application. If the heart rate stays the same while eating as it was at baseline, the stress heart rate would be the same as the baseline and the stress difference would be 0.

After finishing the food, if the heart rate is elevated during eating, it typically declines, however, often it will be at a somewhat higher level than the baseline before the food.

So, as the user is finishing the last bits of the food the heart rate in this example might be: [88 85 80 74 73]. In the 10 seconds after finishing the previous food and before the next food the heart rate is [72 72 72 73 73 71 71] and so the new baseline would be 72.

For a meal situation, the new baseline is calculated, and a new stress heart rate is measured and calculated as above and stored. This is repeated (335) for the meal, or for a portion of the meal.

With this data, the system calculates statistics about the meal, such as which foods or beverages caused the highest increase in heart rate, what the largest difference between high heart rates is, etc.

The application can make recommendations based on the correlations showing what foods cause the highest stress difference. This can be augmented by the application of rules where the stress differences are higher than what are normally expected for that food.

The application can provide a warning to the user based on a threshold value, where the overall stress difference (sum or average of all stress differences) is higher than the threshold. The user can set the threshold, or the threshold can be part of a rule.

In a second mode, a less detailed recordation is made where the stress difference measured is over the entire meal, not just for each item in the meal. In an alternative embodiment, the application measures a subset of heart rates (e.g., top 20%). The start and stop times set by the user are the start of the meal to the end of the meal. The foods are entered into the system in any order—not necessarily the order they are eaten.

In either mode, the application can keep track of different meals at different times/days and provide indication of which foods/meals were the most problematic in terms of causing stress. The user can photograph (with the mobile device camera) each food/meal to have it memorized by the app and associated with the right date/time. The images can also be analyzed by image recognition software that is part of the application (e.g., located on a server connected to the mobile device) or separate from the application to determine food identification, thereby bypassing the need to manually enter the information by the UI.

The user can then make determinations on the basis of the multiple readings, differentiate one meal from the other in terms of different heart rate elevations and baseline increases, etc. This information can suggest to the user what foods and other exposures might need to be tested more thoroughly with the short-time frame type of tests described herein.

In either mode, the information can be presented numerically (absolute value or %, such as % increase) or as a graph. The information can be presented textually (e.g., "Low" vs. "Average" vs. "High").

Pattern matching can analyze the data over several meals to find correlations not noticeable in a single meal. For example, an increase in heart rate might not be related to a single food but might be related to a combination of foods eaten together, or to the location where the food is eaten.

Additional external stimuli inputs can be used for further pattern matching. For example, GPS/location determination can correlate where the food is eaten with the change in heart rate. In some embodiments, the location can be, by the system, associated with point-of-information (POI) provided by a database. The POI can be used to provide the user with pertinent information about the locations associated with indications of stress, such as the locations all being parks or all being fast food restaurants or the like.

Rules can be used to identify particular conditions (diseases, allergies, genetic conditions, etc.) related to the patterns and correlations found by the system.

Figure 4:
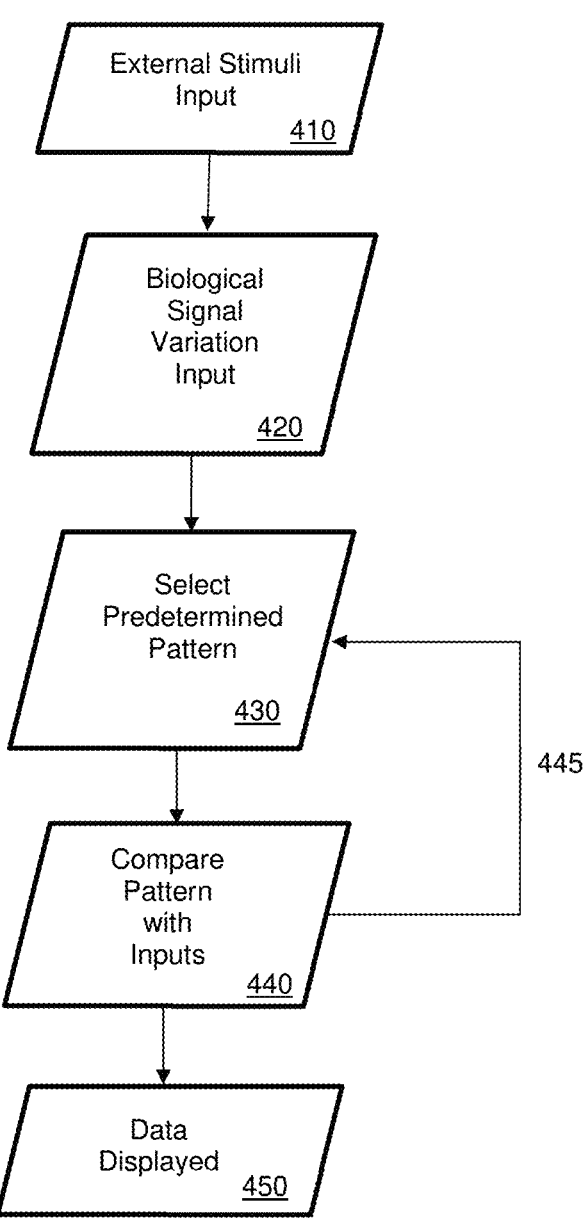
FIG. 4 shows an example of the system used to match external stimuli and biological signal variation with predetermined patterns.

FIG. 4 shows an example of the system correlating external stimuli and biological signal variation with a predetermined pattern.

The system receives one or more external stimuli as input (410) as well as one or more biological signals (420). These can be manually input, downloaded from a network, or part of sensory data. The data from the external stimuli (410) and the biological signals (420) are taken during a common time window.

A predetermined pattern (430) of the correlation between external stimuli and variations in biological signals is selected from a list of patterns (e.g., stored in memory) and then is compared (440) with the received inputs (410) and signals (420). This can be repeated (445) for all patterns in the list or, in another mode, until a match is found. The results of whether or not the patterns match or not is displayed (450) to the user. In some embodiments, further data is presented to the user related to the significance of matching a given pattern and/or suggestions on actions to take based on the matched pattern/patterns. The output can also be sent to a further device to instruct the device to change its operation based on the pattern that was matched. For example, turning on an ionizer in a room or adjusting the temperature thermostat setting of a building.

The system can also be connected to a health device, such as an air purifier, to control the health device based on the rules in the system.

Figure 5:
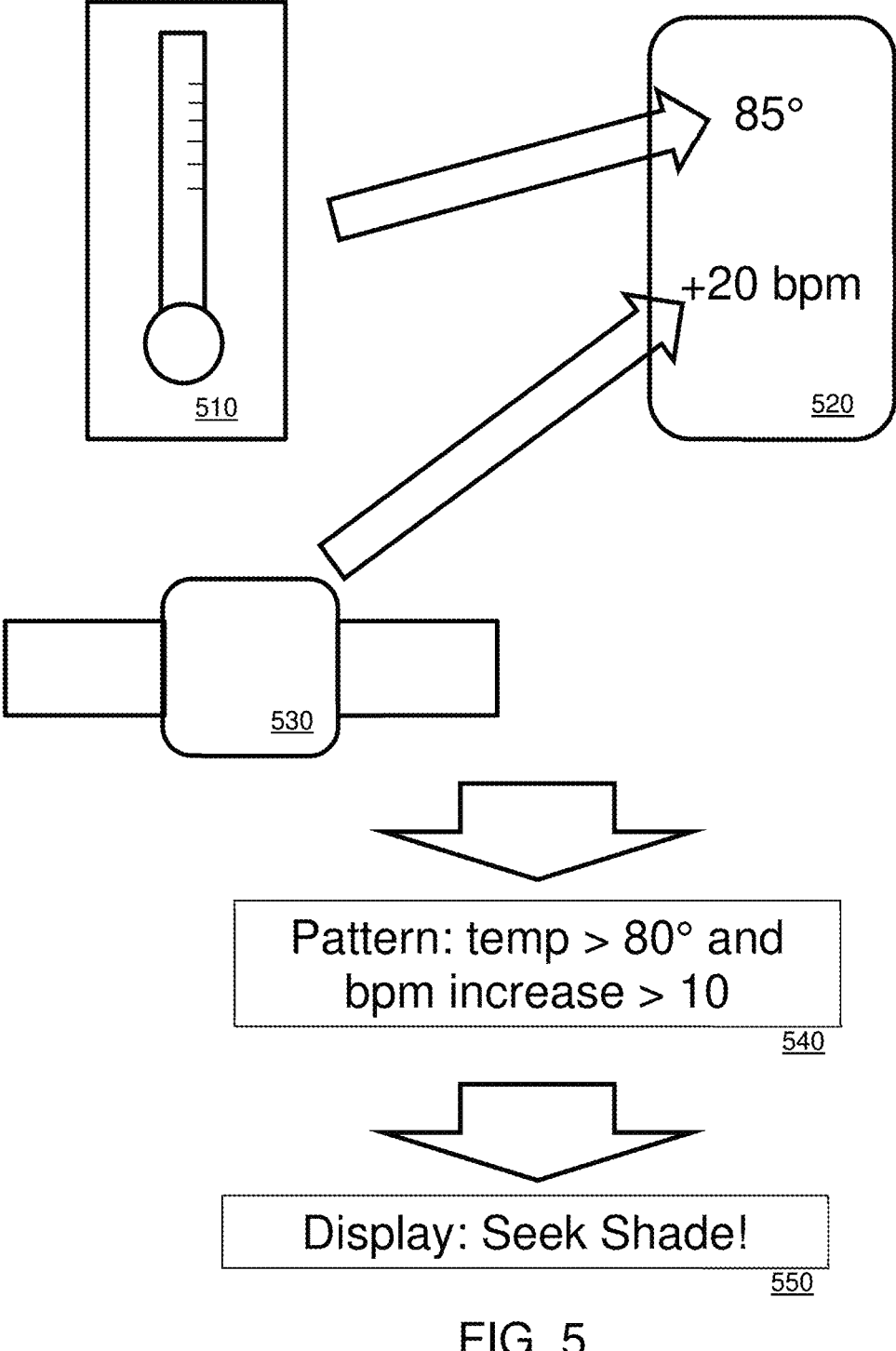
FIG. 5 shows an example of matching external stimuli and biological signal variation with predetermined patterns and displaying a suggested course of action.

FIG. 5 shows an example of pattern matching as described above. An external sensor (510) measures the environmental temperature where the user is (indoor or outdoor) and sends the data to the app on the mobile device (520). At that time, a wearable device (530) measures the user's pulse and compares to a pre-established baseline and sends the data to the mobile device (520). This external data (temperature) and biological signal variance (heart rate change) is compared to a pattern (540), either on the mobile app or at a remote server. If the inputs match the pattern (as they do here), the system displays (550) to the user (either on the wearable device or the mobile device or both) instructions to seek shade. The results of the data inputs (temperature and heart rate/heart rate change) can also be displayed.

Example 2: Reactions to Inhalants

The user can input as external stimuli various inhaled substances. For example, dust wiped from a windowsill. This can be manually input by the user through the UI, or it can be automatically determined by sensors (e.g., particle sensors). The device then measures the user's heart rate, or some other biological signal that might change due to exposure to the various substances, and determines the stress differences for each substance.

In another embodiment, perhaps combined with the first, the user can instead input locations where the inhaled substances would be located (e.g., dusty closet, pollen laden gardens, chemical cleaners in a cupboard, etc.). This can be manually input, or determined by a sensor (e.g., GPS or other signal triangulation system). The locations can then be correlated to the inhaled substances found at the given location.

Example 3: Ingredients

The user can input ingredients for some substance that they are exposed to (e.g., prepared foods, cleaning products, makeup, shampoo/soap, etc.). This can be manually entered or determined by a network look-up (user inputs the product by brand, and the system looks up the ingredients from a lookup table or internet search). In some embodiments, the user can use a barcode scanner sensor to identify the product for the system. The system can match exposure vs. stress (e.g., heart rate) and determine which specific ingredients may be causing the stress by seeing which substances cause the stress and what ingredients, if any, they have in common.

In some embodiments, the user can input symptoms during the exposure (e.g., tingling sensations, feeling tired, rash, etc.) as an indicator of stress or associated reactions, with or without other stress measurements.

Example 4: Locations and Food

There may be an interaction effect between food and the location it is consumed. The system can determine this interaction effect by recording food eaten (first external stimuli input) and the location where it is eaten (second external stimuli input) while measuring stress (e.g., heart rate) while the eating is taking place.

For example, the user consumes a meal of yogurt and a granola bar every day at lunch, but sometimes eats it in the park and sometimes eats it in the cafeteria. When the user eats it in the cafeteria, the heart rate baseline at the end of the meal goes up by 15, but when eaten in the park, the baseline goes up by 5. When user eats an apple and a granola bar in the cafeteria or the park, the heart rate only goes up by 5, suggesting that the user mainly reacts to the yogurt when eating in the cafeteria. A possible explanation could be inhaled, dairy-related allergens being present in the cafeteria that contribute to the yogurt reaction. The system detects the correlation by observing multiple instances of eating yogurt in different locations and/or multiple instances of eating various foods in the cafeteria and seeing which combinations cause the greatest stress (or cause the stress to go over a threshold). The system can present the user with a suggested action, such as "If user is going to eat dairy, eat it in the park instead of the cafeteria" or "consider reducing dairy" or "consult a physician".

Example 5: Multiple Biological Signals

The stress can be measured by multiple biological signals. For example, EEG (electroencephalogram) waves can show a reaction (e.g., delta waves averaging over 100 while consuming the item) along with a high heart rate (e.g., over 20 beats per minute increase using categories defined above), could be considered to be a reaction. The system can be absolute (indicating a positive stress reaction if both conditions are met) or relative (indicating a weak stress reaction if only one condition is met, but a strong stress reaction if both are met).

In another example of multiple biological signals, galvanic skin response (GSR), related to sweat gland production of moisture due to stress can be used with EEG measurements such that if either or both were above a certain threshold value a reaction might be recorded. However, if both were positive, the value would be recorded as being of higher confidence.

In another example of multiple biological signals, urinary pH taken 5 to 6 hours after the meal and symptom score for the time during and after the meal, could be combined with the blood glucose from the continuous glucose monitor to give greater confidence to the assessment that there was a significant reaction. The type of symptoms experienced and the location the user was in during the time after the meal would also be potentially useful pieces of information, in some cases suggesting what component of the meal was a problem.

Example 6: Long Time Frame

It could be that the location the person was in had a lot of allergens that cross-reacted with the meal components. Thus, if the person spent several hours in the kitchen, near the sink, where a lot of food-related components are present in the drain, they might have a more substantial reaction as shown by the longer-term effects of the meal (pH, symptoms, blood glucose). This might mean that the true effect of the meal was stronger than the effect indicated by the heart rate increase during and after the meal. This is because the effects of inhaled allergens from the location is added to the effect of the meal. In some embodiments, the system keeps track of the stress readings by various inputs and determines long-term correlations between the positive stress indications (and/or absence of negative stress indications) and components of the meals. The system can then provide indications to the users of the correlations and/or suggestions based on rules.

As a specific example, doing a test over 1 to several minutes of a food containing sunflower oil (which is input into the system as an external stimuli input), the user suddenly feels a headache begin and inputs that condition into the device. Also, during the same test of that food with sunflower oil, the sensors detect that the user's heart rate increases by 20 bpm. An hour later, other short-term (e.g., 0.5 to 5 minute) tests are performed at different locations in the house that are suggested to the user by the system. The only place the user's heart rate goes up in these short-term tests of inhaled substances in different locations is near a sink where the user often washes her hair. This information on the stress responses at different locations can be presented to the user. If the user notices that the food (sunflower oil) was kept above that sink, the user would know to move the food to a different location. Alternatively, the system would ask the user a question about what was kept near the sink and if it was related to some substance in the food she reacted to, and if so, suggest she might consider removing it and cleaning the area. The system could also help determine if it was the sunflower oil that the person reacted to by using short-term tests of a variety of foods to determine that there were stress reactions to all foods containing sunflower oil. Using longer-term data, the system might increase confidence to the association by finding a pattern of more headaches experienced by this user following sunflower oil/seed containing foods. A reduction in frequency and/or severity of headaches following eliminating sunflower seed/oil from the diet and cleaning the sink area and removing the sunflower oil from the sink area would provide additional long-term data supporting the validity of the pattern identified by the system.

Example 7: Immunotherapy Aid

The system can be used as an aid to monitor immunotherapy for various food allergies. For example, using oral immunotherapy to reduce peanut allergies, physicians or researchers give peanut allergic children and adults small doses of peanuts that they consume, with the levels of dosage gradually increasing over time. The system described herein can help reduce reactions that can make this immunotherapy approach difficult. During the oral immunotherapy the system can monitor the heart rate during exposures by detecting if there is a heart rate increase in the minutes or hours after ingesting the peanut and giving a warning before the user's reactions become too extreme. Specifically, if the peanut dose in the immunotherapy is given in a capsule, the heart rate could be monitored over the next 2 hours to see if the heart rate increases more than usual for that individual. The system could then advise the user and/or the caregiver, researcher or physician to reduce the amount of peanut in the capsule and/or slow the increase of the peanut doses. It might be found that an increase in the user's heart rate of 10 bpm occurring 20 to 60 minutes after the dose does not lead to a problem, but that an increase of 20 bpm 20 minutes after the dose is associated with a severe or even anaphylactic reaction the next time a dose is given. Thus, once the increase exceeds a certain level (e.g., 15), the physician, researcher or caregiver is notified to lower the dose the next time. It might be that the threshold would be different for different users.

Alternatively, the peanut sample could be tested in a short-term test in the manner an inhalant is tested as described herein by placing the peanut sample within a few inches of the user's nose for 0.3 to 5 minutes. Another option is to place a small amount of the peanut sample in the mouth and test it for a brief time (e.g., 0.1 to 1 minute) and the user can spit it out and rinse the mouth with water afterwards and spit out the water to minimize the chance of a reaction. The level of heart rate or other stress marker increase in these short-term tests could then help guide the pace of the oral immunotherapy to avoid excessive reactions during the treatment process.

Example 8: Salicylates

Salicylates can cause allergies and sensitivities. They are in many foods, but they are especially high in herbs, spices and tea. So, the system can be used via correlations and pattern analysis to determine that the user only reacts to, for example, an herbal tea with a lot of salicylates when they have been eating a lot of spicy foods that also have a lot of salicylates. Because the reactions are cumulative and depend on the amount the user has been eating from multiple sources, one embodiment of the method described herein will thus make it easier to determine the reactions in this case and similar cases where the reaction is to a substance that is found in many foods or one that cross-reacts with substances found in many foods.

Example 9: Oral Allergy Syndrome

The system can also suggest that, based on known cross-reactions, when a user reacts to a food or an inhaled substance, the user might be notified that they might react to another closely related food, or food that is known to cross-react—like foods that are often a problem in a condition called oral allergy syndrome, involving foods that are known to cross-react with pollens. This is also an issue with people who are sensitive to latex—there are a number of foods, especially fruits, that cross-react with latex, that the system can suggest the user avoid or at least evaluate for cross-reactions by various means, possibly including consulting with their physician. The system might suggest that the person could test a variety of foods that can cross-react with latex using the short-term test described herein if this is approved by their physician. Blood tests could also be suggested to detect reactions to these foods.

Example 10: Elimination Diets

The system can be used with elimination diets to track stress indications when re-introducing foods into the diet.

The system can also identify which items of food are the largest stressors as they are being re-introduced, to help adjust the diet of the user.

Example 11: Stress Index

Different biometric measurements may be combined in a variety of ways to arrive at an indication of stress ("index") in conjunction with scoring. One example is to use the sum or average of the increase in heart rate over baseline and the increase in baseline after consuming a particular item of food. For instance, it might be found that eating an apple causes the heart rate to up to 68 bpm, which is 8 bpm above a baseline of 60, but it returns to the same baseline afterwards as it was at before. So, the index would be 8. Eating peanuts causes an increase to a level of 69, however, after consuming the peanuts during the test, the new baseline is now 67. So, the index would give a score of 9 (69-60) plus 7 (67-60), or 16. This would indicate that the peanut was causing a considerably greater stress response than the apple that was not revealed adequately by only the heart rate increase occurring while eating. It might also be suggested to the user that there might be more inhalants cross-reacting with the peanuts than with the apple, possibly accounting for the increased baseline. The system can make suggestions based on data from the internet, proprietary data or previous data from the user or a model obtained from a combination of these data sources. Various biometric measurements could also be weighted differently in the calculation of the index, for instance the baseline increase could be a larger part of the final stress index than the heart rate increase during eating or vice versa.

Example 12: Acute Infection

A person has an acute infection (e.g., COVID-19). They use the system to assess edible and environmental exposures, as well as other external stimuli, that raise stress levels in the body, assessing by detecting changes in one or more stress or inflammation-related biological signals as described herein. The system minimizes confounding for many of the tests, by testing for changes where just one variable is changed (e.g., eating a food or sniffing a sample of dust) over a short time scale, such as 1 to 2 minutes. The user also repeats tests of many of the items, especially the ones that are suspected of causing a stress reaction, in order to confirm the validity of the effects. The system advises the person to consult their doctor and/or alter their diet and do other behaviors to reduce these exposures that cause stress or inflammation markers to increase during the tests. The person might also be advised to use the medical device that reduces the hypersensitivity reactions and to use it near locations and items that tend to increase their stress responses according to the aforementioned short-term tests. Over the longer-term, the items that caused a reaction can be retested and possibly will not cause a reaction once the acute infection has subsided. The reduced stress and inflammation that would result from these measures would likely increase the ability of the individual's body to fight off the infection.

Example 13: Diet Aid

A person has Type 2 diabetes mellitus and is obese and is having difficulty losing weight and exercising because of a lack of energy and willpower, which is worsened by poor sleep. A change in diet has been advised, but whenever they start to try to do that, their food cravings overpower them, and they also tend to feel more tired when they cut back on their usual diet of many highly processed foods. They can use the system to test their foods and they discover some number (e.g., three) of items that are consistently associated with an increase of 20 bpm over baseline of their heart rate. They are advised by the system to consider greatly reducing or eliminating these items after consulting with their doctor. Since they can see this dramatic increase in heart rate over just a minute or two, it makes sense to them that this is not normal, and the foods are impacting their stress and inflammation levels. When they stop these items, they do initially crave them and feel more tired, but the system informs them that it is normal to have a period of adjustment of 1 to several days (analogous to stopping a stimulant like coffee) and that this will pass. Since this makes sense to them, they continue the avoidance and begin to feel more energy after a few days, have a lower resting heart rate and sleep better. Due to this, their cravings diminish over time, and they now have the energy to exercise. They continue monitoring their stress reactions with the system and find some other items that also produce stress increases according to the biometric data (biological signal input), although only causing heart rate increases of 10 to 15 bpm. They continue to alter their diet and exposures and perhaps also use the medical device to reduce the hypersensitivities and eventually can consume many of the items, at least occasionally, without a problem. They lose weight, become more fit and their insulin resistance decreases, leading to adjustments to medications by the doctor and perhaps they even cease to need medication at some point. Other biometric measurements are detected by the system, such as blood glucose and they confirm that the reduced overall stress levels appear to be causing the same foods to cause less of a blood glucose increase as time passes. Laboratory data, such as hemoglobin A1C and C-reactive protein are input into the system (manually or automatically) to help monitor the state of the individual as well. Newer devices can be used, such as direct measurements of pro inflammatory or stress biomarkers in the blood, sweat, urine, semen, saliva or other tissues of the body to assess the changes occurring over minutes, days, weeks and months and relate them to other data collected by the system.

Example 14: Psychiatric Disorder

A user with a psychiatric disorder (e.g., bipolar disorder) can use the device to determine what edible or environmental stressors, and/or other external stimuli, might exacerbate their condition. Biometric changes, such as heart rate are monitored during several minute tests of individual foods at several meals. Two foods consistently cause heart rate increases of over 15 bpm above baseline over 2 or 3 minutes of eating them, according to the testing, and one of the foods, milk, causes the baseline to remain 10 bpm higher than the previous baseline before consuming the milk. The other food, potatoes, does not cause the baseline to change. The system uses a voice mood/stress sensor (e.g., Halo) to assess mood based on the user's voice to detect what effect the food has on their psychological state by speaking and then has their mood analysis done based on their voice in the 10 seconds after consuming each of the 2 foods. The data shows that after the milk, the analysis of their voice indicates a state of stress or of excitement or stimulation. Right after consuming the potato, the analysis of the voice indicates a state of lower mood. The user also inputs dietary information into the system as well as mood and other data regarding symptoms every day over several months of using the system. An analysis done by the system on the user's data detects a correlation between eating more potato products, as well as foods that are in the same family and contain allergens that cross-react with potato allergens (e.g., tomato, pepper) and episodes of the depressive phase of their bipolar disorder. The analysis also find that the most severe days of depression tend to follow higher consumption of these foods, thus supporting the inference from the short-term data. The analysis further reveals that there is a correlation between more milk and dairy product consumption and the manic phase of the user's bipolar disorder. The user is advised to discuss the results with their physician and the user gradually decreases these foods while being monitored by the physician and detecting and analyzing more biometric data to further monitor the effects and look for additional edible or environmental exposures, and/or other external stimuli, that impact the user's state.

Example 15: Medical Device

The system can be used with a medical device that reduces the sensitivity of a user over time. The medical device is an external device and requires an actuation that can be accomplished either by the hand or automatically. By integrating the two methods in particular settings where it is desired to reduce the hypersensitivity to various edible and environmental substances, and/or other external stimuli. It could be used in any of the examples given or the versions of the system described, in a manner that will be clear to anyone who is experienced in the art.

Example 16: Aided Use

A user may be aiding an individual that is debilitated physically or mentally and may not be capable of inputting data or making qualitative observations or testing items themselves, for instance they may be bedridden or have cognitive impairment as in Alzheimer's disease or severe autoimmune illnesses, like multiple sclerosis, amyotrophic lateral sclerosis or in myalgic encephalomyelitis/chronic fatigue syndrome. In this case, the individual inputting various data may not be the individual providing the biological signal input, but might be a caregiver, friend, family member, nurse or medical provider, or another person. For the description given here, the word caregiver will be used to include all types of persons assisting the patient. The caregiver might note the cognitive state or other signs or symptoms they detect in the patient as well as what exposures occur so as to accomplish all of the system inputs described elsewhere in this document, including in all of the specific examples.

Example 17: Stress Decrease

A user may also determine using the system described herein when a particular exposure or practice might be associated with a decrease in their stress response markers to help them in their decisions about what to do to decrease stress. The short-term data gathered over 2 to 10 minutes will be particularly useful in minimizing confounding effects. For instance, some foods might actually reduce their baseline heart rate or stress markers (e.g., an herbal tea). There are also many breathing and meditation practices the user could compare using the system: for example, whether a breathing practice involving a mantra when exhaling worked better or worse than a breathing method that involved holding the breath for 4 seconds and slowly exhaling through the mouth for 8 seconds. Many different possibilities could be included. The stress effect of walking slowly in a park vs. walking slowly on a sidewalk alongside a street could be compared by examining different biometric data mentioned herein to see if the baseline levels of particular biomarkers indicated decreased stress or inflammation associated with that activity.

Example 18: Athletic Performance Enhancement

A healthy person who wanted to increase athletic performance could use the system described herein to determine if there were any edible or environmental exposures, and/or other external stimuli, that increased their stress levels. An example would be an athlete finding that beef raise the athlete's baseline heart rate by 8 bpm and this was the highest of any of the foods. The system could advise the athlete to not eat beef when trying to maximize performance.

Example 19: Irritable Bowel Syndrome

A person with irritable bowel syndrome (or any of a variety of gastrointestinal disorders or autoimmune or inflammatory diseases), could determine what food or environmental exposure, and/or other external stimuli, increased their stress levels and combine the information with long-term symptom data to better manage their condition. Short-term tests over just a few minutes would have great benefit due to minimizing confounding.

Example 20: Hay Fever

A person with hay fever might find it difficult to identify all their triggers and to figure out if diet affects their hay fever. The systems described herein could be used to do that, combining the short-term and long-term data is especially powerful. Instructions regarding what to avoid and suggestions to contact their doctor are some of the outputs of the system, among many others, as described elsewhere in this document.

Example 21: Cancer

In cancer, there is stress from many sources, and the more stress levels and immune balance can be improved, the more likely a better quality of life and response to treatment will be attained. Short-term and long-term data gathered by the systems described throughout the examples and other descriptions can be used to enhance the patient experience and facilitate tolerance of the treatment. Medications and foods can be identified that cause stress for the individual and alterations can be considered to reduce the stress.

Example 22: Post-Infection

Post infectious conditions (such as occurring after COVID-19) have many of the same issues as described elsewhere in this document. Similar types of data can be detected that indicate stress, on the scale or minutes, days, weeks and months and the system can determine what advice can be given to the patient.

Example 23: Suggestions by System

The system can present suggestions to the user about what foods or locations it might be better to reduce contact with and suggest that the user employ more of whatever activities or actions the users find to be relaxing. The system can suggest, as examples, breathing techniques, mindfulness, taking a relaxing stroll, having a lighter and perhaps earlier dinner than usual, and avoiding over stimulating activities (such as stressful encounters or high stress types of entertainment).

Other examples of types of instructions the system can present to the user: do some testing of inhalants to figure out what might be causing a reaction or cross-reaction, perhaps including several specific ones implicated by other data (e.g., if the user reacts to a food in the detailed testing mode that is known to cross-react with a pollen, the system might suggest testing near windows of the house, furnace vent and areas known to gather dust (e.g., carpet)).

Example 24: Where and when to Use a Medical Device/Medication/Test

The use of a medical device that helps reduce reactions near certain locations or foods can be directed by the system. A certain location to use the medical device might be suggested by a symptom. For example, if the user has trouble sleeping, the system might suggest the need to test more in the bedroom. Gastrointestinal symptoms might suggest need to test and/or use the medical device in or near the bathroom.

The system can also instruct the user to test certain biomarkers, e.g., blood glucose, blood pressure, weight (to detect fluid retention) more frequently.

The system can also suggest the user consider altering medication (if it is approved by user's physician), for instance, increasing their blood pressure medication or diuretic if their doctor has instructed the user to do that sort of change under predefined circumstances, or call their doctor to ask if it should be changed.

Example 25: Alteration of Environment

The system can suggest to the user to consider having an area of their home remediated for water damage due to a reaction to mold or bacteria or in some cases even advise they temporarily vacate the room or building until the damage is repaired as a result of consistently high stress scores related to the damaged area.

The system can suggest to the user to consider replacing or sealing in plastic bags certain household chemical products (e.g., cleaning or personal care products) that cause a stress response when they are near them.

The system can suggest to the user to consider replacing or removing scented products or air fresheners.

The system can suggest to the user to consider giving their pet a different pet food, or using a different flea collar due to a stress reaction to that product being detected in their pet by heart rate changes or other biomarkers of stress or inflammation.

In animal husbandry, the system can suggest to the user to consider possibly changing some feed component, medication, additive, environmental exposure, or other external stimuli that might be identified as causing a stress response in the animal via heart rate changes closely associated with the exposure (e.g., within minutes of exposure). Greater confidence and confirmation for the change would be obtained with some longer-term data also showing positive changes from eliminating or modifying the exposure.

The system can suggest to the user to use ultraviolet-C light that is anti-microbial on areas of mold/bacterial growth that appear to cause a stress reaction if regular cleaning does not reduce/eliminate the stress response of the user to that area.

The system can suggest to the user to cover the kitchen or other drain when not using the sink or tub if the user finds a heart rate reaction when testing a sample of the area taken by rubbing something like a tissue against the area or when standing near it.

Example 26: Special Information

The system can make use of proprietary information, or proprietary information combined with information from the internet, and personal information of the user's reactions, including information about their prior reactions to certain locations and foods to give guidance to the user. Artificial intelligence or machine learning could be used to develop a predictive model for a particular user in a particular location. For instance, a home has a wood floor, and the floor has cracks between the boards that are contaminated by allergens from grapes that previously had been routinely eaten in that location. The user's data indicated that their stress reactions to grapes when they were tested using a short-term (e.g., 1-to-5-minute test) were highest when they were eaten in that location. This is one of the pieces of information that could be used in a model for that person that would be personalized. In a case in which the user did not know that someone used to eat grapes in that location, the system could derive that from the patterns of stress reactions detected. One of a variety of suggestions could be made, for instance, use of the medical device in that area or temporarily covering the area of the floor with some type of floor covering.

Example 27: Microbial Colonization/Skin Reaction

The system can be used to determine a reaction in an area of the skin and allergens from a product that might be affecting it due to microbial colonization.

For example, the user can use short-term data related to a skin reaction and confirm it with longer-term data. The next paragraph describes discovering a reaction to a currently used soap and the subsequent paragraphs discusses a potential microbial colonization involvement, and actually testing a part of the body.

A stress reaction might be detected with observation of biometric data using a test of 1 or 2 minutes as described previously when using the system near a sink where the user washes their hands. In one example, the user finds that one particular soap is also identified by the biometric data over 1 or 2 minute and the user finds that eliminating the use of the soap decreases the user's hand eczema.

In another example, a user does not find that the currently used soap causes any stress reaction using the various biometrics tested over a period of several minutes. And stopping that soap provides longer-term data that it is not the currently used soap that is the problem because the hands do not improve. However, a soap that the user had used for years, but had stopped using several years before, does cause a stress reaction as indicated in a test of 1- or 2-minutes duration, when testing the soap near the sink. At the same time as the test of the previously used soap is occurring, the user feels a tingly sensation in their hands, and they input this qualitative data into the system.

The user also rubs a piece of facial tissue against the hands and puts the tissue near their nose and finds there is a stress response revealed by the biometric data (e.g., the heart rate) that does not occur when testing a fresh piece of facial tissue (a control test), but the stress response to the test of the hands is only detected when the user is near that sink, not when in the living room or bedroom. This is because there needs to be enough of the substance to cross a certain threshold for the stress reaction to be detectable. The combination of the allergens in the air of the bathroom when added to the allergens on the sample on the facial tissue rubbed on the skin is enough to cross that detection threshold. The user receives the suggestions from the system to use the medical device near the sink and the piece of previously used soap that they had a stress response to and afterwards, to cover the sink drain and clean the sink thoroughly.

After using the medical device in that way several times on the next few days and continuing to keep the sink very clean and the drain covered, the system using the short-term, 1- or 2-minute tests no longer reveals a stress reaction to the soap, the sink or the hands. Also, it is found that the hand eczema clears up over several weeks as shown by the longer-term data input by the user. It may be that some microbial or other allergen from the soap has persisted in the skin of the hands and was present in the sink and was causing the continuing reactions.

Example 28: Short-Time Frame Tests Combined With Longer-term Patterns

In some embodiments herein the interpretation of longer time frame data is informed by the short time frame (e.g., 0.3 to 15 minutes) tests, using the short-term tests to gain greater knowledge about how various symptoms and other biological signals relate to a particular exposure. This will allow the user to make better sense of their day-to-day and longer-term changes in symptoms and likely lead to many benefits, including benefits in medical research. Conversely, a longer time frame change may give a clue to the user that a particular food or substance should be tested using the short time-frame tests.

For example, consider a user with joint pain (e.g., rheumatoid arthritis) that varies greatly in intensity. The user notes any changes in his pain and enters the information into the system. He notices that the pain and his baseline resting heart rate as measured by the system is increasing gradually over a particular week. He has gone on a holiday at this time and many things have changed in his habits, exposures and diet. He realizes he has been eating more bread, butter, beef, and corn, and has been staying in a building that contains one room that has water damage. The user uses the short-time frame method discussed herein to test these things and finds that the heart rate during eating the corn goes up 15 bpm above baseline but goes up less than 5 bpm for the other foods. He finds no heart rate change when doing a 5-minute test in the water damaged room and thus decides he does not need to change hotels, but stops eating corn and the joint pain improves in the next few days as shown in the longer-term data he inputs into the system.

One could envision numerous combinations of exposures and symptoms such as this. The changes might occur on a daily, weekly, biweekly, monthly or even yearly time scale. The user might have numerous ideas as to what changes in exposures were possibly causing these changing biological signals but with the system provided herein, the user now has a way to confirm which exposure is responsible for the longer-term changes by using the short-term tests. The data on food along with stress reaction data on multiple times scales in the system, allows correlation analysis and pattern recognition methods to provide very useful advice and suggestions. If the biological signal, like joint pain returns (likely at a lower level and/or frequency), it might be that another exposure is contributing to the pain, so the user could be instructed to do short-term tests again on food, environmental substances, and/or other external stimuli to look for additional triggers.

Another example is headaches (e.g., migraines), which have been connected to food reactions and there are many potential triggers, which might be detected by the heart rate tests on a short-term basis. Similar to the case of the joint pain, the longer-term monitoring could confirm the results of the short-term tests. Often there are more than 1 trigger food or substance suspected. If 30 foods are suspected and 4 foods are the trigger, it is very difficult to determine which foods contribute without a test such as the one described here. The role of food hypersensitivities and intolerances in producing symptoms can be especially difficult to detect because often the effects on symptoms are delayed.

Example 29: Remote Patient Monitoring in a Home or Facility

The system can be used when caring for a person who is not able to follow instructions or input data into the system. An example is a person with dementia who is being cared for at home. A caregiver, as defined above, could make the day-to-day observations that are input into the system and add laboratory values and make sure that the wearable device was being worn and was operating. Short-term tests could be performed, with the caregiver providing the foods or other items and putting in necessary inputs into the system for these tests. In another example, when the caregiver who was responsible for the use of the system is not with the user all the time, for instance, when at work, the system could include a component of monitoring that could track the monitored individual's activities. For example, a gyroscope or other method could detect movements of the hand associated with eating or drinking or a video camera could observe the activities of the individual. When the heart rate or other stress marker (e.g., heart rate) was elevated, for instance at noon, the caregiver could review the data from the gyroscope or other movement detector or video camera and could determine what activity was occurring at the time of the stress reaction (e.g., time frame of 0.3 to 15 minutes). Alternatively, the caregiver could be given a real time alert and be immediately shown by the system the portion of the video associated with the increased stress reaction or be notified of what the likely activity was associated with the increase (e.g., eating). The caregiver would know what foods were available to the individual or could find out what they had eaten when the caregiver arrived later in the day, and this would provide some candidate foods to test in more detail later with short-term tests when the caregiver could be present to aid in conducting the tests.

Example 30: Use in Medical Research

The device could be used in many research settings such as clinical trials that parallel the examples above. Some subjects in the trials could be given the system and others could be given a control intervention in a randomized manner to determine the outcome of the intervention with the system described herein. There have been some studies examining the role of diet in many conditions and the role of food reactions could be assessed. In rheumatic diseases, some studies have indicated a vegetarian or vegan diet can be beneficial. The system described herein could determine whether at least some of the animal products eliminate by these patients were causing stress responses. A study was done by the NIH showing that an ultra-processed food diet led to greater weight gain in a randomized controlled trial of in-patients due to those on the ultra-processed food diet overeating carbohydrates. Short-term tests as described herein could be used to determine if one or more of the processed food items caused a stress reaction.

Example 31: Use of a Real Time Alert

There are situations where an individual would want to be especially careful about consuming a food that causes a stress reaction. In these cases, the system could be configured to give an alert while eating to notify the user when the heart rate or some other measure of stress exceeds some threshold value that could be set by the user. It could have levels of alert, such as vibrating if above an elevation of 80, soft beeping if staying above 90, and loud beeping if staying above 100. It could be programmed to ignore very transient increases since they are likely artifacts (e.g., a 2 second increase to 106 that comes down to 70 immediately afterwards).

Circumstances that might make this feature especially valuable would include users who were especially affected by stress responses, such as those with severe allergies or severe autoimmune or other inflammatory conditions. On the other end of the spectrum, users who were highly focused on performing at the top of their abilities, such as competitive athletes or a businessperson with a demanding schedule, might want to be notified when a reaction is strong and then they would have the option to eat less of the food they were eating and eat something else that did not cause a stress reaction.

Example 32: Evaluating Reactions to Medications/Supplements

Some users are on many medications and/or supplements. Reactions do not necessarily occur immediately once they are begun but might develop over time. Stopping medications and/or supplements and evaluating reactions to them can be time consuming and difficult. In this case, the short-term test could be used either by testing the medication and/or supplements as an inhalant and putting it near the nose for the test. Alternatively, if it does not irritate the mouth, a small amount of the medication and/or supplement could be placed in the mouth either alone or combined with another substance that is unlikely to cause a reaction, such as water (e.g., a quarter tsp of water), in order to test for a stress reaction to the medication and/or supplement. If testing the medication and/or supplement when combined with another substance, then another test can be done with that substance without anything added to it as a control to compare with the substance with the medication and/or supplement added to it. In each case, as described previously, the baseline level would be obtained and compared to the level during this short-term test to detect any stress reaction that might be associated with them. Although this would not detect all types of problems with supplements and/or medications it could suggest some that may be causing problems. Then longer-term data input or otherwise obtained by the system could be used to confirm the relationship by pattern analysis. Retesting using the short-term test could monitor the reaction over time.

Other methods described in other examples with regard to detecting cross-reactions and the role of locations and inhalants might be used to allow the system to determine if there was some cross-reaction that was contributing to the reaction. Addressing the cross-reaction might even possibly allow the medication and/or supplement to be resumed. For example, the medication might have a cross-reaction with some component of a food due to a similar molecular structure (epitope). It might be that a cross-reaction could be identified, and by stopping or reducing the food, the user would be able to tolerate the medication.

Example 33: Testing Cross-Reactions

Short-term tests can be performed with methods and systems herein described which are focused on identifying cross-reactions. In this example, a related approach is illustrated in connection with the cross-reaction of allergens in connection with the related features. A skilled person will be able to identify variations of the approach applied to other stimuli upon reading of the disclosure.

When testing cross-reactions of allergens, it is expected that if different sources of an allergen are cumulative in their effects and the two allergens cross-react, then having more of allergens near the user would cause a greater reaction.

Accordingly, cross-reaction between a first allergen and a second allergen can be detected by:

detecting a first pattern between the first allergen and one or more biological signal of the individual, detecting a second pattern between the second allergen and the one or more biological signal of the individual, detecting a third pattern between the first allergen in combination with the second allergen and the one or more biological signal of the individual, and determining cross-reactivity by comparing the first pattern, the second pattern and the third pattern, wherein cross-reactivity is determined when the one or more biological signal within the third pattern are quantitatively different from the sum of the one or more biological signal of the first pattern and the second pattern, and/or when features of the first allergen and/or the second allergen affect qualitative and/or quantitative detection of the third pattern.

Accordingly, if, for example, a first inhalant and a second inhalant cross-react, then, it is expected that the related cross-reactivity can be detected through a comparison of a given biological signal detected in connection with both of them.

Additionally, the features of the inhalants, such as the proximity of the first inhalant to the second inhalant and/or to the individual, can affect the level or ability to detect a reaction to the second inhalant because of the difference in the corresponding associated biological signal (e.g., heart rate), as will be understood by a skilled person.

Quantitative detection of the biological signal detected (e.g., heart rate increase) can be based on the distance the inhalants are from the nose of an individual; the distance to cause a detectable reaction is another measure of the strength of a reaction.

Accordingly, determination of a ranking in potency of an inhalant can be performed taking into account those features. In particular, if a substance being tested can cause a stress reaction when 6 inches from the nose, it is expected that it is a more potent source than an allergen that needs to be 1 inch from the nose of an individual for a stress reaction to be detected.

Additionally, the relationship between the features of the inhalants in connection with eliciting a pattern with one or more stimuli can also be used to determine cross-reactivity. In particular, if the presence of one inhalant 3 inches from face of a human being affects the distance a second inhalant needs to be from the nose to elicit a biological signal within a pattern detectable with methods and systems of the disclosure (e.g., associated to a stress reaction), then the 2 inhalants potentially cross-react. This can be determined by doing several tests involving the two inhalants being at different distances from the nose.

Example 34: Activation of Allergens

In some embodiments, the user can have saliva or heat applied ("activation"), or some chemical like an enzyme that changes a substance as occurs during digestion to the suspected external stimuli (e.g., allergens) in order to elicit a greater response during testing. Other types of activation, transformation or production of substances, such as those resulting from microbial activity is included. Simply leaving a substance at room temperature for a period of time, rather than refrigerating it, is an example of something that would enhance such microbial activity. The tests can include repeating the test with and without the activation.

Example 35: Mobile Device App System and User Interface

Figure 6A:
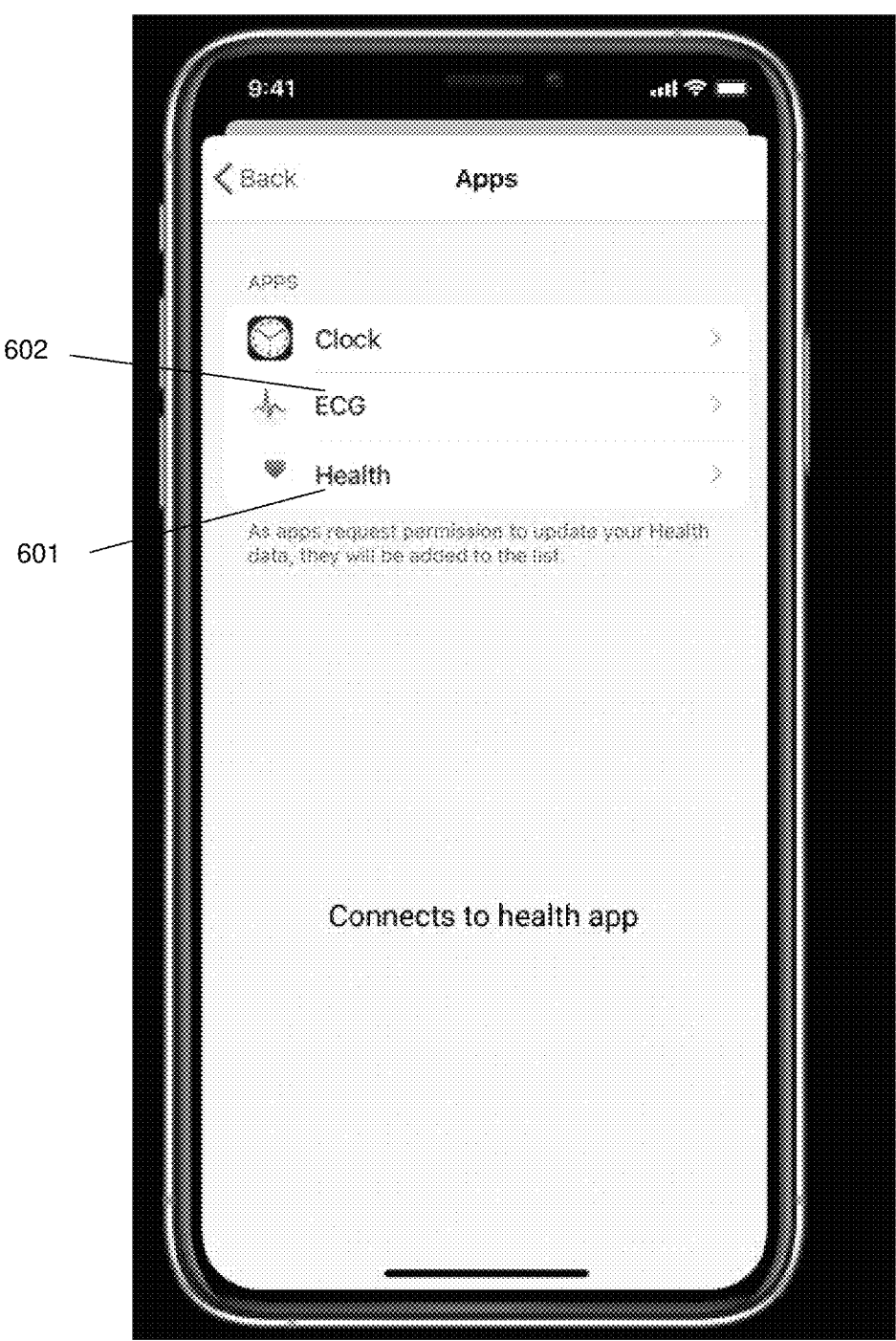
FIGS. 6A-6R show example screens for a mobile application user interface for an example system in use.
Figure 6B:
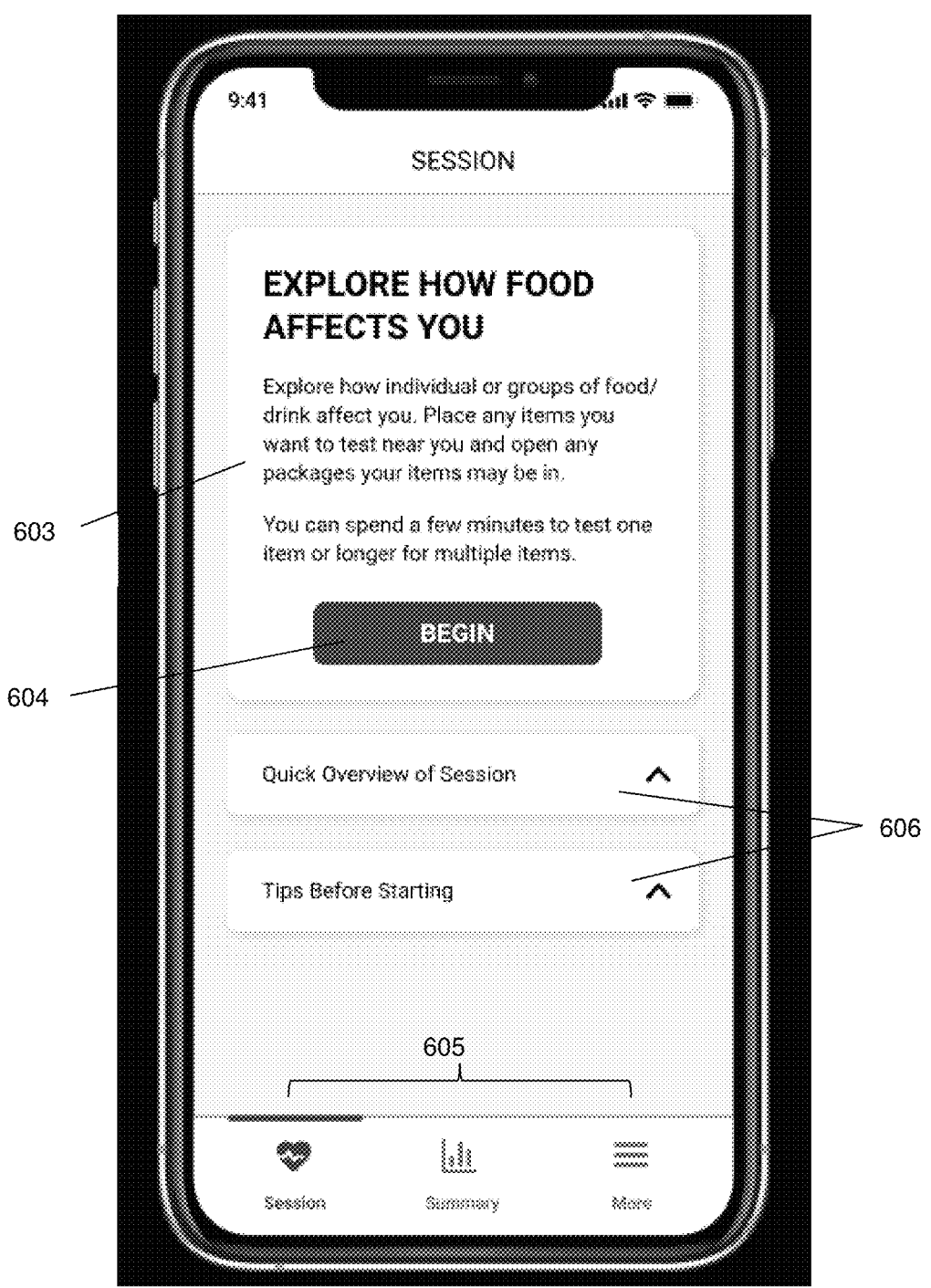
Figure 6C:
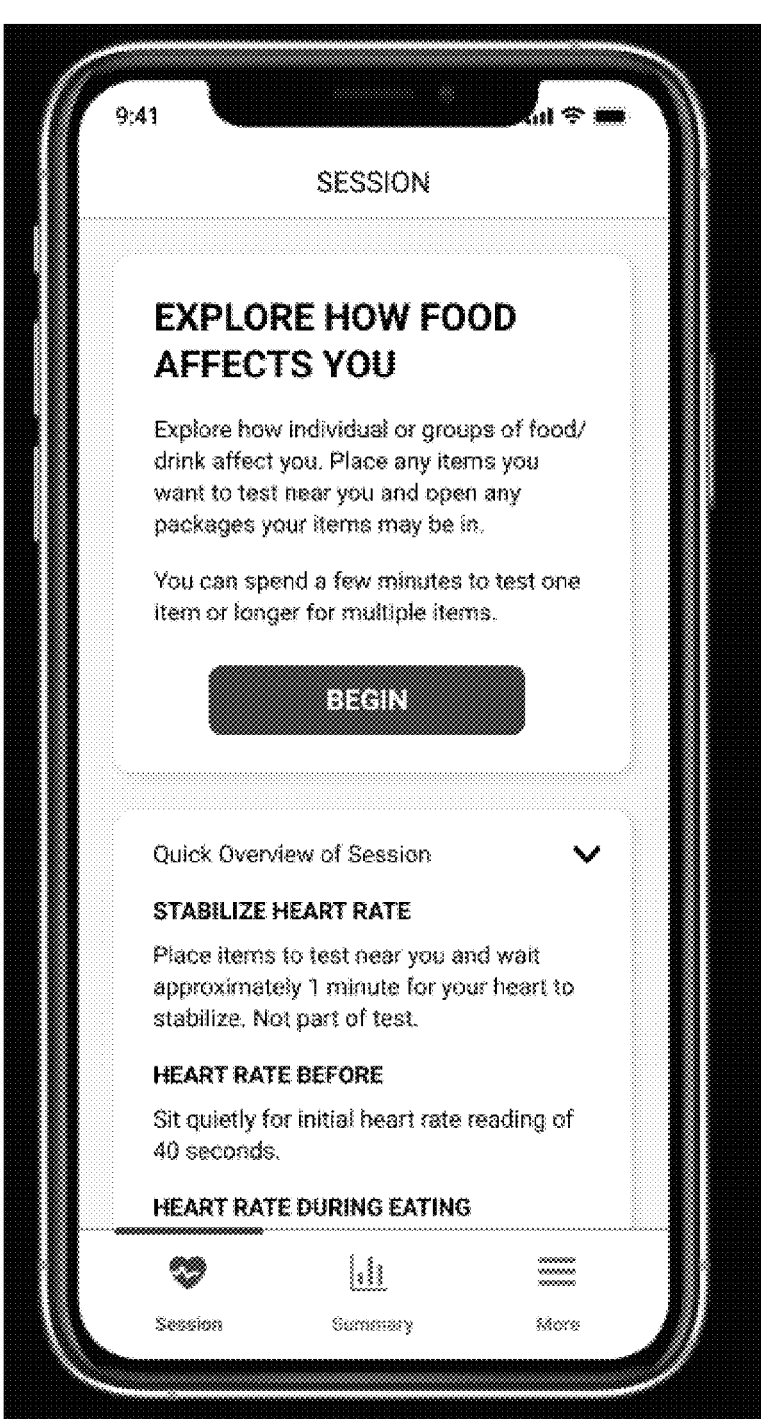
Figure 6D:
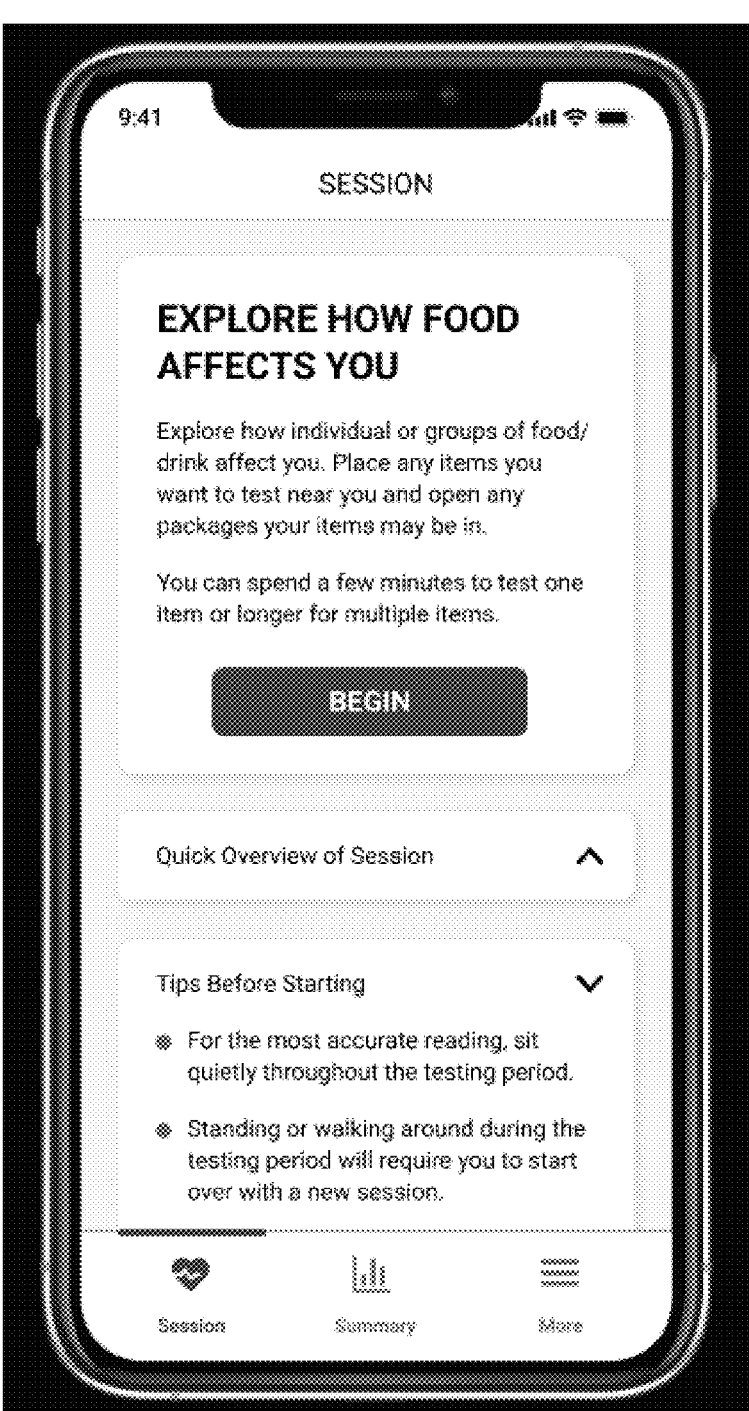

In some embodiments, a computer application ("app") on a mobile device (e.g., smartphone, tablet, etc.) can be used in conjunction with a sensor device (for example, on a wearable device such as a smart watch) to implement the system for testing reactions. As shown in FIG. 6A, the application (601) can be tied together with other applications (602) such that they share health information, either in a common database or updating each-other's databases. Upon selecting the app, a screen can be shown with explanatory text (603), a starting button (604), and menu buttons (605) such as "session", "summary", and "more". Additionally, some extra information (606) can be provided. The extra information (605) can include a quick overview of how the system will work (FIG. 6C) and some tips for using (FIG. 6D).

Figure 6E:
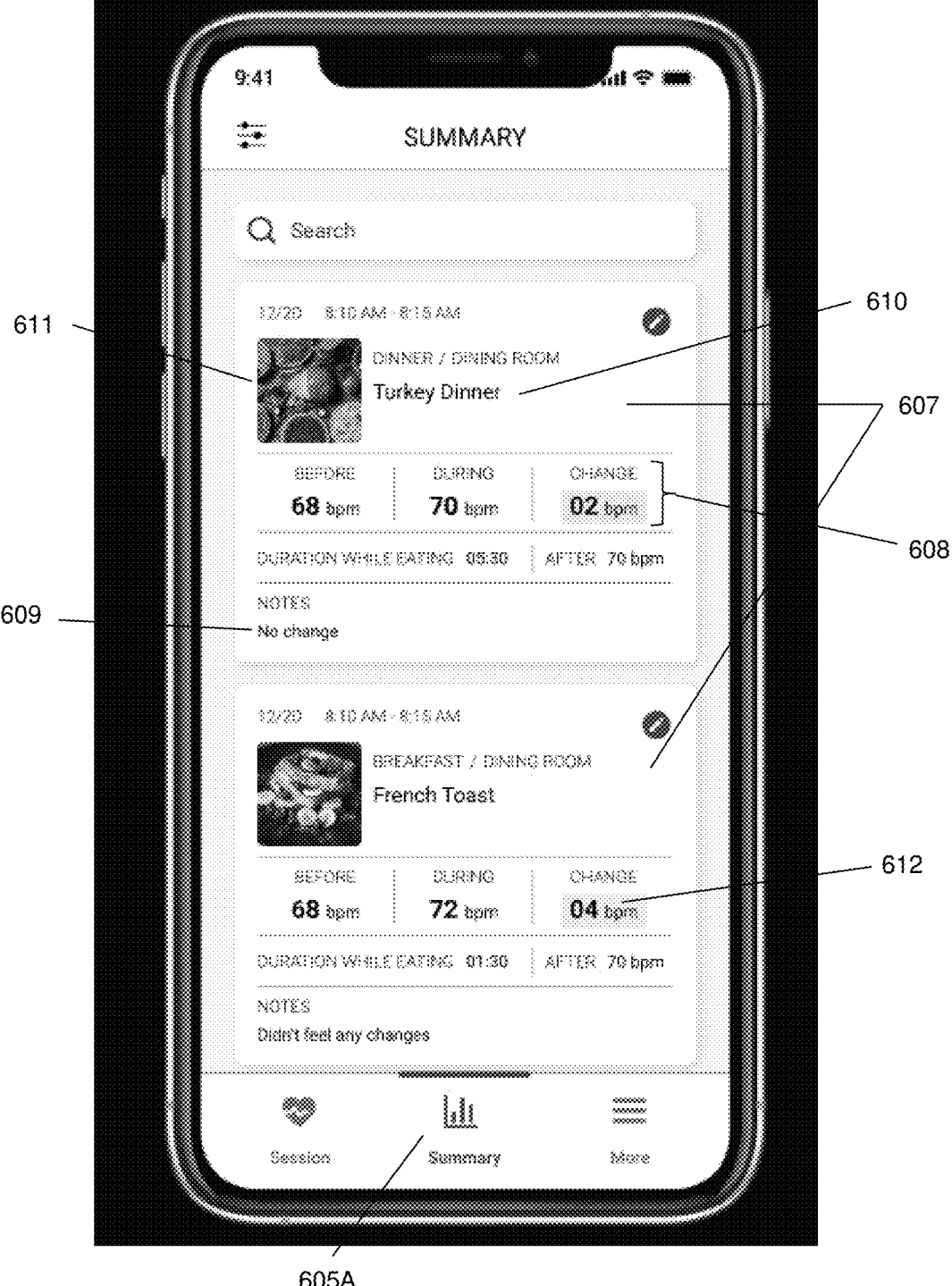

FIG. 6E shows an example of the "summary" (605A) menu option interface. When "summary" is pressed, it displays summaries (607) of each meal, which can include the resulting readings data (608), notes made by the user (609), and a description of the meal (610), possibly including a photo (611) of the meal taken with the mobile device. The change in bpm can be shown with different highlighting (612, e.g., different colors of highlights, text, or outline) depending on how the value compares to different threshold values.

FIG. 6F shows an example of a user interface when the "more" button (605B) button is pressed. The page shows additional information for the user, such as an end user agreement, a privacy policy, a list of frequently asked questions (FAQ), and the like.

Figure 6G:
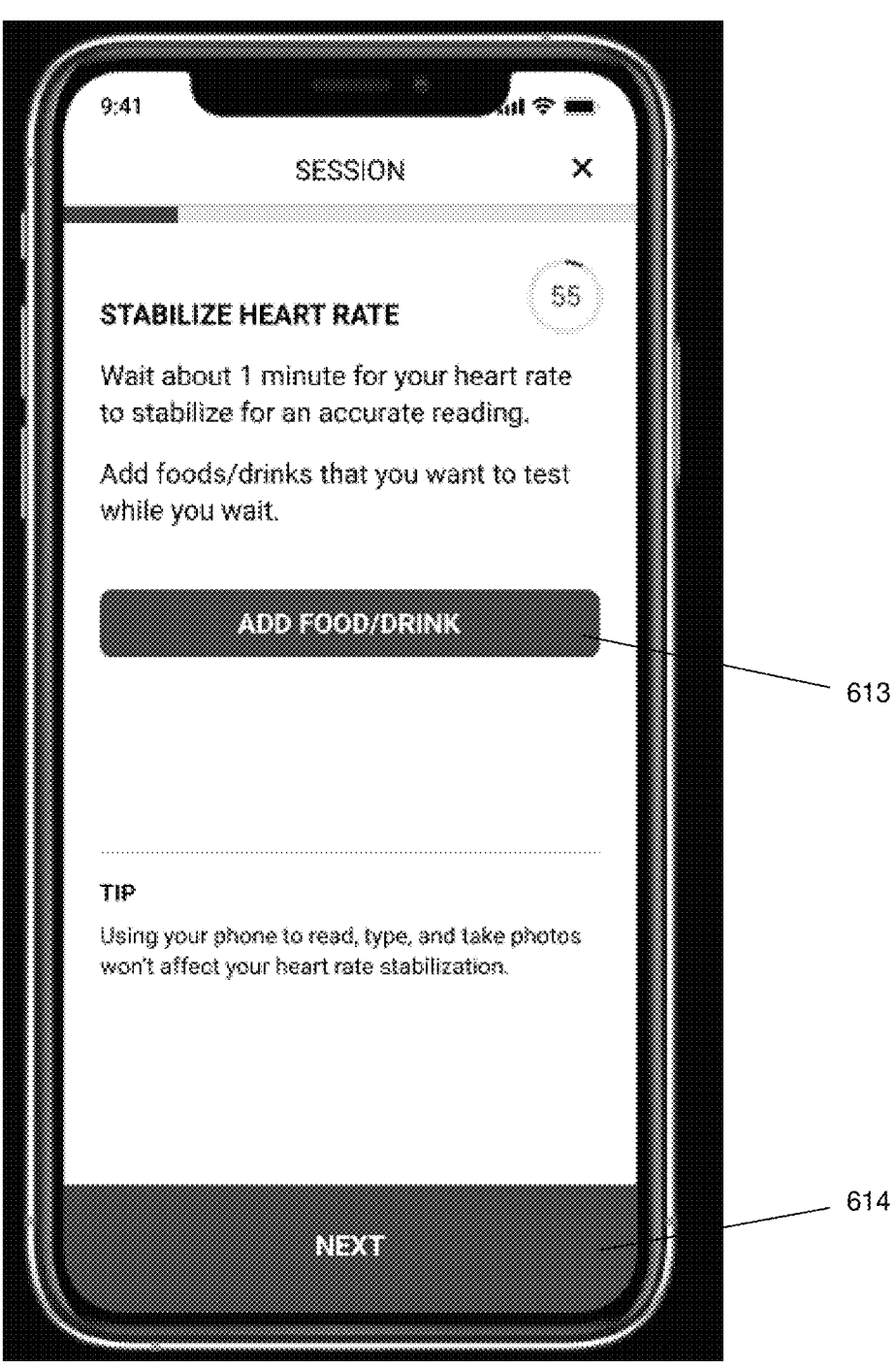

FIG. 6G shows an example of a user interface for entry of food/drink prior to eating. Foods can be entered (button 613) multiple times and when all the foods/drinks of the meal are entered, the session can be started (button 614).

Figure 6H:
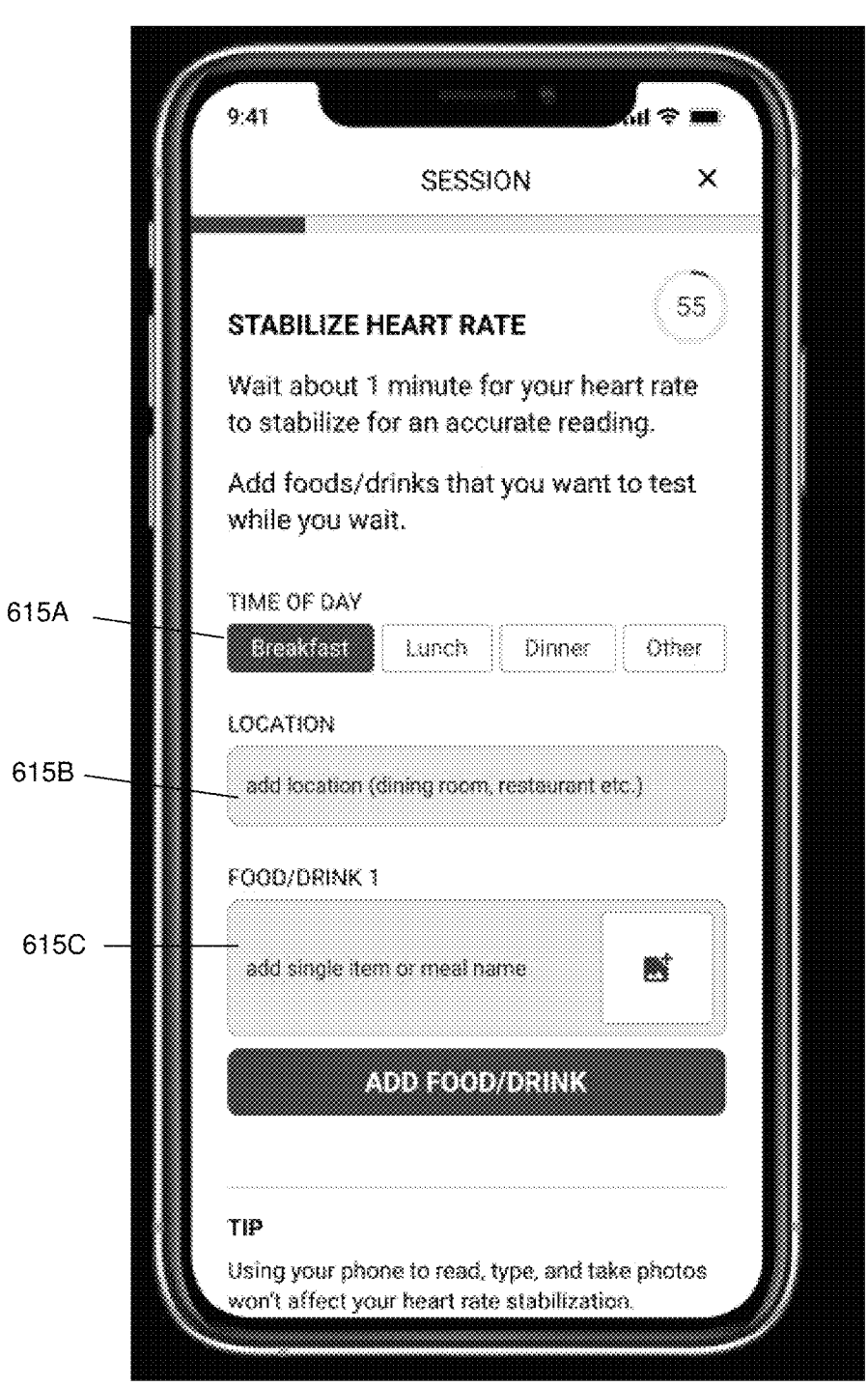

FIG. 6H shows an example of a user interface showing an interface for entering a food/drink. Data entered can include what time the meal is eaten (615A), what location the meal is eaten in (615B), and what the food/drink is (615C). These can be entered as text or be presented as a list of selections for the user to pick from. The time (615A) can be prompted to be entered in any format (e.g., time can be entered as an absolute time—e.g., 8:15 AM; as a meal description—e.g., breakfast; or as a general time of day—e.g., morning).

Figure 6I:
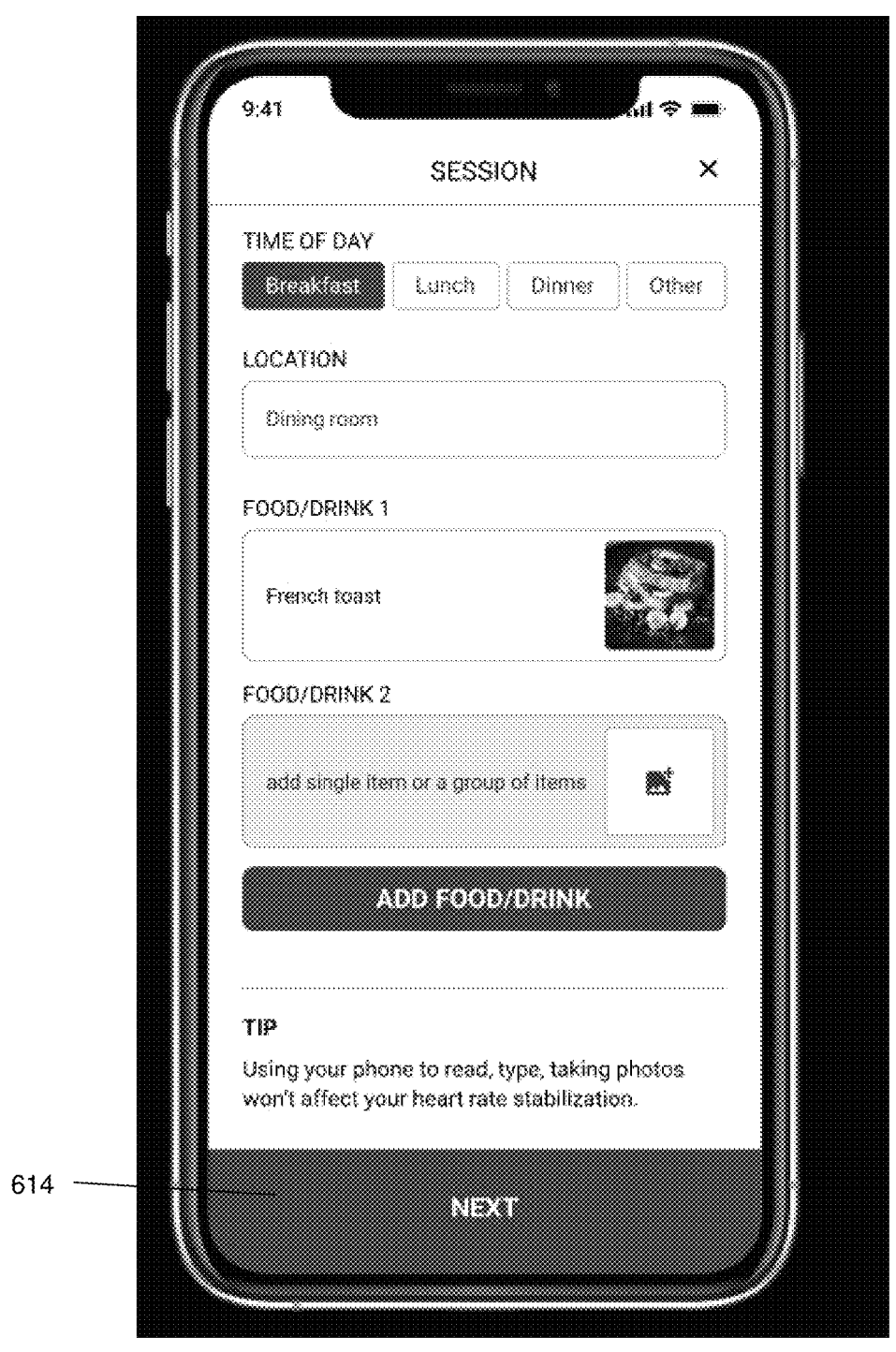

FIG. 6I shows an example of a user interface showing an example entered food. In this example, the time is "Breakfast", the location is "Dining room", and the food is "French toast" with an accompanying picture of the food. When all foods/drinks for the meal are entered, a button (614) can be pressed to begin the session.

Figure 6J:
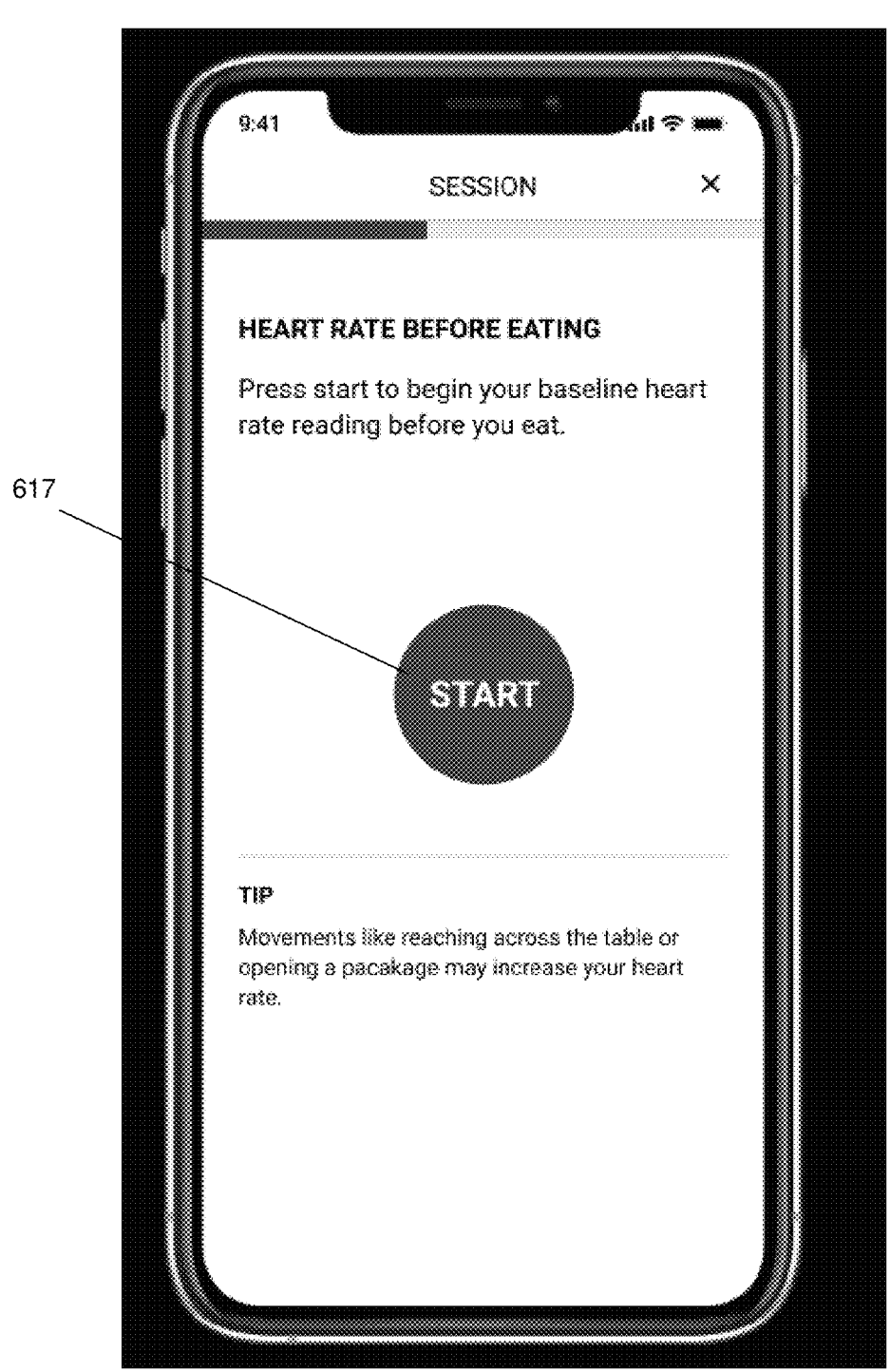

FIG. 6J shows an example of a user interface showing an example screen for the pre-meal baseline heart rate measurement. When the start button (617) is pressed, the baseline measurement starts.

Figure 6K:
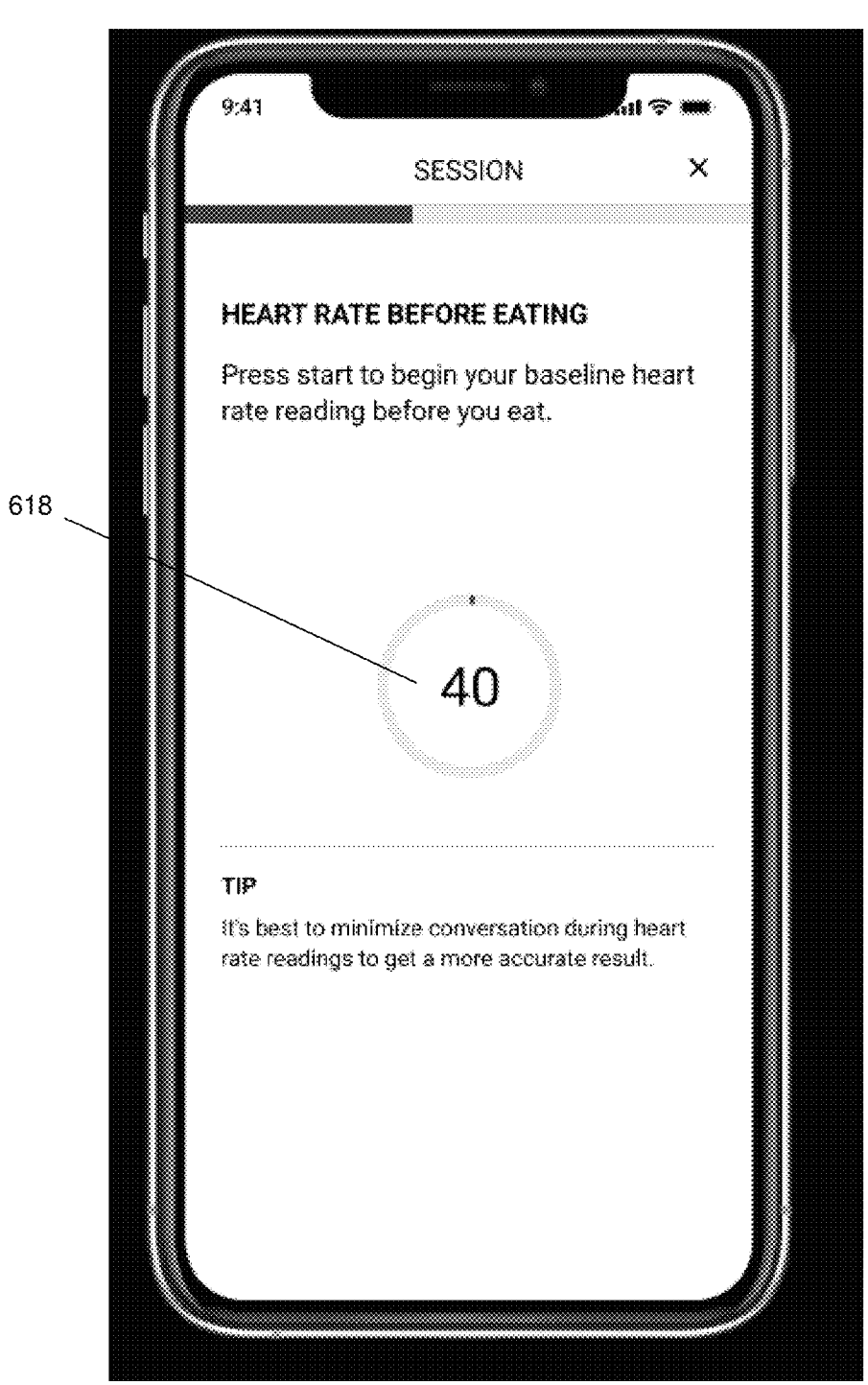

FIG. 6K shows an example of a user interface showing an example screen for the progress for the baseline measurement. After the baseline measurement starts, a timer (618) shows a countdown to when the baseline measurement ends, and the user can begin eating. The timer is set by the system, e.g., a one-minute countdown.

Figure 6L:
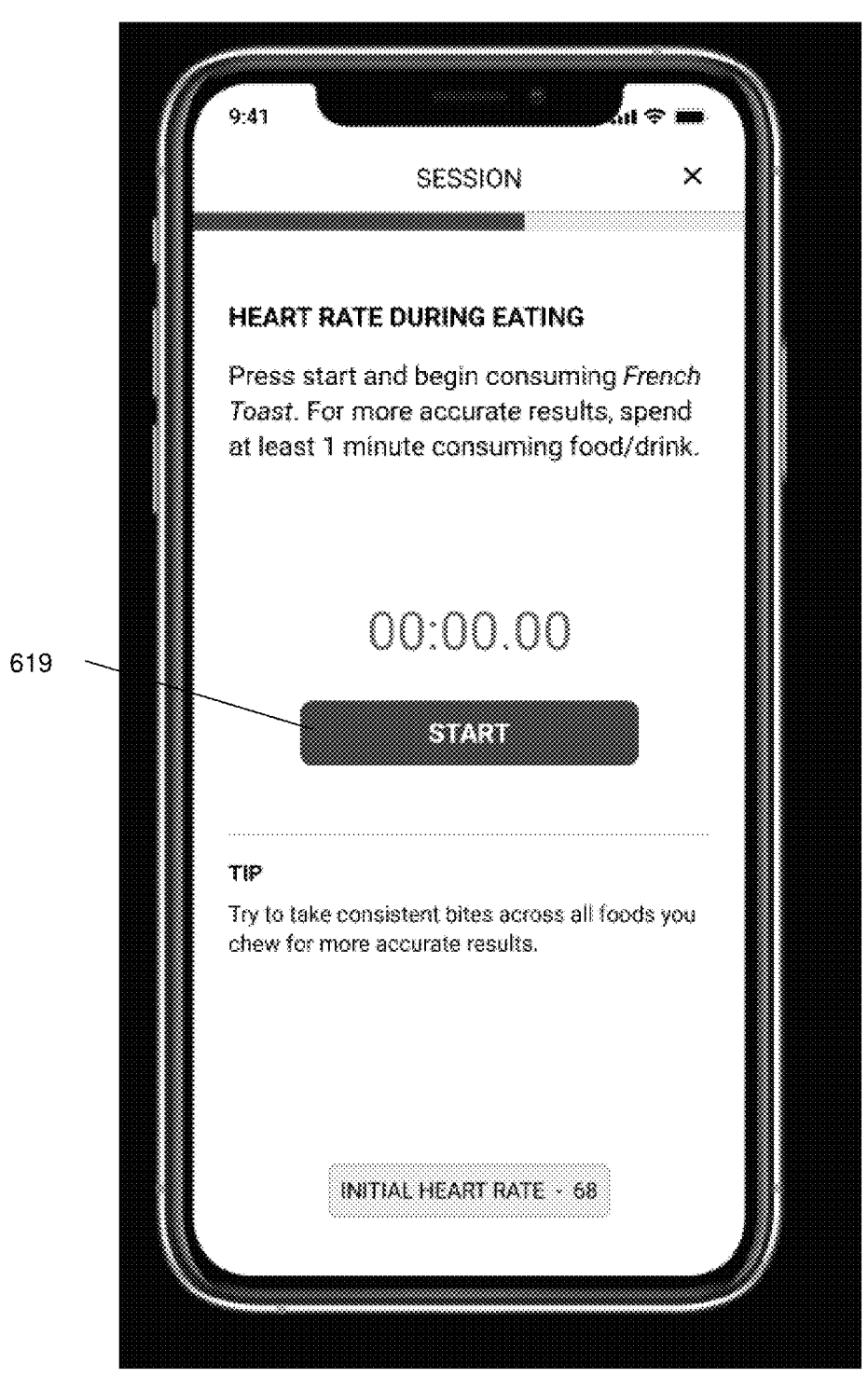

FIG. 6L shows an example of a user interface showing an example screen for the end of the baseline measurement. When the countdown ends, the user is presented with a button (619) to indicate to the system when they have started eating the meal.

Figure 6M:
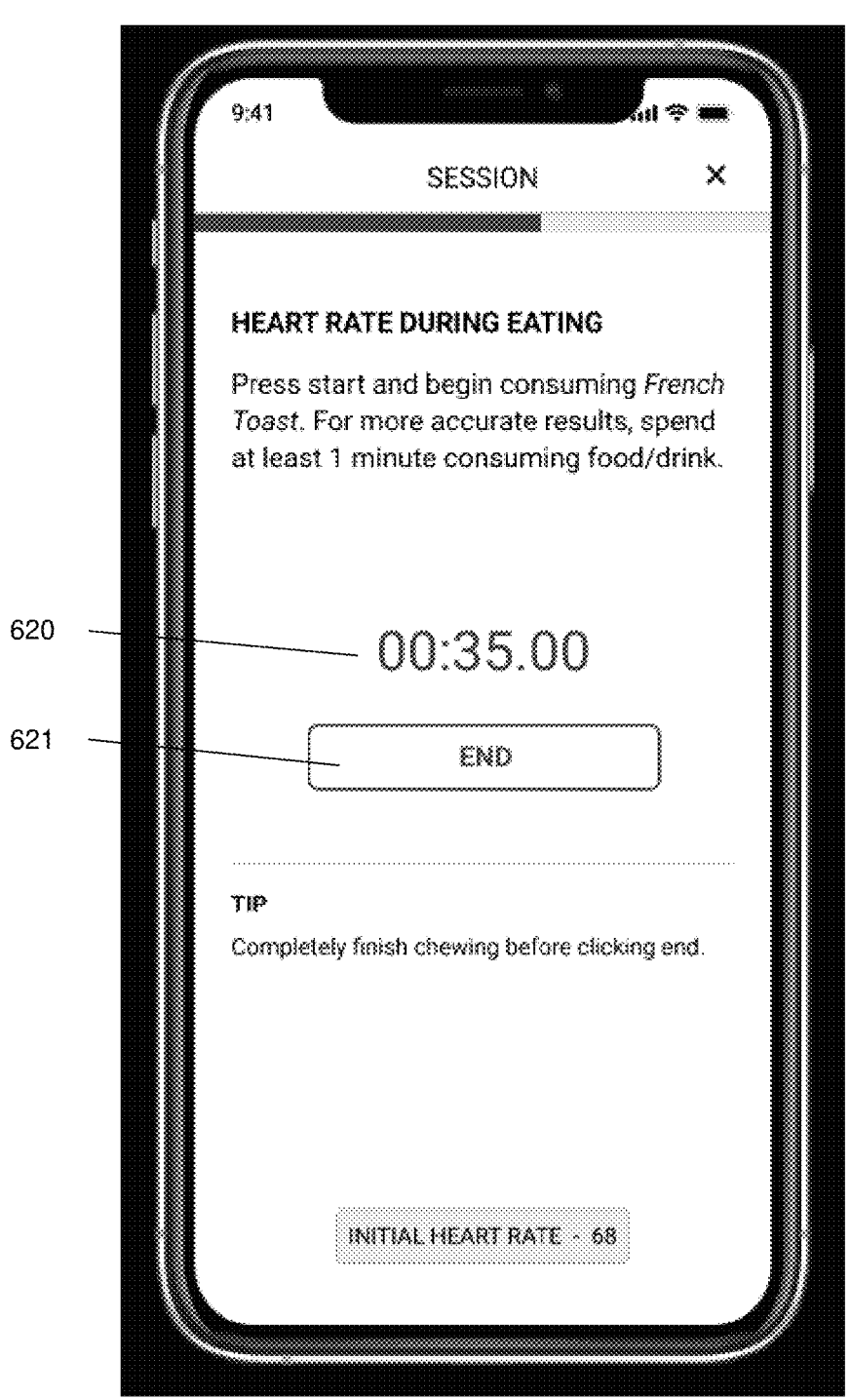

FIG. 6M shows an example of a user interface showing an example screen for the session during the meal. The time (620) can be displayed along with a button (621) to indicate to the system that the meal is finished (user has stopped eating).

Figure 6N:
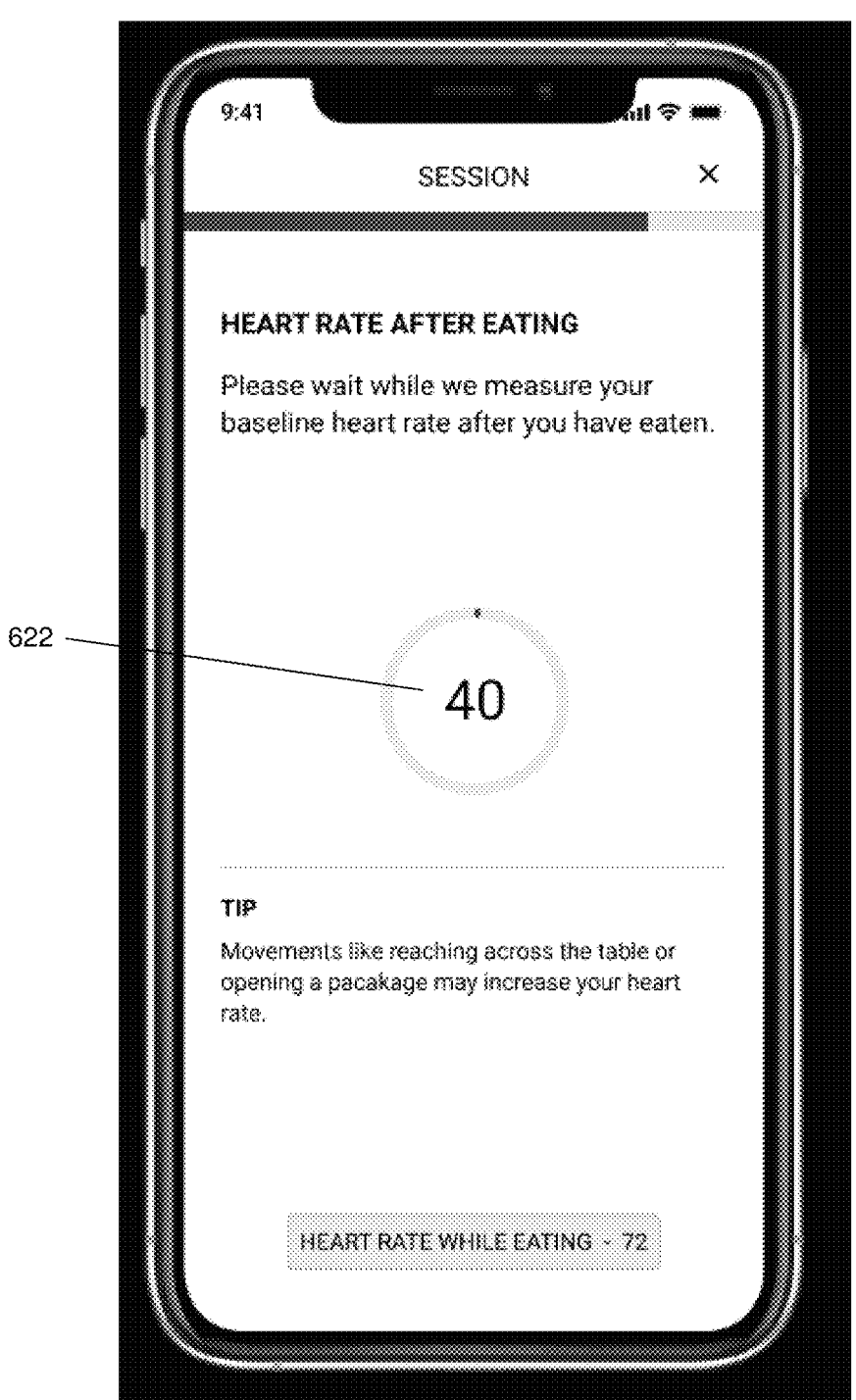

FIG. 6N shows an example of a user interface showing an example screen for post-meal heart rate measurements. Another timer (622) can be presented while the system measures the user's heart rate post-meal, e.g., another one-minute timer.

Figure 6O:
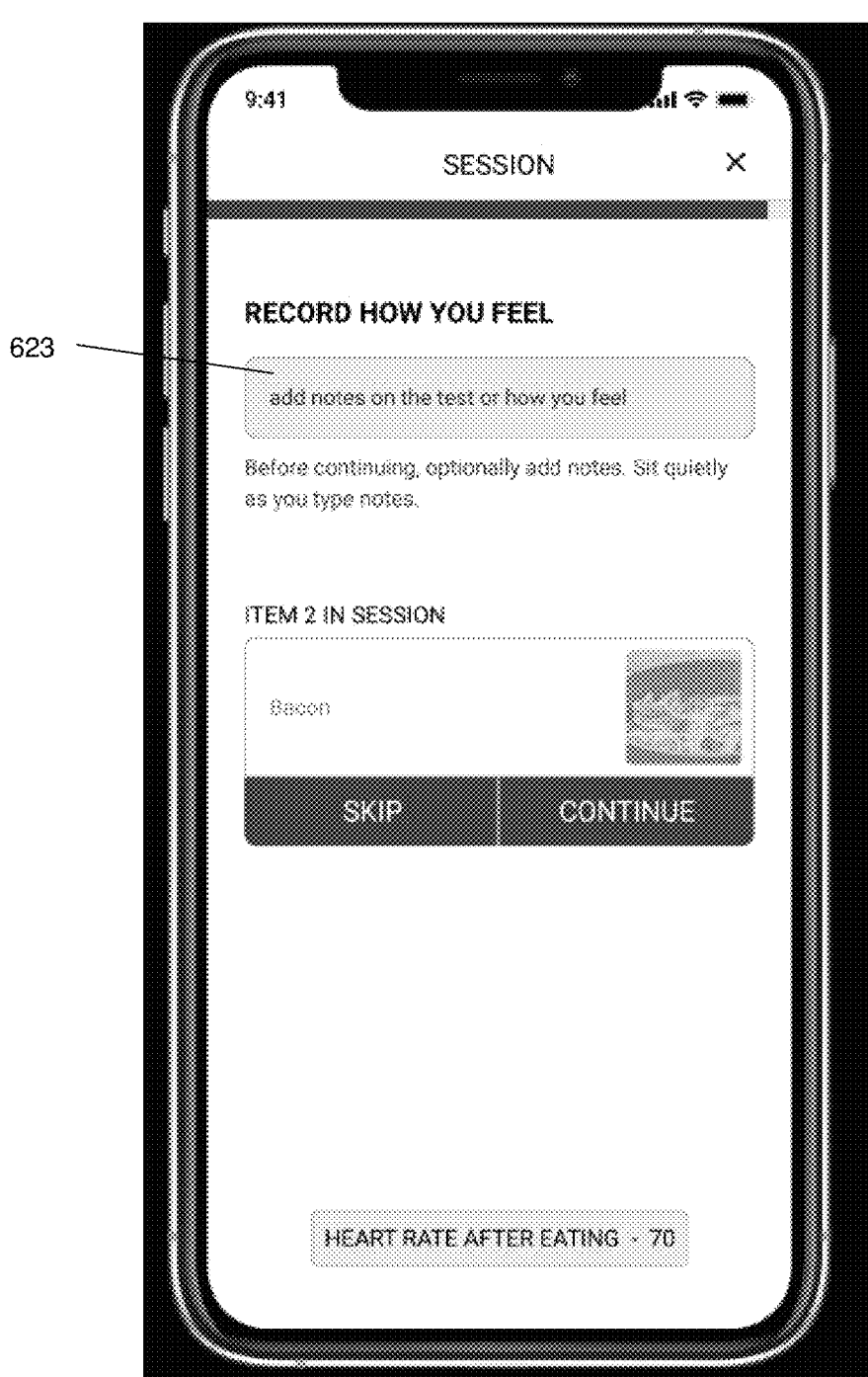

FIG. 6O shows an example of a user interface showing an example screen for post-meal notes (623) to be entered by the user. For example, the user can enter their perceived wellbeing after the meal.

Figure 6P:
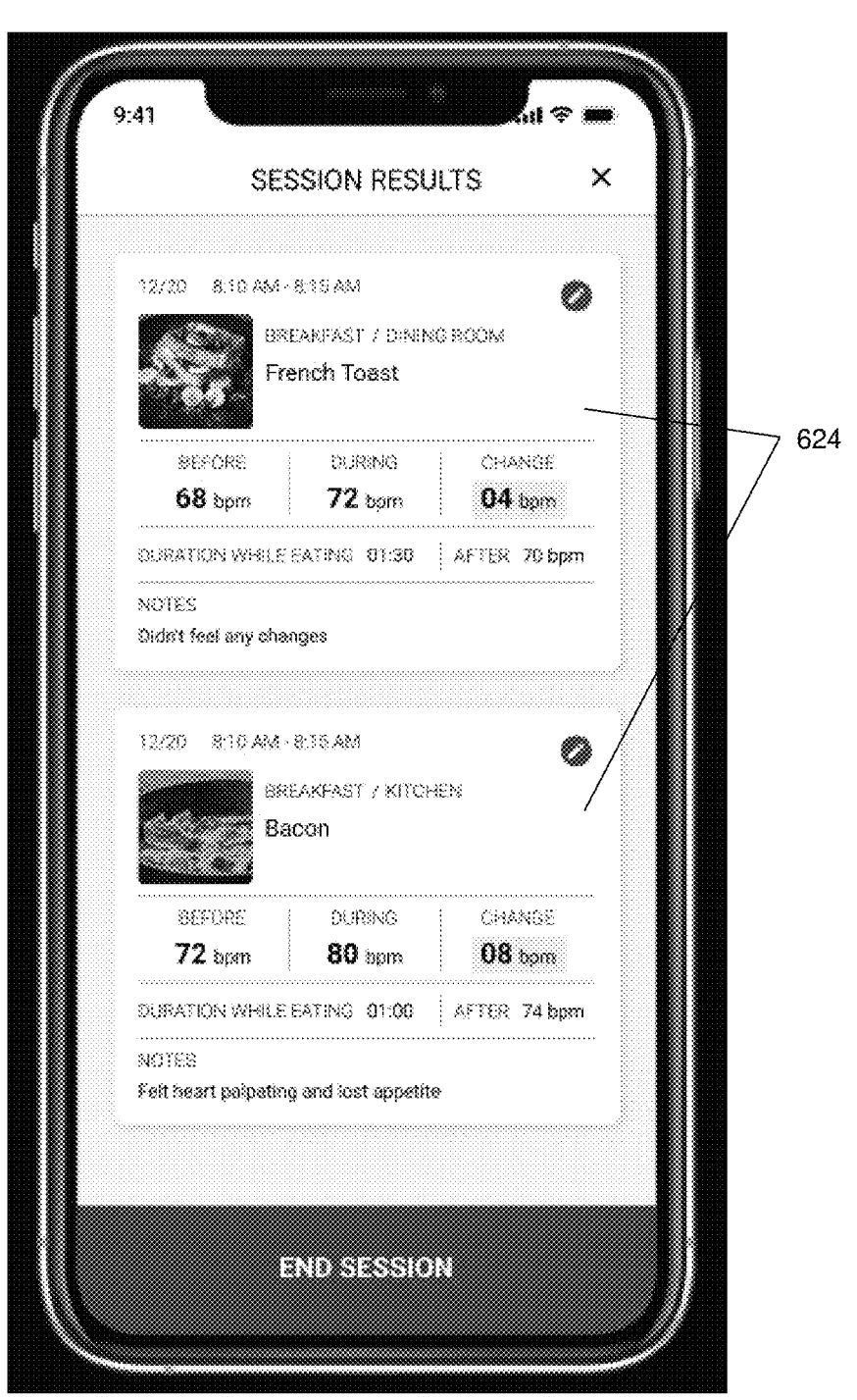

FIG. 6P shows an example of a user interface showing an example screen for displaying results to the user. The resulting data (food identification, heart rates before, during, and after the meal, meal duration, user notes, etc.) can be displayed (624) so the user can see how different meals (in this example, two back-to-back "breakfasts" being measured to compare two different foods—French Toast vs. Bacon— eaten in two different locations—Dining Room vs. Kitchen) change their heart rate.

Figure 6Q:
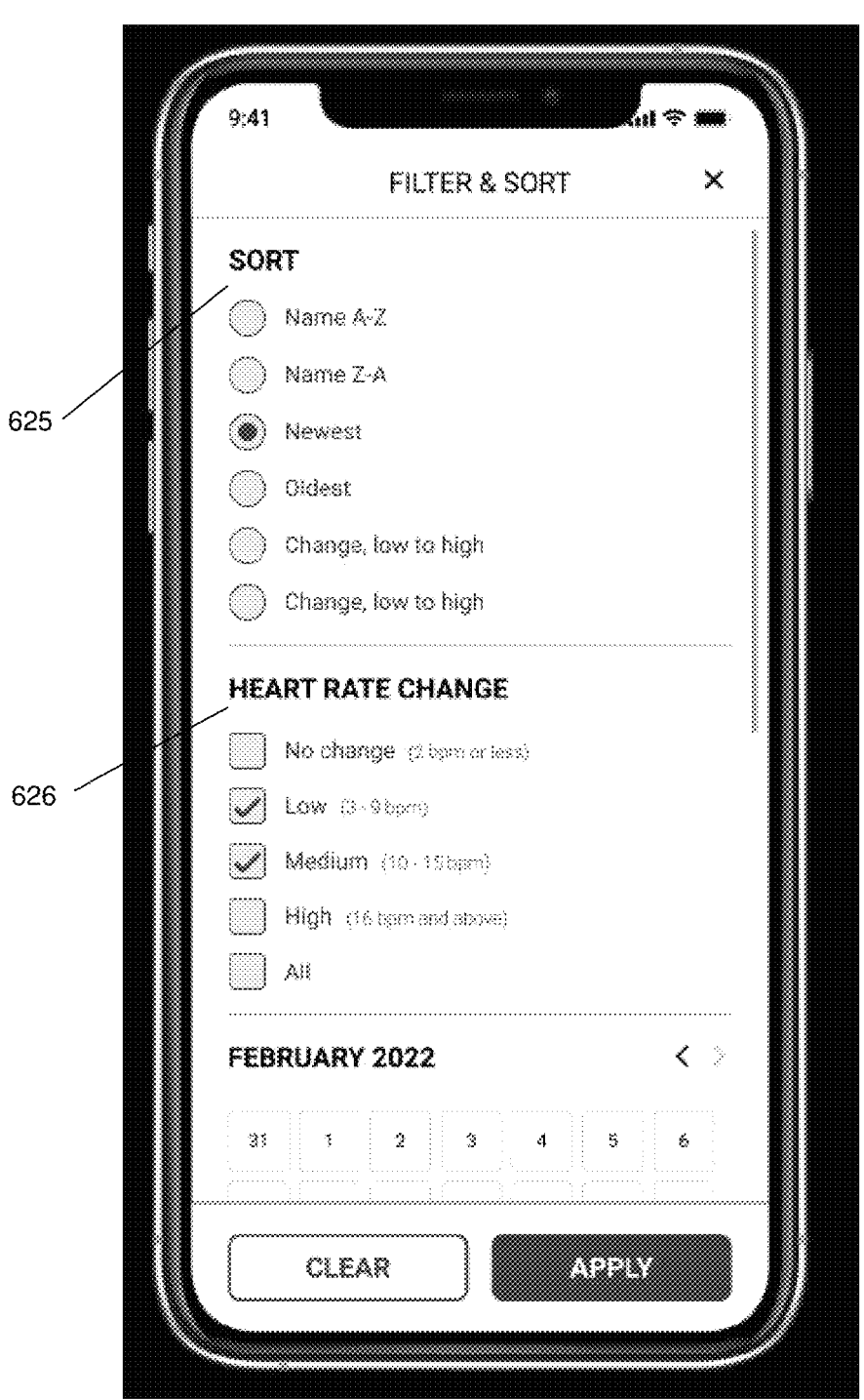
Figure 6R:
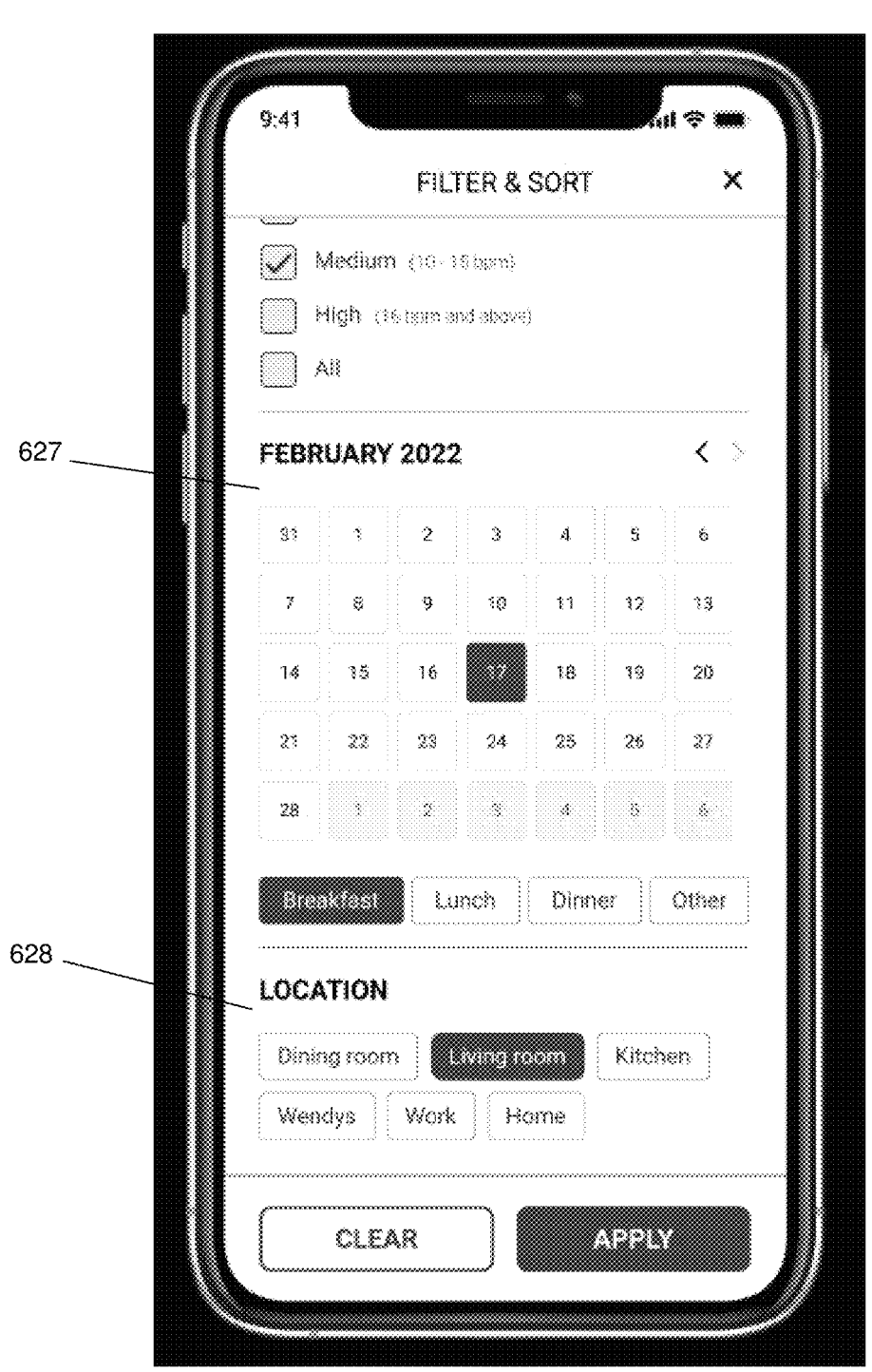

FIGS. 6Q and 6R show an example of a user interface to filter and/or sort the results. For example, the results can be sorted (625) based on various criteria (e.g., alphabetical, chronological, values, etc.). The results can also be filtered based on values/value ranges (626), date/time (627), location (628), etc.

Note that all the example screens shown in FIGS. 6A-6R can include other useful information for the user, such as a display of initial (baseline) heart rate or eating heart rate, or instructional text. The screens can also include advertising banners.

Example 35—Series of Measurements

Figure 7A:
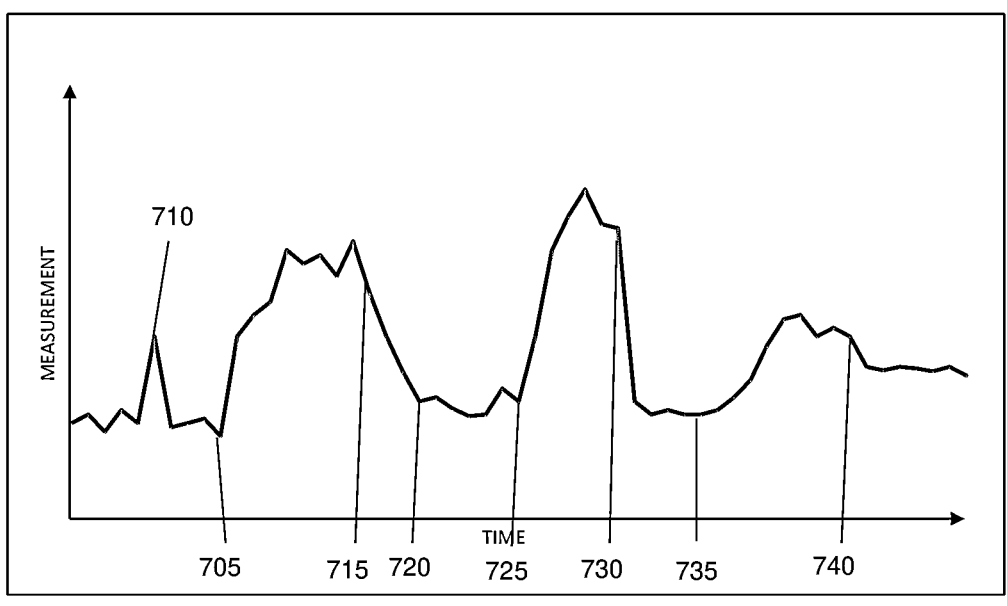
FIGS. 7A-7B show example graphs of measurements over time for the example system in use.
Figure 7B:
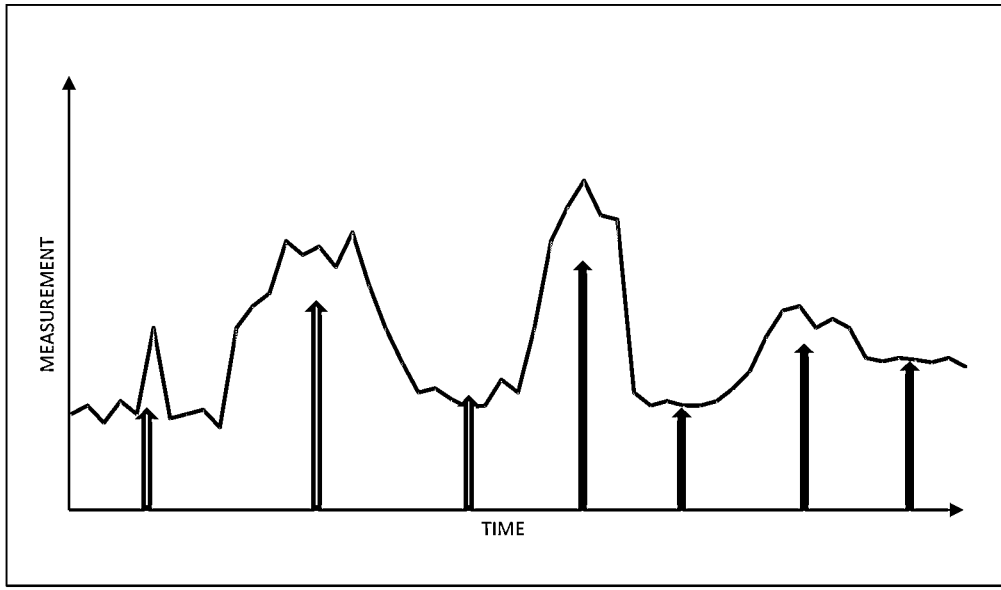

FIGS. 7A-7B show an example of three events (e.g. meals) being measured. FIG. 7A shows a graph of the measurements (e.g. bpm) taken over time. An initial baseline is measured until the start of the first event (705). One measurement (710) is unusually high, statistically, and so can be discounted when determining the first baseline. The first event is measured either until the event ends (715) or until the measurement reaches a new baseline (720). After a second baseline is established, the second event can start (725) until it ends (730). After a third baseline is established, a third event can start (735) and end (740) forming a fourth baseline. Note that the various baselines do not always settle to the same level, as some events might have longer-lasting effects. Based on the values of the various baselines and events, averages (e.g., broad arrows shown in FIG. 7B) can be determined for each. For example, the first event can be given a value that is the average of values between the start (705) to the end (715), or the average between the start (705) to the start of the next baseline (720). The start of the next baseline (720) can be compared by looking for a flattening (derivative near zero) of the curve over a window of measurements and seeing where the flattening begins. Another value of interest that could be used to indicate the amount of reaction to an item that can be calculated is the difference in baselines. For instance, the difference between the average baseline value after the third event (e.g., the period of time 10 to 50 seconds after the end of the third event (740)) and the average baseline before the third event (e.g., the period of time 10 to 50 seconds prior to the start of the third event (735)). One of many possible scores that could be used to indicate level of reaction to an item might include this difference in baselines, or this difference added to the amount that the average heart rate increases while eating. These are just some of the many examples, as discussed elsewhere in this document, which are included in the systems and methods described herein.

Since there is a delay (e.g., of 5 to 20 seconds or more) (latency period) before most measurements can be affected significantly by the beginning of an event, the baseline before the event can optionally include as part of the values that are used to calculate the baseline, the values of the measurements occurring after the event begins, near the beginning, before the changes from the event occur. The length of time of the latency period will vary depending on the particular measurement. Alternatively, especially in approaches that emphasize speed over accuracy, the values during this latency period could be used as the baseline. An example of this is shown at the beginning of the third event (735) which starts before an increase in measurement is detectable.

Example 36—Cancer Drugs

An example of the use of the systems disclosed herein that specifically focuses on medications includes cancer drug reactions. For example, suppose a cancer patient is on a complex regime of medications and the system uses biometric data, for example heart rate data, and looks for any trends in the biometric data in association with the drug delivery via intravenous and oral means. The patient begins to deteriorate unexpectedly 2 weeks into the therapy and the data is analyzed and shows that the heart rate when administering one of the intravenous medications has increased in the last few days. An alternative drug can then be trialed to replace the one that was associated with an increase in the heart rate and the patient stabilizes once again.

Short-term tests and responses to other items can be used to provide additional information. For instance, if short-term observations during a meal indicated that there was also a greater heart rate response to a food, for instance, beef, began within days of when the drug reaction began, the system could identify potentially cross-reacting medications. Information on what are the active and inactive components of the drug, including In silico modeling, might be used to identify potential cross-reactions with food or other environmental components to help flag particular substances as more likely to cross-react with the drug, thus providing further information for the system. The accumulation of data, both proprietary and from the literature regarding foods and substances in the environment that cross-react with various drugs could also help determine, before beginning a drug, which of several medications would be better tolerated by the patient. What is particularly novel about the system described herein is the incorporation of information from the analyses of stress responses of individual patients to external stimuli (e.g., food, inhalants) that can be used for the detection of the cross-reactions. An analogous approach could be used for types of drugs in other diseases and medical conditions.

Example 37—Cross-Reaction

As an example of the approach, monitoring of reactions to various exposures can be performed and cross-reaction information can be employed to improve responses to administered drugs and to overall patient outcomes. For example, if it is shown by the system that a heart rate increase related to a particular drug began near the time the user began eating a particular food, the system could cause an alert to notify the user (or caregiver) of the cross-reaction. In some cases, additional information might help inform decisions, such as the system determining that the highest heart rate reactions to the drug were within 2 days of eating large amounts of that food. In silico modeling might also suggest the potential for the cross-reaction due to similarity of molecular structure between a component of the food and a component of the drug. In silico modeling, proprietary information, or evolving research findings might indicate that the drug increases the growth of an intestinal microbe that cross-reacted with the food. The totality of information from the system can then suggest to the health care provider to consider switching the patient to a different drug and/or instruct the patient to stop eating that particular food. If the patient stopped eating the food, they might be able to stay on the drug. This information on a potential cross-reaction can be added to the system to help in the identification of future food-drug cross-reactions.

Example 38—Cameras

This disclosure also includes a system or systems employing a camera or cameras that can observe the food being eaten and follow the heart rate and correlate it with which food is being chewed at any point in time and use artificial intelligence/machine learning (AI/ML) and/or statistical methods to estimate which foods cause the highest heart rate, even without a person limiting themselves to only one food at a time. Methods to detect and identify the food using AI/ML can be used, or a photograph of which food caused the highest heart rate during the meal can be shown and the user or their caregiver can later identify the food.

Example 39—Monitored Areas

In another embodiment, the integration of the other aspects disclosed herein with a method or methods of having cameras positioned in one or many rooms of a house or other indoor or outdoor locations that can track the location and activities of the user and then correlate them with changes in biometric data. The systems can especially focus on biometric changes that are related to changes in substances that are inhaled or that in other ways come into contact with the human beings or animal tissues. This information can also be correlated to foods eaten in recent days to help determine the relevant cross-reactions.

For example, suppose it is found that there is a modest increase in heart rate of the user over the short-term while eating shrimp. However, the camera and the continuous stream of data shows that there is a marked increase in heart rate when the person is in a closet that is very dusty, and this could be flagged for attention since shrimp and other crustaceans can cross-react with dust mites. Over time, the analysis of the data could further support this inference by revealing that the heart rate increase from being in the closet only occurs if shrimp has been eaten during the previous week. Through the use of cameras, it may be, thus, unnecessary for the user to enter the data with regard to location.

Furthermore, if the person leaves the premises where the cameras are located, then GPS data could be used to locate the person, or some device attached to the person (e.g., body cam) could also be used to indicate types of locations, events and exposures. Various types of automatic recognition of location or activity could be done, including use of gyroscopes. Activity level could be measured via gyroscopes, or accelerometers or other existing means or methods as known in the art, to adjust for the effect of movement and exercise on the biometric data in order to remove that source of confounding.

These types of systems, as disclosed herein, would be very useful in cases of disabled or elderly persons who might not be able to or have the energy or know how to enter information and carry out tests. These systems would also potentially include gathering data via sonar or radar or other current, or yet-to-be developed methods. The ability to gather biometric data from a distance would avoid the necessity of wearing sensors to gather the data, which might not be comfortable or desirable for some people.

These methods would not only allow the elderly or disabled person's status to be monitored in greater depth than usual, but could lead to improvements in their health and/or well-being by identifying exposures that are potentially problematic. This could be accomplished earlier than through most other means, thus conceivably preventing deterioration or leading to more expeditious medical attention.

Even if the user is able bodied, this type of system could be desirable due to its greater convenience and thoroughness. Thus, another embodiment of this disclosure is the use of the systems described herein in able bodied users.

Example 40—Statistical Analysis

The effect on the biometric measurements of the digestion and absorption of the food that occurs in the hours after ingestion can also be detected and included in the various types of analyses described herein.

Various AI/ML and statistical methods (e.g., multivariate regressions) could help clarify which exposures and cross-reactions are most significant and relevant. This could be accomplished by using proprietary and published information and information downloaded from the internet that suggest probable sources of reactions and stress-responses and reactions of various types. These sources of information could also be combined with data specific to the individual user to inform the analytical methods used by the system or systems.

For example, published data on the molecular analyses of certain epitopes of allergens can help inform the approach.

Likewise, case reports or reports published on the internet, with or without molecular analyses, can suggest cross-reactions. The area of latex cross-reactions, for instance, is an area that is evolving, and new cross-reactions continue to be identified between latex and various foods, especially fruits. In addition, research on what individuals who have a latex allergy tend to be allergic to can suggest the presence of cross-reactions with latex even if the research on the molecular structures has not been completed. Proprietary information may also be gathered by the system in which a cross-reaction may be presumed even if it cannot be firmly identified at a molecular level or even if the substance or antigen is not actually identified. For instance, if a person eats a particular food and it causes a change in their biological signals (e.g., increase in heart rate) that tends to increase only when they consume more of another food, it might be postulated that the two foods contain a component that cross-reacts, and they need to have a certain threshold of exposure that component for them to have a clear reaction. An example might be a reaction to the group of chemicals, salicylates, which are common in many foods. It might be salicylates are causing a reaction, but it might be another substance or group of cross-reacting substances common in many foods. If enough data is gathered on reactions, both for individuals and groups of individuals, it might be possible to determine, through analysis of patterns of reactions (sometimes combined with AI/ML or various statistical methods) what component of the food a person is reacting to. This can be accomplished, when this type of information is available, through the information on the chemical contents/sequelae of food and other external stimuli being included in the AI/ML along with information on the pattern of reactions. It should be noted that this includes changes in chemical characteristics and new chemicals produced as a result of the effect of radiation (e.g., ultraviolet, infrared, x-rays, gamma rays etc.) This would be an example of chemical sequelae from the external stimuli of radiation. Differences in the substances that microbes produce after they are subjected to radiation of various types or are subjected to antibiotics in the human body would be other examples. In the area of microbial allergens, current and future research should also help delineate cross-reactions. As of now, only a few microbial allergens have been studied. Microbes are abundant in our environment, and microbes are commonly found in the lungs and other parts of the respiratory system and also can enter the body in other ways (e.g., across the intestinal lining due to intestinal permeability). Thus, as more details with regard to microbial allergens are obtained through research in this field, these details can be included in the system described herein. Intestinal permeability is found to increase with age and a wide variety of medical conditions and is also influenced by medications and alcohol. Entry of microbes into the body, in the case of microbes that can survive and colonize mammalian tissues (e.g., the fungi, *Aspergillus fumigatus*, in the respiratory tract of immunocompromised people), could lead to substances being produced by microbes in the body that are also produced by the microbes in the environment. The allergens produced by microbes within the body could possibly account for increased sensitivity to certain microbes in food and in the environment in some cases and have other effects as well.

Example 41—Augmented Reality

Another embodiment of the present disclosure involves augmented reality technology to add an additional level of real time feedback and data that enhances convenience for the user. By "augmented reality" it is meant a system that presents computer-generated image/images overlaid on an actual image of the user's surroundings or a remotely viewed region (e.g., through a camera). Augmented reality approaches that present data or visual information to the user (e.g., using glasses in front of the eyes that are connected to a mobile device or laptop via Bluetooth or another means of connection) can show the user data on their heart rate and information that helps interpret the meaning of the user's heart rate data (for example, showing a gray color overlay for no reaction, blue for a low level of heart rate reaction, yellow for slight reaction, and red for a higher level of reaction). The information that is presented to the user can also optionally present data about items and locations that previously had been associated with the heart rate reaction. Thus, it might depict patterns determined by the system with words, symbols, pictures or the like, to indicate what item or location the user might be having a reaction to and what cross-reactions might be involved. It could use historical data about what foods the user has reacted to when using the short-term heart rate tests discussed previously. Machine learning methods or other means of artificial intelligence could be used to determine the patterns it depicts, as would be understood by one skilled in the art. This information could also be used in conjunction with a medical device, such as one that controls breathing, in order to alleviate reactions.

By "machine learning" or "artificial intelligence", it is meant a computerized system that performs pattern recognition or classification by an algorithm that uses data to improve performance of the recognition/classification. An example is a classification system that uses potential stimulus (foods, locations, times of day, etc.) classified by resulting biomedical measurement (e.g., heart rate). This model can then be used to classify new, untested combinations of stimulus in terms of expected biomedical response.

An example is a user moving through their home and, when standing for several minutes in their kitchen, their augmented reality glasses show a yellow color in the corner of the eyeglasses and the number "12", indicating the heart rate has gone up 12 beats per minute. It can also show, for example, either the word "apple" or a picture of an apple because the machine learning classifier indicates that it predicts that a combination of eating an apple and standing near a sink produce an increased heart rate.

Another example is a machine learning algorithm determining two possible sources of reaction, an apple and/or an orange, and the glasses shows an apple image/text alternating with an orange image/text. The orange can be shown as fainter or smaller in a situation where the data was less certain with regard to the orange (e.g., machine learning shows less correlation than it did for the apple). The glasses can show a symbol or word indicating a breath-controlling medical device or some other method (e.g., a particular breathing method) should be used if the user wishes to decrease the reaction and then when the reaction is decreased, the yellow light changes to grey and the apple image fades. It can also notify the reader, perhaps with a line through the apple and "2 days" as an indication to the user to avoid eating apples for 2 days. Optionally, this information can be included in dietary recommendations that the user receives at set times (e.g., every morning) and/or on demand.

A similar approach to augmented reality could be done using other biological signals, such as blood pressure, GSR, EEG, EKG etc. or combinations of such signals.

Caregivers of all types, including medical professionals can use the system with such augmented reality glasses and receive timely information about those they care for. For someone, like a doctor or nurse, who is caring for multiple people, information as to the person's identity would be included as well as the other types of information discussed above, e.g., name, initials or room or bed number or other means of identification. The person's identity can be determined by reading an identification tag worn by the patient (e.g., a computer-readable quick response or bar tag) or by facial recognition software. The device can prioritize giving information regarding patients with the most extreme reactions and if the caregiver had multiple patients who had reactions at the same time, the system can be set up to alert a different caregiver, for example, a caregiver who has more time available or is on call.

Example 42—Other Sources of Information

Accelerometers, gyroscopes, camera information and other similar sources of information can be used to adjust for activity level effects on heart rate or other biological signals. For example, if the pattern of information from the gyroscope indicated that the person had just stood up, then the system would not interpret that as a heart rate increase from a reaction. Similarly, this information on movement could prevent the heart rate increase from a person turning over in bed from being confused with a reaction occurring when the person is, for example, drinking a beverage.

Example 43—Daily Monitoring

Another embodiment involves the short-term tests discussed herein being integrated with biological signals gathered throughout a day (or some other span of time) to provide even more information on the user's condition. For example, data can be gathered on a biological signal, such as the heart rate, in some regular pattern to allow comparisons between different times of day, days, weeks etc. One example is gathering the heart rate data: overnight (e.g., minimum or average); before getting up; just before eating; and 30, 60, 90, and 120 minutes after meals. In one embodiment, if these heart rate values are above the usual (e.g., the maximum values vary by more than 2 bpm), the user can be alerted that there is likely to have been some exposure that has caused a reaction. If data was available to the system regarding the food the user was eating, the system can also take the step of comparing the heart rate pattern to the dietary pattern of the person and make suggestions as to which food might be responsible. It might be that person had introduced some food that they don't typically eat and that would be found to be correlated with the heart rate increase. Sometimes there is a lag effect, and they might only begin reacting on the third day of eating the food. The system can be programmed to allow for the possible existence of a time lag in the effect of a newly introduced food.

Example 44—Verifying Sitting Quietly

In some embodiments, the system can determine, based on a variety of indications (e.g., gyroscope, calendar, accelerometer), when the person is likely to be sitting quietly when taking the heart rate approximately 30, 60 and 90 minutes after every meal. The system can optionally ask the user if they are sitting quietly to verify this. The system can also take the heart rate automatically in the morning before rising and in the evening before falling asleep. Then, if a food diary (data) is available, it can suggest foods that could be a problem (based on food diaries, short-term tests and other information gathered by the system). It can also incorporate knowledge about cross-reactions between foods, inhalants etc. and other information, both proprietary, from the person's history and from the Internet regarding potential reactions in order to make suggestions. Examples of information taken from the internet might be research articles on foods that are discovered to cross-react with latex or new cross-reactions between genetically modified food and already known allergens. Proprietary information might be information on what foods and inhalants have been found to cross-react in the population of users of the mobile application.

As used herein, "proprietary information" means information held by the system that is not widely available to the public.

To increase accuracy, the system can instruct the person to sit when it is going to do the readings of heart rate at set intervals (e.g., 30, 60 and 90 minutes after meals), and the user could be prompted to inform the system when he/she is beginning and ending a meal. The system can verify by the above-mentioned methods to determine if the person is sitting still (e.g., gyroscopic/accelerometer data shows no or very little movement). Alternatively, the system could use a preset schedule to estimate the mealtime, combined with data indicating whether the person is moving, to infer that the meal is beginning. A check can be done by the system through a prompt asking the user whether they are eating.

Example 45—Location Data

In some embodiments, a more complex and detailed approach related to location data is used by the system. If location data is gathered or provided by the system, this information can be used to make suggestions for avoiding exposure to an external stimuli that would cause a reaction. For example, GPS data could determine that the person has gone to a shopping mall. This could be combined with historical data about previous exposures and their related reactions to provide information to the user as to actions the user might take to avoid a reaction. In an embodiment, information from one or more of the following could be used to gain information about the person's exposures: GPS, their calendar (e.g., from a computer app), home camera data, or other devices for detecting locations such as LIDAR, radar, sonar, solar radiation detection equipment, chemical/microbiome detection equipment data (such as an exposometer used in studies of the exposome), or information input by the user. This information on exposures and location can be correlated with a variety of biological signals detected with one or more of the detectors mentioned previously (detectors of heart rate, GSR, blood pressure). All such correlations can be adjusted based on user's activity as measured, for example, by motion detectors (e.g., accelerometers). For instance, if the accelerometer detects movement at a certain number of feet per second, it can be determined how much the heart rate increases compared to the average increase in heart rate with a given amount of acceleration for that particular user. A greater than average increase in heart rate for a given level of acceleration might be flagged as potentially related to a reaction to an inhalant in the environment.

An example is GPS information combined with heart rate data to determine that the user's heart rate went up when they were in an outdoor park and not when they were in a shopping mall. When combined with information on weather and air quality conditions, it might be found that the temperature was not extreme, pollen counts were low, but the level of air pollution was high, suggesting a possible stress response to air pollution. Another example is with a chemical/microbiome detection device, it might be found that a blood pressure elevation was linked to a particular chemical or microbial exposure. This approach and any of the systems/methods discussed in this document could be integrated with augmented reality and/or Internet-of-things systems, as discussed elsewhere in this document, to provide additional benefits.

Example 46—Mental State

In some embodiments, the user can be prompted by the system to note their mental state so that if they were feeling extremely stressed due to a specific psychosocial event, the potential for psychological effects on heart rate could be considered. However, the ability for mental stress to follow from physical stress from an exposure can also be considered. The system can help the individual disentangle the effects by asking the user a series of questions such as:

"Are you feeling psychological stress due to some event?"

"Do you think that the level of stress you are feeling due to this event is higher than usual?"

Data gathered over time using the above system and questions such as this might indicate that the person tends to feel more stress from some ongoing event (e.g., a divorce) when they are exposed to high levels of air pollution, indicating that air pollution exacerbates their perceived stress level.

Example 47—Q&A Interrogation

In some embodiments, such as where there is not as much data on relevant exposure patterns that is gathered by the system, a question-and-answer format using proprietary data or information from the Internet or research studies could be used to help the user to arrive at the right conclusions or at least suggest possibilities to the user for possible useful actions. Proprietary information or published data on items that might cross-react or types of symptoms that might result from particular exposures could be used to help arrive at conclusions with regard to biological signals from particular exposures. In some cases, short-term heart rate tests could help in determining the source of the reaction. It could be used alongside published data on foods that cross-react with tree pollen and produce particular symptoms.

For example, when the resting heart rate is elevated at 4 pm, the system could query the user, asking:

Question from the system: Did you do anything different or go anywhere different today at 4 pm?

Answer: Yes, I drove to the car repair place to leave my car for repair.

Question from the system: Did you feel any symptoms at the car repair place?

Answer: Yes, I felt a mild tension headache.

Suggestion from the system: You might want to use the medical device today and monitor yourself for headaches when you go to places that might have fumes from chemicals.

Another Example:

Question from the system: Did you do something different at 11 am today?

Answer from the user: I sat under the birch tree

Question from the system: Did you have any symptoms at that time or afterwards when you had lunch?

Answer from the user: I did not have any symptoms when I was outside, but my mouth was slightly sore when I ate a peach at lunch.

Suggestions: Avoid eating peaches until you talk to your doctor about oral allergy syndrome, a condition in which certain foods cross-react with certain pollens. You could also see if your heart rate increases under the birch trees using a short-term test.

Example 48—Pattern Significance

There are certain patterns that the system could determine through machine learning or pre-programmed known patterns the significance of the patterns found by the system. For example, it might be observed that the resting heart rate is higher when a food that has caused a reaction has moved through the digestive system to the point that is in the lowest part of the descending colon. Since people differ in the time it takes for food to move through their digestive tract, it might be that there would be an elevated resting heart rate several days later (e.g., 1 to 3 or more days) after the reaction occurred, depending on the person's bowel transit time.

Example 49—Standing vs. Sitting

In some embodiments, running tests in a sitting position vs. running the same tests in a standing position can be used to measure overall health and reactions to various exposures by the system. The system could use an accelerometer, gyroscope, or other ways of detecting movement to determine if one is sitting and if one stands up. It can also remind people to stand up at certain intervals. The system can measure the sitting heart rate and the pattern of heart rate increase and the level of heart rate after it stabilizes and the recovery curve (as the heart rate tends to go up more at first and then often stabilizes at a higher level after 30 to 40 seconds). This type of assessment could help motivate people and help them assess where they are in the spectrum of wellness levels. By "stabilize", it is meant that the level remains within a threshold range for a threshold period of time, the thresholds set by the system and/or the user. Differences in biological signals between the prone position and sitting or standing can also be assessed and used to indicate the health status of the person.

Example 50—Personal Needs

Some people may have only rare reactions to foods and other substances and thus would find individual tests less appealing, due to a low yield of reactions. The following are examples of methods for the system that require minimal investment of time by the user and could yield useful results, particularly in people who seldom have reactions.

The system can use a measurement signal increase above a certain level to notify the user while they are eating that a particular food/beverage caused an increase in heart rate or some other biological signal above a particular level or by a % increase (set by the system or the user) and it could show a prompt asking the user to input what the food item was that they were eating at the time of the increase. The alert regarding the increase could occur via a vibration, sound or visual prompt. This would likely work best for people who rarely had their food or other factors affect their heart rate. Optionally, it can require that the increase was for more than some particular length of time, e.g., longer than 1 second. It can also use the average heart rate over a given length of time to trigger the alert. The alert can be set to be louder or stronger depending on how large the increase is.

Another method, for cases where there are more increases in reaction (e.g., heart rate) involving more foods, it could be similar to the above, with alerts, but it can also identify foods that caused a steeper change in reaction than other foods (e.g., greater slope of the heart rate curve). This method, using the slope, has the advantage of not being as influenced by the prior food, which may have increased the baseline level, causing the next food to reach a higher level, even though that food might not be the issue. All of these can be applied to other external stimuli in addition to foods and beverages and can apply to decreases as well as increases in biological signals.

Example 51—Determining Best Test Method

The system could analyze heart rate changes during meals and determine which method (from EXAMPLE 50) would be better for a particular person or could provide data based on both methods. For instance, for a person who wanted to be notified of any foods with any possible chance of a reaction, they might be notified of all foods that are possibilities based on either method. If one only wanted to be notified regarding foods that were more likely to be causing some stress reactions, they could be notified only if they were flagged by both methods. The system could also analyze the data and let the user know when it is likely to be less accurate, due to high variation in the biological signal. And the system could tell the user if some meals were different than others in terms of the need for individual tests. If the user had input data on what they ate at various meals, it could identify which foods should be tested individually.

Optionally, there could be a system that analyzes your heart rate or other biological signals and makes a recommendation as to which method should be used depending on your data or whether it is recommend that individual foods be tested with short-term tests discussed herein and exemplified in the Figures.

Example 52—Atrial Fibrillation or Other Discrete Event Prediction/Correlation Analysis Episodes of atrial fibrillation can occur intermittently throughout the day and night and it can be useful to know how the episodes of atrial fibrillation might be related to various external stimuli and activities (e.g., sleep, exercise, alcohol, food). One embodiment of the system described herein can be integrated with approaches that detect when atrial fibrillation occurs (e.g., using a Holter monitor, event recorder, mobile cardiac telemetry or insertable cardiac monitor or using an algorithm that detects atrial fibrillation from the ECG reading from a smart watch or fitness tracker) and then the episodes of atrial fibrillation (atrial fibrillation history) can be related to external signals (e.g., exposures or events related to foods, beverages, objects encountered and locations) to determine what signals impact the amount and timing of atrial fibrillation and the potential sequelae, including symptoms such as lightheadedness, ventricular tachycardia or ventricular fibrillation.

In one embodiment, the data gathered from short-term tests (or other analyses of responses described herein) of foods, beverages and other external stimuli can be analyzed to determine what, if any of the foods/beverages cause changes in biological signals (e.g., heart rate, blood pressure, EEG, GSR) and thus might be related to atrial fibrillation episodes. The system could also identify lag effects, such as whether episodes of atrial fibrillation occurred two hours after a food was ingested that caused a 10 bpm or greater increase in average resting heart rate while eating the food or if there were other cofactors needed for the increase. For example, perhaps the effect on atrial fibrillation only occurred if two foods that were determined to be cross-reacting (through a combination of individual, proprietary, and published research) were consumed at higher levels for at least three days in a row (or some other set period of time). It might be determined through artificial intelligence/machine learning, that this combination of factors explained the atrial fibrillation or at least increased the risk for a particular individual. The machine learning approach could be trained on the data of an individual or a collection of individuals and might include a variety of sources of information (proprietary or publicly available data). Various combinations of factors that have been discussed throughout this document could be analyzed to arrive at this type of predictive model and it could be done for an individual who is self-sufficient or could be done in the situation involving a caregiver, as described herein. As also described herein, data on movement and activity could be used to adjust for activity level. And systems in which radar (e.g., ultra-wide band radar) is assessing the heart rate could be used as well. Mention of these examples should not be taken to imply that these are the only aspects of the present disclosure that could be applied. Any of the other methods described herein could be used in the case of atrial fibrillation. Any other discrete event could also take the place of atrial fibrillation in this example, e.g., an epileptic seizure, an angina episode, a prolonged coughing spell, a migraine headache, an asthma attack, or an exacerbation/change of basically any sign, symptom, disease or function of the body. These events could be noted by the individual or the caregiver and could be entered into the system. Other events like hospitalization or ICU admission could be included. Positive changes/events could be recorded as well so as to analyze the exposure pattern that correlate with them (e.g. a record-breaking time for a marathon).

In some cases, surrogate markers of a worsening condition that stops short of a severe episode could be used to indicate worsening that could be linked to the biological signals described herein. Some examples, that are not exhaustive are the use of spirometry (in some cases, using portable digital spirometers) to indicate airway dysfunction that predisposes the patient to an asthma attack. In the case of epilepsy, there are apps and devices that detect changes in movement patterns that indicate an epileptic attack may soon occur. In the case of heart failure, observations like increases in fluid retention (indicated by sudden weight gain), shortness of breath and tachycardia may be used to indicate worsening. In the case of migraines, portable EEGs (electroencephalograms) can be used to help predict a predisposition to migraine development. In fatiguing conditions or as indications of worsening health from a variety of causes, a decline in step count could be used. In Parkinson's disease, devices and apps that measure tremor or gait could indicate worsening. In mood disorders, devices (like the Amazon Halo™) that use the tone of a person's voice to indicate their mood or devices that use step counts or movement detection could be employed to measure mood from the person's gait. In dementia, patterns of use of cell phones, computers, or other devices or the way the person speaks could potentially be used to indicate worsening cognitive abilities. Increases in blood pressure could indicate a risk for a hypertensive crisis. Changes in heart rate, temperature, respiratory rate, blood oxygen or step count could be used alone or in combination to indicate an exacerbation of a respiratory disease such as COVID-19. A smart toilet could be used to detect whether constipation or diarrhea is occurring and quantify the severity as well as help detect kidney or prostate problems. Devices and/or applications that monitor the amount and quality of sleep (e.g., using movement detection via accelerometers, sound and/or body temperature) or could detect episodes of insomnia or exacerbations of other sleep issues, such as sleep apnea or snoring. Sleep apnea devices measure parameters such as nasal and oral air flow, blood oxygen and respiratory effort to assess sleep apnea at home and could be used as part of the system described herein. Devices that monitor moisture in the bed could be used to detect bedwetting or to quantify hyperhidrosis or the severity of hot flashes related to menstruation or other health conditions (e.g., the Q-strip™). Surrogate markers (e.g., blood pressure, heart rate, VO2 max, electromyography) could be used to indicate positive and negative changes, which might occur in a continuous manner or as discrete events/changes. Other discrete events include blood clot formation identified in the usual ways (e.g., compression ultrasound, contrast venography, MRI).

Other measurement devices used with different embodiments of the system are described herein that identify discrete or quantitative changes in the status of the human or animal. These devices and measurement systems can be integrated into the present disclosure in varied settings (e.g., home, hospital, care facility) to allow more complete assessment of potential causal relationships involving external signals and biological signals of the human or animal. Cardiovascular measurement devices include electrophysiology analyses, stress echocardiogram, heart or blood vessel ultrasound. Other methods include auscultation of the heart, lungs and other organs using various forms of stethoscopes, both analog and digital. Digital stethoscopes can be used with an app to allow remote telemedicine assessment of the heart or other organs using acoustic methods, such as a smart stethoscope (e.g., Eko™ brand). Acoustic cardiography analytical methods, including those that are used together with ultrasound or ECG can be employed, including those that allow daily home monitoring (e.g., Audicor EkoPatch™) Sleep studies could be done in an in-patient setting as well as at home. Body temperature can be measured in a variety of locations, such as oral, axial, rectal, forehead or in the ear. Musculature and nervous system control of muscles can be assessed via palpation, digital or nondigital electromyography (including wearable electromyography sensors such as with Athos or via other means such as myotonometry or sheer wave electrography. Myotonometry assesses superficial skeletal muscles, ligaments, skin and other biological soft tissues using a digital palpation device that measures tone, spasticity, compliance, elasticity and other parameters. Shear wave electrography can also be used to gather informative data on tissues using ultrasonic bursts combined with ultrasound imaging to determine a variety of properties of biological tissues, including tissue stiffness associated with inflammation or fibrosis. Other techniques for assessing the status of biological tissues include transient electrography and real time electrography. Methods using radio frequency combined with ML/AI can potentially be used to indicate gait, mobility, sleep stages, insomnia, sleep apnea, human pose, emotion detection, monitoring of Parkinson's disease (e.g., Bodycompass™, Emerald Innovations™)

Additional methods of detecting heart rate and other heart-related parameters that can be used by the system described herein include sonar, computer vision, Doppler radar methods, facial photoplethysmographic signals and optical vibrocardiography. Another approach to collecting data on heart function is based on Eulerian Video Magnification (EVM), optical vibrocardiography, Photoplethysmography (PPG) and Videoplethysmography (VPG) (exemplified by Microsoft's Kinect™ sensor).

Apps can help monitor a wide variety of conditions, sometimes based entirely on the patient reporting symptoms (e.g., the Narcolepsy Monitor™ or apps to report symptoms of irritable bowel syndrome, migraines or inflammatory bowel disease). Patterns of symptoms from these types of apps can be integrated with the system disclosed herein to help determine potential causal exposures and events.

Integration with Algorithms Interpreting Patterns Related to Medical Phenomena (e.g., infection prediction, circadian rhythm, prostate cancer examples).

In some embodiments, the system described herein focuses on external stimuli affecting biological responses on a variety of time scales and is integrated into other patterns detected by ML/AI and other means to improve detection of individual and group patterns and predictions. For example, a circadian rhythm analysis focusing on an individual might conclude that their particular circadian pattern of heart rate included a higher than usual increase in heart rate and blood pressure in the evening on most days and this might be viewed as a circadian pattern that might have implications for timing of chemotherapy or other drug delivery. The system described herein, in one example, might find that this person frequently eats seafood in the evening, that seafood increases their resting heart rate and blood pressure and, on the days when they don't eat seafood, their heart rate does not go up as much in the evening. This is potentially very important information for analysis of their circadian rhythms since, for instance, they might decide to stop eating seafood when they begin their drug treatment program. Without discovering the connection with seafood, conclusions about their circadian rhythm would be inaccurate.

In another embodiment, the system described herein is integrated with algorithms that use changes in various biological signals (e.g., heart rate, blood pressure or body temperature) of a human or animal to predict the development of a medical condition, such as cancer or an infection (e.g., prostate cancer, COVID-19). An algorithm for prediction is made using ML/AI or other means without any information regarding reactions resulting from external stimuli such as foods or inhalants. They make predictions with a particular error rate (e.g., 20% false positive prediction that an infection is developing). By integrating the information from the system described herein, the false positive or false negative rate might be decreased because biological signals resulting from external stimuli such as food reactions' effect on the parameters are taken into account.

For instance, if it is found using short-term heart rate tests that a person has a heart rate increase when consuming turkey and citrus and that this also raises their average resting heart rate overall, this could have important effects for a heart rate-based algorithm for predicting infections. The algorithm might predict that an infection was going to occur due to a higher resting heart rate, when in actuality, the person had eaten a higher than usual amount of the foods (turkey and citrus) that cause stress reactions for them. In the case of prostate cancer, changes in prostate specific antigen are used to predict cancer risk or cancer recurrence, but it is known that PSA is affected by inflammation. If food reactions were higher at a particular point in time, stress and inflammation related to the food reaction might increase PSA and lead to an inaccurate assessment of prostate cancer risk or recurrence if it was based on PSA alone. Thus, an algorithm using PSA or other factors would benefit from being integrated with the system described herein. The following examples are just representative and the algorithms/approaches that our system could be integrated with could include diverse types of data and could be complex (e.g., that use imaging, genetics, various "omics" analyses, microbiome analyses and/or other biological data for humans or animals).

Example 53—Integration with Internet of Things (IOT)

In one embodiment, the system described herein could communicate with and control the various systems in the area where inhabitants are located to provide benefits by reducing exposures to external stimuli that are increasing reactions determined through detecting biological signals. This method of control would increase efficiency because the actions taken to reduce the exposures would be initiated only when needed and in a pattern that is calculated to provide the maximum benefit for the least cost. The system can also determine, based on individual data and/or data from many users what level of intermittent exposures to external stimuli and what level of changes in resulting biological signals are optimal. This could be important because it may be beneficial for the user to experience significant variation in levels of some exposures.

One thing that is unique about the system described herein is the use of one or more biological signals that have been used to learn what foods, inhalants and other external stimuli can cause stress or other negative effects to control various IOT systems. Other systems use environmental changes, such as an increase in carbon dioxide or a temperature change to determine when an IOT device is turned on. IOT devices also use heart rate detection or other information to inform the user or a medical professional or some other person. What is different in what is described here is using the individual data on responses to these changes in the environment (external stimuli), often including short-term test data or analyses of short-term changes, to optimize the pattern of use of various IOT devices. The premise of this approach is that there are individual differences in the response to these environmental factors (external stimuli) that can be determined by the sensors detecting biological signals, as described throughout this document. These individual differences can then be used to inform the IOT devices' operation.

Overall, information on reactions as shown by biological signals from the monitored individuals, as described throughout this document, could be used in conjunction with information on where people, animals or plants are currently located and other factors to determine the control of these IOT devices. The location of individuals can be determined by a variety of means, including the person logging the information, cameras, ultra-wide band (UWB) radar, heat detectors, smart speakers (sonar, computer vision, etc.).

For instance, if the user's heart rate increases in a particular room, then the system can instruct the HVAC system to turn on in that room or in the whole house if the biological signal data had determined that this should benefit the user. In one embodiment, a system for treating the air could be turned on, such as methods involving ozone or hydrogen peroxide, to reduce substances in the air that might be causing a reaction. These actions could be initiated alone or in combination with other actions such as instructing the user to do a specified breathing method or use the medical device. A similar approach could be used inside a car, office building, industrial operation or in an outdoor setting (e.g., to control the environment in a barn, silo, feedlot or construction zone) so as not to cause stress or other negative effects for humans or animals.

In another example that illustrates the use of short-term test data, the system could use data showing a heart rate increase reaction to a food (e.g., bleu cheese) that contains allergens that cross-react with mold allergens in the air, along with increasing humidity and the person's increasing heart rate to trigger the activation of a dehumidifier. Furthermore, multiple type of information could be used to determine which of several actions should be taken. Information on the ambient humidity, the amount of particulate matter in the air, the temperature or other factors could help determine whether or not to turn on the dehumidifier, HVAC system, or air filtering system in a particular location.

Self-cleaning or decontamination systems for parts of an area (e.g., home, building, boat, air craft), such as drains, shower, bathrooms, toilets, bathtubs, HVAC components, cooling towers or automatic vacuuming systems, could be turned on if sensors detect biological signals in the inhabitants that indicate the need for action and if the system has determined that these cleaning methods reduce the substances in the environment that are causing stress for the inhabitants. Ozone, hydrogen peroxide, alcohol, ultraviolet light and various other chemicals are the types of agents that can be used alone or in combination in the systems in order to alter the environmental exposure (external stimuli).

In another embodiment, algorithms that take into account uncertainty and/or feedback from the user and from their biological signals can be employed. For example, the system may determine, based on previous data gathered by the system, that the increase in user heart rate might be due to greater humidity increasing mold or a greater particle count in the air (both of which could be detected by sensors present at the location). The greater humidity is determined based on previous data to be most likely and so the dehumidifier is turned on. However, then the system detects that the user's heart rate has continued to go up. When the user also starts to sneeze, the user enters that information into the system (or it is detected by an IOT device such as a smart speaker). The IOT connected air filter is then turned on to reduce the level of particulate matter in the air and then the user's heart rate goes down. The system keeps track of this data for future use to help better inform the decisions made by the system and what information is conveyed to the user or their caregiver.

In another embodiment, cross-reactions between foods/beverages and inhalants are also taken into account and could be included in the analysis mentioned above. The algorithm would combine the information on the response to turning on the air filter with heart rate data from the foods eaten at lunch and inform the user that there is a potential for a cross-reaction between allergens in shrimp and dust mites to be occurring (since both are crustaceans) and that is more likely to be the issue than humidity increasing mold spores. This information about the potential for a cross-reaction could also be provided to a medical professional or caregiver and/or the user could be told to reduce intake of crustaceans and exposure to dust mites.

IOT System Used to Maximize Performance

This type of IOT integrated system using biological signal data could also be used to maximize athletic or cognitive performance by determining what pattern of IOT device activation (e.g., filters, HVAC related systems, object or air cleaning systems) leads to maximal performance with the least sign of physiological stress in a manner analogous to the above examples. For example, an athlete could have a set workout that they undertake every morning. The system could monitor their heart rate and/or other physiological data. Due to changes in temperature in the spring, the HVAC system is on less and the system detects that the heart rate during the workout has been gradually increasing in recent days and so the HVAC system adjusts by turning on using only the circulatory feature in order to filter the air. The system then observes the heart rate during the workout is less once the air is filtered more, and thus the system "learns" that the user is affected by the amount of air circulation. In another example, involving cross-reactions, the system has gathered data on heart rate reactions to various fruits using one of the modes of tests/observations (e.g., short-term tests). The system detects that the heart rate increase in spring during the workouts is only greater when the user has been eating apples, which also cause a relatively greater increase in heart rate during the short-term tests. Birch pollen is found, based on data from the Internet, to be high at this time in the location of the user. And since it is known that apple allergens cross-react with birch pollen, the user is notified that they potentially have an allergy or sensitivity to birch pollen and they might consider reducing apple consumption. Other recommendations might also be made to the user to be aware of pollen levels and perhaps clean areas in their home contaminated with pollen and consider contacting their physician. The user takes action in response to the recommendations and finds that besides improving their workout performance (e.g., they can do more repetitions with less heart rate elevation), they also have a lower resting heart rate and more deep sleep, as shown by their sleep tracking device. In addition, the system analyzing the biological signals that is connected to the IOT devices no longer detects the need to run the circulatory feature of the HVAC system frequently because the user no longer has the same high level of sensitivity to the environment where they do the workouts, thus saving electricity and costs. In another embodiment, one could substitute cognitive performance in the above example. Similar examples are also included in this disclosure where the information is just provided to the user or their caregiver without the inclusion of the IOT component.

Other interventions using IOT systems connected to the assessment of the biological signals could apply probiotic microbes to an environment or antimicrobial or decontaminating treatments (ozone or other chemicals, ultraviolet light) to locations that are determined to be contributing to reactions (e.g., work or living spaces, bathrooms, toilets, bathtubs, showers or drains) by the system described herein.

The IOT connected system could also serve as a way of detecting improvement because it could detect whether the person tolerated higher exposure before becoming stressed as indicated by biological signals of the types described herein, thus resulting in less frequent need to activate connected IOT devices. This could provide additional feedback to the system as to whether the pattern of turning on the connected devices (e.g., dehumidifier, HVAC system, air filter) is leading to longer term benefits to health and wellness.

Example 54—Data

Table 1 shows example data from a 63-year-old Caucasian female mostly recovered from myalgic encephalomyelitis/ chronic fatigue syndrome (heart rate in beats per minute, before, during and after eating various foods for 1 to 2 minutes).

TABLE 1

|  | initial baseline | during | after baseline | difference |
|---|---|---|---|---|
| whey containing bar | 69 | 82 | 76 | 13 |
| whey containing bar | 70 | 82 | 74 | 12 |
| pecan bar | 70 | 81 | 71 | 11 |
| pecan bar | 65 | 72 | 68 | 7 |
| beef jerky | 62 | 68 | 60 | 6 |
| beef jerky | 66 | 77 | 65 | 11 |
| white rice | 70 | 72 | 69 | 2 |
| white rice | 67 | 72 | 66 | 5 |
| hemp hearts | 67 | 71 | 66 | 4 |
| hemp hearts | 64 | 70 | 66 | 6 |

Table 2 shows an example from a 68-year-old Caucasian male in good health (heart rate in beats per minute, before, during and after eating various foods for 1 to 2 minutes).

TABLE 2

|  | before baseline | during | after baseline | difference |
|---|---|---|---|---|
| cashews | 49 | 51 | 50 | 2 |
| strawberries | 50 | 51 | 49 | 1 |
| salmon | 49 | 49 | 47 | 0 |
| avocado | 47 | 48 | 49 | 1 |
| cheese | 49 | 50 | 49 | 1 |
| orange juice | 60 | 64 | 60 | 4 |
| chicken | 60 | 61 | 60 | 1 |
| beer | 61 | 62 | 61 | 1 |
| Egg salad | 58 | 63 | 59 | 5 |

Table 3 shows an example from a 62-year-old Caucasian female with 2 well-controlled autoimmune conditions— (heart rate in beats per minute, before, during and after eating various foods for 1 to 2 minutes).

TABLE 3

|  | initial baseline | during | after baseline | Difference |
|---|---|---|---|---|
| Kellogg granola bar | 63 | 74 | 72 | 9 |
| Annie's granola bar | 69 | 78 | 75 | 9 |
| peanuts | 67 | 75 | 75 | 7 |
| cashews | 64 | 72 | 74 | 8 |
| toast | 70 | 77 | 75 | 7 |
| coffee | 75 | 76 | 75 | 1 |
| chicken | 67 | 80 | 72 | 13 |
| Honey ham | 83 | 80 | 81 | −3 |

Example 55—Correlation and Internet-of-Things

Figure 8:
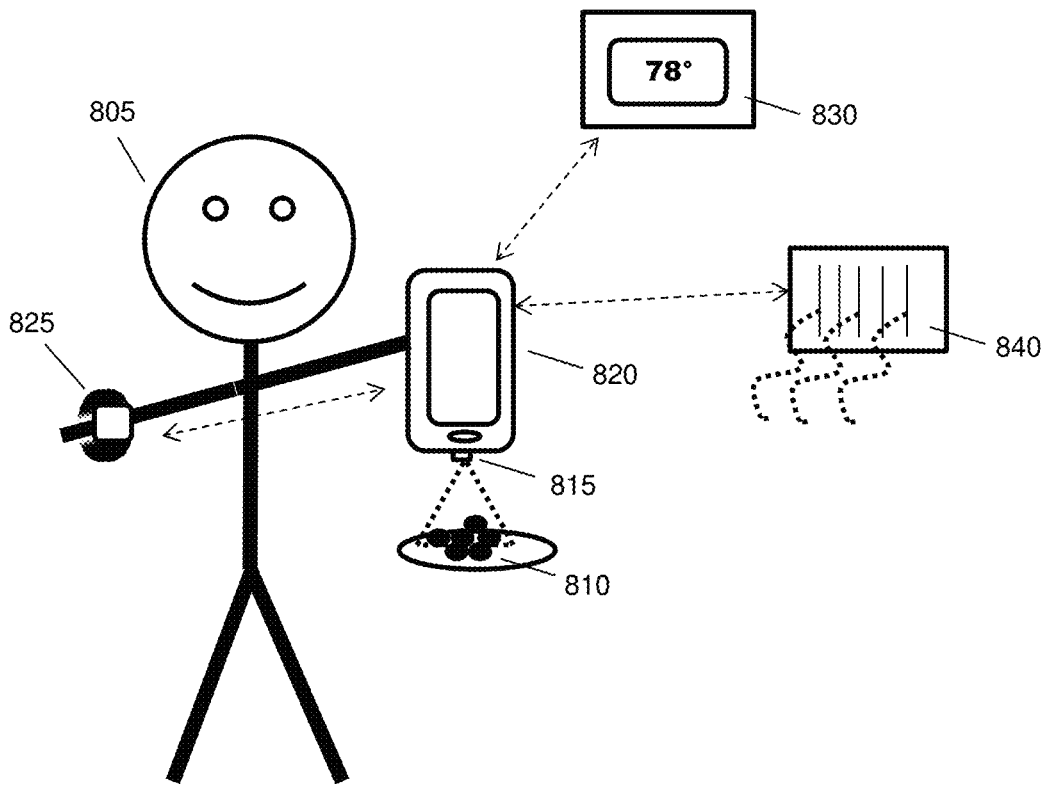
FIG. 8 shows an example of the system being integrated into the Internet-of-things.

FIG. 8 shows an example of correlation between two stimulations and integration with an Internet-of-things system. A user (805) is eating a particular food (810) identified by a first sensor (a camera, 815) in communication with a mobile computing device (820). The user's heart rate is monitored by a second sensor (wrist monitor, 825). A third sensor (thermometer, 830) communicates the ambient temperature to the computing device (820). The computing device (820) uses the data from the three sensors (815, 825, 830) to find a pattern between what is eaten at certain temperatures with heart rate increases. The computing device (820) can also be connected to an internet compatible air conditioning unit (840) to automatically adjust the ambient temperature to avoid food/temperature combinations that put stress (higher heart rate) on the user (805).

A number of embodiments of the disclosure have been described. Nevertheless, it will be understood that various modifications may be made without departing from the spirit and scope of the present disclosure. Accordingly, other embodiments are within the scope of the following claims.

The examples set forth above are provided to those of ordinary skill in the art as a complete disclosure and description of how to make and use the embodiments of the disclosure and are not intended to limit the scope of what the inventor/inventors regard as their disclosure.

Modifications of the above-described modes for carrying out the methods and systems herein disclosed that are obvious to persons of skill in the art are intended to be within the scope of the following claims. All patents and publications mentioned in the specification are indicative of the levels of skill of those skilled in the art to which the disclosure pertains. All references cited in this disclosure are incorporated by reference to the same extent as if each reference had been incorporated by reference in its entirety individually.

It is to be understood that the disclosure is not limited to particular methods or systems, which can, of course, vary. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

The invention claimed is:

1. A method for correlating biometrics of a user with a stimulus external to the user at a location, the method comprising:

entering a plurality of external stimuli of a user into a computing device by a first sensor communicating with the computing device, the user entering data into the computing device, and/or downloading data from the internet to the computing device, the plurality of external stimuli including location data of the user and food or beverage ingested by the user at the location indicated by the location data;

detecting, by a second sensor, heart rate signals of the user;

the second sensor communicating the heart rate signals to the computing device;

the computing device detecting a pattern between the plurality of external stimuli and the heart rate signals;

the computing device computing from the plurality of external stimuli and the heart rate signals a stress index comprising a sum of: a first difference in heart rate from a first baseline prior to ingesting the food or beverage to the heart rate during ingesting the food or beverage, and a second difference in heart rate from a second baseline after ingesting the food or beverage to the first baseline;

the computing device providing information to the user concerning the pattern and the stress index; and the computing device using the pattern and the stress index to control an internet of things controlled device such that the one or more external stimuli is changed for the user and/or the heart rate reaction is reduced.

2. The method of claim 1, wherein the detecting a pattern is performed by machine learning.

3. The method of claim 1, wherein the second sensor is an acoustic sensor.

4. The method of claim 1, wherein the second sensor uses one or more of sonar, Doppler radar, computer vision, facial photoplethysmography, or optical vibrocardiography.

5. The method of claim 1, wherein the internet of things controlled device comprises at least one of: a part of an HVAC system, a dehumidifier, an air filtering system, a decontamination system, and a medical device.

6. The method of claim 1, further comprising the computing device determining cross-reactions based on the one or more external stimuli and providing the user with the cross-reactions.

7. The method of claim 1, further identifying what component of the food or beverage is causing a reaction including retrieving data from a database of ingredients and chemical/allergen content of foods.

8. The method of claim 1, further comprising identifying the food or beverage by computer vision.

9. The method of claim 1, further comprising identifying the food or beverage by prompting the user to enter data about the food if the heart rate increases over a threshold value or percentage change.

10. The method of claim 1, wherein the detecting the pattern includes finding an area under a curve adjusted for a length of time.

11. The method of claim 1, wherein the detecting the pattern includes comparing rates of change in different reactions.

12. The method of claim 1, wherein the detecting the pattern includes averaging a pre-event baseline and a post-event baseline to form a new baseline only if the post-event baseline is lower than the pre-event baseline and the baseline obtained in this way is then subtracted from a peak heart rate level during an exposure event or from an average of a portion of a peak section of a heart rate curve.

13. The method of claim 1, wherein the one or more external stimuli includes a substance inhaled by the user.

14. The method of claim 1, wherein the one or more external stimuli includes a substance the user has come in contact with.

15. The method of claim 13, further comprising:

determining a distance from a nose of the user to a source of the substance; and wherein the determining the pattern includes the distance.

16. The method of claim 1, further comprising:

wherein the detecting the pattern includes data from a microbiome of the user and/or products of the microbiome.

17. The method of claim 1, further comprising exposing the food or beverage to one or more of: heat, saliva, visible light, infrared light, ultraviolet light, x-rays, gamma rays, and enzymes, prior to ingestion, and wherein the detecting the pattern includes data on the one or more external stimuli.

18. A system for correlating biometrics of a user with a stimulus external to the user at a location, the system comprising:

a computing device;

a first sensor configured for detecting one or more external stimuli of a user and entering them into a computing device, the user entering data into the computing device, and/or downloading data from the internet to the computing device, the plurality of external stimuli including location data of the user and food or beverage ingested by the user at the location indicated by the location data;

a second sensor configured to detect heart rate signals of user and communicating the heart rate signals with the computing device;

the computing device configured to detect a pattern between the one or more external stimuli and the heart rate signals;

the computing device computing from the plurality of external stimuli and the heart rate signals a stress index comprising a sum of: a first difference in heart rate from a first baseline prior to ingesting the food or beverage to the heart rate during ingesting the food or beverage, and a second difference in heart rate from a second baseline after ingesting the food or beverage to the first baseline;

an interface of the computing device configured to provide information to the user concerning the pattern and the stress index; and the computing device using the pattern and the stress index to control an internet of things controlled device such that the one or more external stimuli is changed for the user and/or the heart rate reaction is reduced.

19. The system of claim 18, wherein the second sensor is an acoustic sensor.

20. The system of claim 18, wherein the second sensor is configured to use one or more of sonar, Doppler radar, computer vision, facial photoplethysmography, and optical vibrocardiography.

21. The system of claim 18, wherein the internet of things controlled device comprises at least one of: a part of an HVAC system, a dehumidifier, an air filtering system, a decontamination system, and a medical device.

* * * * *